US 8,030,496 B2

(12) United States Patent
Kato et al.

(10) Patent No.: US 8,030,496 B2
(45) Date of Patent: Oct. 4, 2011

(54) INTERMEDIATE COMPOUND FOR SYNTHESIS OF VIRIDIOFUNGIN A DERIVATIVE

(75) Inventors: Tatsuya Kato, Shizuoka (JP); Nobuaki Kimura, Shizuoka (JP); Akemi Mizutani, Shizuoka (JP); Toshihiko Makino, Shizuoka (JP); Kenichi Kawasaki, Kanagawa (JP); Hiroshi Fukuda, Tokyo (JP); Susumu Komiyama, Kanagawa (JP); Takuo Tsukuda, Kanagawa (JP)

(73) Assignee: Chugai Seiyaki Kabushiki Kaisha, Tokyo (JP)

( * ) Notice: Subject to any disclaimer, the term of this patent is extended or adjusted under 35 U.S.C. 154(b) by 53 days.

(21) Appl. No.: 12/656,579

(22) Filed: Feb. 4, 2010

(65) Prior Publication Data
US 2010/0152456 A1 Jun. 17, 2010

Related U.S. Application Data

(62) Division of application No. 11/884,556, filed as application No. PCT/JP2006/302687 on Feb. 16, 2006, now Pat. No. 7,897,783.

(30) Foreign Application Priority Data

Feb. 17, 2005 (JP) .................................. 2005-041153

(51) Int. Cl.
C07D 413/00 (2006.01)
(52) U.S. Cl. ...................................................... 548/230
(58) Field of Classification Search .................... 548/230
See application file for complete search history.

(56) References Cited

U.S. PATENT DOCUMENTS

| 5,498,719 | A | 3/1996 | Marquez et al. |
| 6,303,350 | B1 | 10/2001 | Takesako et al. |
| 2006/0194870 | A1 | 8/2006 | Sudoh et al. |
| 2006/0217434 | A1 | 9/2006 | Aoki et al. |

FOREIGN PATENT DOCUMENTS

| JP | 9-143173 A | 6/1997 |
| WO | WO 98/56755 A1 | 12/1998 |
| WO | WO 2004/071503 A1 | 8/2004 |
| WO | WO 2005/005372 A1 | 1/2005 |

OTHER PUBLICATIONS

Bates et al., "Dianions of glyoxylic acid thioketals: convenient α-keto acid equivalents," Can. J. Chem., 1980, 58:716-722.
DuBois et al., "Observations on theChemistry of alpha-Azido Esters. Efficient Synthesis of a Potently Sweet Homoserine-Dihydrochalcone Conjugate," J. Org. Chem., 1982, 47(7):1319-1323.
Gollnick et al., "Dye-Sensitized Photooxygenation of 2,3-Dihydrofurans: Competing {2+2} Cycloadditions and Ene Reactions of Singlet Oxygen with a Rigid Cyclic Enol Ether System," J. Org. Chem., 1991, 56(12):4017-4027.
Guz et al., "Practical and Highly Selective Oxazolidinethione-Based Asymmetric Acetate Aldol Reactions with Aliphatic Aldehydes," Organic Letters, 2002, 4(13):2253-2256.
Hilbert et al., "Base-Catalyzed Beta-Elimination Reactions. 7. Elimination from 4-(Para-substituted-phenoxy)-2-oxobutanoic Acids," J. Org. Chem., 1978, 43(3):452-459.
Hirai et al., "Totally Synthesis of (±)-Trachyspic Acid and Determination of the Relative Configuration," Organic Letters, 2003, 5(6):857-859.
Myers et al., "Use of Pseudoephedrine as Practical Chiral Auxiliary for Asymmetric Synthesis," J. Am. Chem. Soc., 1994, 116:9361-9362.
Palomo et al., "Highly Diastereoselective Aldol Reactions with Camphor-Based Acetate Enolate Equivalents," J. Org. Chem., 1999, 64:8193-8200.
Radosevich et al., "Vanadium-Catalyzed Asymmetric Oxidation of alpha-Hydroxy Esters Using Molecular Oxygen as Stoichiometric Oxidant," J. Am. Chem. Soc., 2005, 127(4):1090-1091.
Sheldon et al., "Green, Catalytic Oxidations of Alcohols," Acc. Chem. Res., 2002, 35:774-781.
Tavecchia et al., "Degradation Studies of Antibiotic MDL 62,879 (GE2270A) and Revision of the Structure," Tetrahedron, 1995, 51(16):4867-4890.

*Primary Examiner* — Andrew D Kosar
*Assistant Examiner* — Valerie Rodriguez-Garcia
(74) *Attorney, Agent, or Firm* — Foley & Lardner LLP

(57) ABSTRACT

A method whereby a compound having HCV replication inhibitory activity and desired optical activity can be synthesized selectively and at high yield in a small number of steps by using a compound having a specific chiral auxiliary as a starting compound is provided.
A compound represented by the formula (1-8):

$$Y\underset{O}{\overset{}{\diagdown}}\diagup\diagdown\diagup(CH_2)_n\diagdown Q\diagup D \qquad 1\text{-}8$$

wherein Y represents a group represented by the following formula:

(structure showing oxazolidine ring with Z, O, N, R$^1$, R$^2$, R$^3$, R$^4$ substituents)

Q represents a protected carbonyl group; D represents —(CH$_2$)$_m$—R', etc.; and n represents an integer of 0 to 10.

2 Claims, No Drawings

INTERMEDIATE COMPOUND FOR SYNTHESIS OF VIRIDIOFUNGIN A DERIVATIVE

CROSS REFERENCE TO RELATED APPLICATIONS

This application is a Divisional of U.S. application Ser. No. 11/884,556, which is the U.S. National Stage application of PCT/JP2006/302687, filed Feb. 16, 2006, which claims priority from Japanese patent application JP 2005-041153, filed Feb. 17, 2005.

TECHNICAL FIELD

The present invention relates to a production process of a compound having anti-HCV action, an intermediate thereof and a production process of the same.

BACKGROUND ART

A series of compounds disclosed in Patent Publication 1 and represented by the following formula:

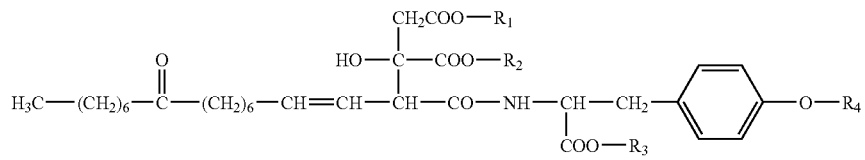

are compounds derived from microorganisms such as the genus *Aureobasidium*, and are recognized to have therapeutic effects against fungal infections and immune diseases. The applicant of the present application found that these compounds have a high HCV replication inhibitory activity as determined by a replicon assay (Patent Publication 2). However, since this series of compounds are derived from microorganisms, their synthesis is difficult and had the problem of only being able to synthesize a limited number of peripheral derivatives from their naturally-occurring compounds. The applicant of the present application then developed a method for completely synthesizing these compounds and analogues thereof without using microorganisms (Patent Publication 3). However, this method comprises a large number of steps and did not render an adequate yield. Consequently, there is a need for a process for highly selectively synthesizing a compound having a desired optical activity at high yield in a small number of steps.

Patent Publication 1: International Publication WO 98/56755
Patent Publication 2: Japanese Patent Application No. 2003-34056
Patent Publication 3: Japanese Patent Application No. 2003-272420

DISCLOSURE OF THE INVENTION

Problem to be Solved by the Invention

As a result of extensive research to solve the aforementioned problems, the applicant of the present application found that by using a compound having a specific chiral auxiliary as a starting compound, a compound having HCV replication inhibitory activity and desired optical activity can be synthesized selectively and at high yield in a small number of steps, thereby leading to completion of the present invention.

Means for Solving the Problems

The present invention relates to a compound represented by the following formula (1-8):

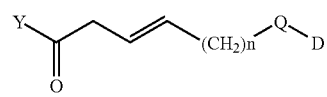

[wherein Y represents a group represented by the following formula:

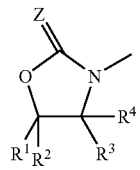

(wherein $R^1$ to $R^4$ may be the same or different and respectively represent a hydrogen atom, optionally substituted aryl group, optionally substituted heteroaryl group, optionally substituted linear or branched alkyl group, optionally substituted linear or branched alkenyl group or optionally substituted linear or branched alkynyl group, and Z represents an oxygen atom or a sulfur atom);

Q represents a protected carbonyl group;

D represents —$(CH_2)_m$—R', where m represents an integer of 0 to 10, and R' represents a hydrogen atom, linear or branched alkyl group, linear or branched alkynyl group, linear or branched alkenyl group, cycloalkyl group, optionally substituted heterocyclic group, optionally substituted aryl group, optionally substituted heteroaryl group, —OX group (where, X represents a hydrogen atom, linear or branched alkyl group, linear or branched alkynyl group, linear or branched alkenyl group, cycloalkyl group or optionally substituted aryl group) or halogen atom; and n represents an integer of 0 to 10].

The present invention also relates to a compound represented by the following formula (7-1):

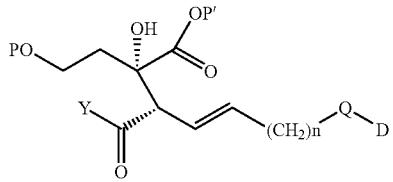
7-1

[wherein Y, Q, D and n are the same as previously defined;
P represents a protecting group of a hydroxyl group; and
P' represents a protecting group of a carboxyl group].

The present invention also relates to a compound represented by the following formula (3-6):

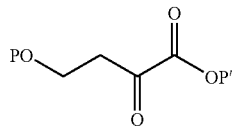
3-6

[wherein P and P' are the same as previously defined].

The present invention further relates to a production process of a compound represented by the following formula (1-8):

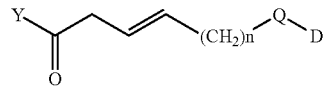
1-8

[wherein Y, Q, D and n are the same as previously defined] comprising a step in which a compound represented by the following formula (1-7):

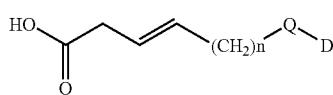
1-7

[wherein Q, D and n are the same as previously defined] is reacted with a compound represented by the following formula:

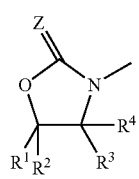

[wherein $R^1$ to $R^4$ and Z are the same as previously defined] in the presence of a base and a condensing agent.

The present invention further relates to a production process of a compound represented by the following formula (7-1):

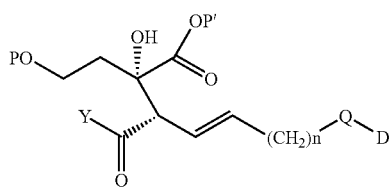
7-1

[wherein Y, Q, D, n, P and P' are the same as previously defined] comprising a step in which a compound represented by the following formula (1-8):

1-8

[wherein Y, Q, D and n are the same as previously defined] is reacted with a compound represented by the following formula (3-6):

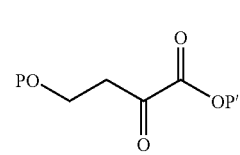
3-6

[wherein P and P' are the same as previously defined] in the presence of a base.

Here, the step in which the reaction is carried out in the presence of a base is more preferably carried out further in the presence of lithium chloride.

The present invention further relates to a production process of a compound represented by the following formula (3-6):

3-6

[wherein P and P' are the same as previously defined] comprising:
1) a step in which a compound represented by the following formula (3-5):

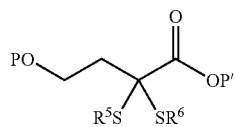
3-5

[wherein P and P' are the same as previously defined, $R^5$ and $R^6$ may be the same or different and respectively represent an optionally substituted aryl group or optionally substituted linear or branched alkyl group, or $R^5$ and $R^6$ together form a 5- or 6-member ring with sulfur atoms respectively bound thereto by together representing an ethylene or propylene chain] is reacted in the presence of an oxidizing agent or an alkylating agent; or 2) a step in which a hydroxyl group of a compound represented by the following formula (5-5):

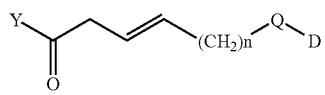

5-5

[wherein P and P' are the same as previously defined] is reacted with an oxidizing agent.

The present invention further relates to a use of the compound of the following formula (1-8):

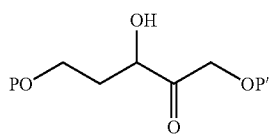

1-8

[wherein Y, Q, D and n are the same as previously defined], in a production process of a compound represented by the following formula (7-6):

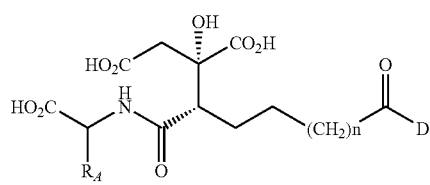

7-6

[wherein $R_A$ represents $-(CH_2)_p-J$, where p represents an integer of 0 to 4, and J represents a hydrogen atom, OH group, SH group, methylthio group, carboxyl group, carbamoyl group, amino group, guanidino group, linear or branched alkyl group, cycloalkyl group, linear or branched alkynyl group, linear or branched alkenyl group, optionally substituted aryl group, optionally substituted heterocyclic group or optionally substituted heteroaryl group; and n and D are the same as previously defined].

The present invention further relates to a compound represented by the following formula (7-3):

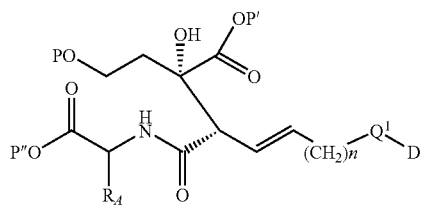

[wherein D, n, P, P' and $R_A$ are the same as previously defined, P''' represents a protecting group of a carboxyl group, and $Q^1$ represents a carbonyl group or a protected carbonyl group].

The present invention further relates to a use of a compound represented by the following formula (7-3):

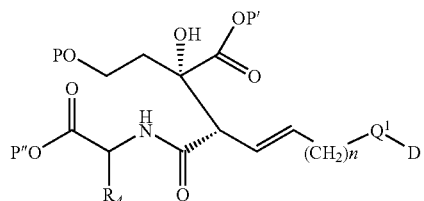

[wherein D, n, P, P', P''', $R_A$ and $Q^1$ are the same as previously defined],
in a production process of a compound represented by the following formula (7-6):

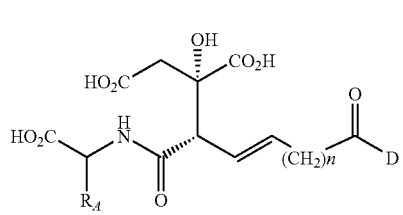

7-6

[wherein $R_A$, n and D are the same as previously defined].

Effects of the Invention

In the present invention, a compound having HCV replication inhibitory activity can be highly selectively synthesized at high yield in a small number of steps by using the compound 1-8 having a specific chiral auxiliary Y.

BEST MODE FOR CARRYING OUT THE INVENTION

In the present description, unless specifically indicated otherwise, a linear or branched alkyl group refers to a linear or branched hydrocarbon group having 1 to 12 carbon atoms, and preferably refers to a linear or branched hydrocarbon group having 1 to 7 carbon atoms, examples of which include a methyl group, ethyl group, propyl group, isopropyl group, n-butyl group, isobutyl group, t-butyl group, pentyl group and heptyl group. In addition, a cycloalkyl group refers to a cyclic hydrocarbon group having 3 to 8 carbon atoms (which may have a double bond and/or triple bond), examples of which include a cyclopentyl group, cyclohexyl group, cycloheptyl group and cyclohexenyl group. In addition, a linear or branched alkenyl group refers to a linear or branched hydrocarbon group having 2 to 8 carbon atoms containing at least one double bond, examples of which include a vinyl group, 1-propenyl group, allyl group and 2-butenyl group. A linear or branched alkynyl group refers to a linear or branched hydrocarbon group having 2 to 8 carbon atoms containing at least one triple bond, examples of which include an ethynyl group, 1-propynyl group, 2-propynyl group, 1-butynyl group and 3-butynyl group.

In the present description, a linear or branched alkyl group, a cycloalkyl group, linear or branched alkenyl group and linear or branched alkynyl group contained in groups such as an alkoxy group, cycloalkyloxy group, alkenyloxy group, alkynyloxy group, aralkyl group, aralkyloxy group, alkylamino group, dialkylamino group, alkylsulfonyl group, alkylthio group or alkylcarbonyl group, are also the same as previously defined.

In the present description, an aryl group refers to an aromatic monocyclic or polycyclic hydrocarbon group, specific examples of which include groups derived from benzene, naphthalene, and anthracene.

In the present description, aryl groups contained in groups such as an aryloxy group, aralkyl group and aralkyloxy group are also the same as previously defined.

In the present description, a heteroaryl group refers to an aromatic 4- to 6-membered monocyclic or 7- to 10-membered bicyclic group (and preferably a monocyclic group) containing, as ring members, 1 to 4 heteroatoms (and preferably 1 or 2 heteroatoms) independently selected from a nitrogen atom, sulfur atom and oxygen atom, specific examples of which include groups derived from furan, thiophene, pyrrole, diazole, pyridine, thiazole, imidazole, pyrimidine, indole, quinoline, oxazole, isoxazole, pyrazine, triazole, thiadiazole, tetrazole, and pyrazole.

In the present description, a heterocyclic group refers to a 4- to 6-membered monocyclic or 7- to 10-membered bicyclic group (and preferably a monocyclic group) containing, as ring members, 1 to 4 heteroatoms (and preferably 1 or 2 heteroatoms) independently selected from a nitrogen atom, sulfur atom and oxygen atom, which may have at least one double bond, specific examples of which include groups derived from pyran, morpholine, tetrahydrofuran, dihydrofuran, tetrahydropyran, dihydropyran, 1,3-dioxane, piperazine, piperidine, and thiomorpholine.

In the present description, an acyl group refers to the aforementioned linear or branched alkyl groups, aryl groups, heteroaryl groups or heterocyclic groups bonded through a carbonyl group, specific examples of which include groups such as an acetyl group, propanoyl group, isopropanoyl group, benzoyl group, naphthyloyl group, and nicotinyl group.

In the present description, the description of optionally substituted means that groups described in this manner may be substituted with a respectively previously defined group such as a linear or branched alkyl group, linear or branched alkoxy group, linear or branched alkenyl group, linear or branched alkenyloxy group, linear or branched alkynyl group, linear or branched alkynyloxy group, cycloalkyl group, cycloalkyloxy group, cyano group, nitro group, trifluoromethyl group, halogen atom, aryl group, aryloxy group, heteroaryl group, aralkyl group, aralkyloxy group, amino group, alkylamino group, dialkylamino group, acyl group, alkylsulfonyl group, alkoxy group, carbamoyl group, alkylthio group, carboxyl group, alkylcarboxyl group, formyl group, and sulfonamide group. Among these substituents, aryl groups, aryloxy groups, heteroaryl groups, aralkyl groups and aralkyloxy groups may be further mono-, di- or trisubstituted with, for example, a halogen atom, linear or branched alkenyloxy group, cycloalkyl group, cycloalkyloxy group, cyano group, nitro group, trifluoromethyl group, halogen atom, aryl group, aryloxy group, heteroaryl group, aralkyl group, aralkyloxy group, amino group, alkylamino group, dialkylamino group, acyl group, alkylsulfonyl group, alkoxy group, carbamoyl group, alkylthio group, carboxyl group, alkylcarboxyl group, formyl group, and sulfonamide group.

In the present description, a protecting group of a hydroxyl group or a carboxyl group refers to a group for protecting these reactive groups from an unwanted chemical reaction, and which can be easily removed following completion of the reaction. Specifically, there may be mentioned protecting groups described in the literature such as "Protective Groups in Organic Synthesis, Theodora Greene (ed.), 1999, Wiley-Interscience". In the case of protecting a hydroxyl group, a group such as a t-butyldiphenylsilyl group (hereinafter referred to as "TBDPS group"), tetrahydropyranyl group, methoxymethyl group, benzyl group, trimethylsilyl group, p-methoxybenzyl group, t-butyldimethylsilyl group (hereinafter referred to as "TBS group") and acyl group can be used preferably. In addition, in the case of protecting a carboxyl group, a group such as a linear or branched alkyl group having 1 to 6 carbon atoms (such as a methyl group, ethyl group or t-butyl group), a linear or branched alkenyl group having 1 to 6 carbon atoms (such as an allyl group) and a benzyl group can be used preferably.

In the present description, a protected carbonyl group refers to a carbonyl group protected with a carbonyl group protecting group. A carbonyl group protecting group is a group for protecting these reactive groups from an unwanted chemical reaction, and which can be easily removed following completion of the reaction, specific examples of which include protecting groups described in the literature such as "Protective Groups in organic Synthesis, Theodora Greene (ed.), 1999, Wiley-Interscience". Examples of carbonyl group protecting groups include cyclic or acyclic ketal groups, cyclic or acyclic acetal groups, cyclic or acyclic thioketal groups and cyanohydrin groups. In particular, cyclic or acyclic ketal groups and cyclic or acyclic thioketal groups can be used preferably. Specifically, there may be mentioned dimethoxymethylene, bis(2,2,2-trichloroethyloxy)methylene, dibenzylmethylene, bis(2-nitrobenzyloxy)methylene, bis(acetyloxy)methylene, 1,3-dioxane, 5-methylene-1,3-dioxane, 5,5-dibromo-1,3-dioxane, 5-(2-pyridyl)-1,3-dioxane, 1,3-dioxolane, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy, 1,5-dihydro-3H-2,4-benzodioxepine, bis(methylthio)methylene, bis(ethylthio)methylene, bis(propylthio)methylene, bis(butylthio)methylene, bis(phenylthio)methylene, bis(benzylthio)methylene, bis(acetylthio)methylene, 1,3-dithiane, 1,3-dithiolane, 1,5-dihydro-3H-2,4-benzodithiepine, trimethylsilyloxymethylthiomethylene, trimethylsilyloxyethylthiomethylene, trimethylsilyloxyphenylthiomethylene, methyloxymethylthiomethylene, methyloxyphenylthiomethylene, methyloxy-2-(methylthio)ethylthiomethylene, 1,3-oxathiolane, bis(methylselenenyl)methylene, bis(phenylselenenyl)methylene, cyano(acetyloxy)methylene, cyano(trimethylsilyloxy)methylene, cyano(1-ethoxyethyloxy)methylene, cyano(tetrahydropyranyloxy)methylene, N,N-dimethylhydrazone, 2,4-dinitrophenylhydrazone, oxime, O-methyloxime, O-benzyloxime, O-phenylthiomethyloxime, oxazolidine, N-methylthiazolidine, N-napthylthiazolidine, N-benzylthiazolidine and the like, and dimethoxymethylene, 1,3-dioxane, 1,3-dioxolane, 1,3-dithiane and 1,3-dithiolane can be used preferably.

The following provides a detailed description of compounds of the present invention.

A compound of formula (I-8) of the present invention is a compound represented by the following formula:

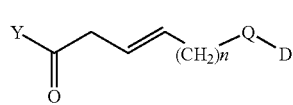

1-8

Here, Y represents a group represented by the following formula:

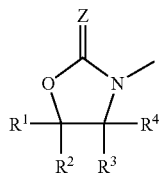

[wherein $R^1$ to $R^4$ may be the same or different and respectively represent a hydrogen atom, optionally substituted aryl group, optionally substituted heteroaryl group, optionally substituted linear or branched alkyl group, optionally substituted linear or branched alkenyl group or optionally substituted linear or branched alkynyl group, and Z represents an oxygen atom or a sulfur atom].

Groups $R^1$ to $R^4$ contained in group Y may be the same or different and respectively represent the groups indicated above. Here, preferable examples of an optionally substituted aryl group include an optionally substituted phenyl group and an optionally substituted naphthyl group. Specifically, a phenyl group, a p-tolyl group and others are preferred. In addition, preferable examples of an optionally substituted heteroaryl group include an optionally substituted pyridyl group and an optionally substituted pyrimidyl group. Preferable examples of an optionally substituted linear or branched alkyl group include methyl, ethyl, isopropyl and t-butyl groups. Preferable examples of an optionally substituted linear or branched alkenyl group include vinyl, allyl and 1-methylvinyl groups. In addition, preferable examples of an optionally substituted linear or branched alkynyl group include ethynyl and 2-methylethynyl groups.

In addition, although Z contained in group Y represents an oxygen atom or a sulfur atom, Z preferably represents a sulfur atom in consideration of the ease of elimination in steps 7-2 and 7-3 to be subsequently described and in terms of the high selectivity thereof.

Y is preferably a group represented by the following formula:

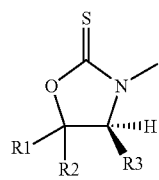

[wherein $R^1$ and $R^2$ may be the same or different and respectively represent an optionally substituted aryl group (such as particularly preferably an optionally substituted phenyl group) or an optionally substituted heteroaryl group (such as particularly preferably a pyridyl group), and $R^3$ represents an optionally substituted linear or branched alkyl group (such as particularly preferably an isopropyl group or t-butyl group)], and Y is more preferably a group represented by the following formula.

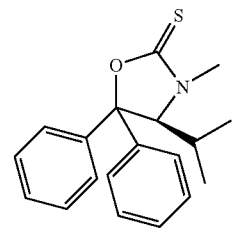

In the compound of this formula (1-8), Q is a protected carbonyl group, preferably a cyclic or acyclic ketal group or cyclic or acyclic thioketal group, and particularly preferably a 1,3-dioxane-2,2-diyl group or 1,3-dioxolane-2,2-diyl group.

In addition, in the compound of the aforementioned formula (1-8), D represents —$(CH_2)_m$—R', wherein m represents an integer of 0 to 10 and preferably an integer of 3 to 8. In addition, R' represents a hydrogen atom, linear or branched alkyl group, linear or branched alkynyl group, linear or branched alkenyl group, cycloalkyl group, optionally substituted heterocyclic group, optionally substituted aryl group, optionally substituted heteroaryl group, —OX group (wherein X represents a hydrogen atom, linear or branched alkyl group, linear or branched alkynyl group, linear or branched alkenyl group, cycloalkyl group or optionally substituted aryl group) or a halogen atom, and R' is preferably a hydrogen atom, linear or branched alkenyl group, cycloalkyl group or optionally substituted aryl group (and particularly preferably a phenyl group), and particularly preferably a hydrogen atom.

In addition, in the compound of the aforementioned formula (1-8), n represents an integer of 0 to 10, preferably an integer of 2 to 8, more preferably an integer of 4 to 8, and even more preferably 6.

A specific example of such a compound represented by formula (1-8) is indicated below.

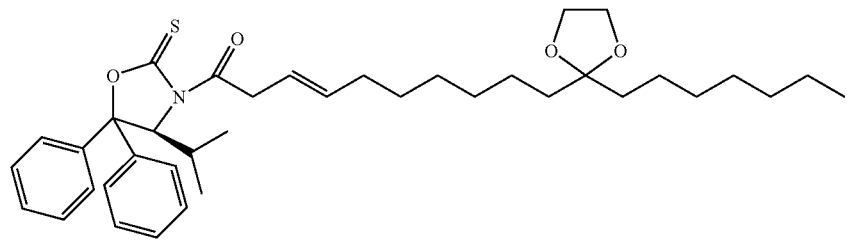

A compound represented by formula (7-1) of the present invention is a compound represented by the following formula:

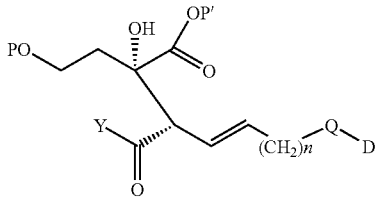

wherein Y, Q, D and n are the same as previously defined for the compound of the aforementioned formula (1-8), preferable examples of which are the same as indicated for the compound of the aforementioned formula (1-8). In addition, in the formula, P represents a protecting group of a hydroxyl group, and P' represents a protecting group of a carboxyl group. Although P can be any arbitrary group provided it is a group that protects a hydroxyl group, examples of groups that can be used include a t-butyldiphenylsilyl group, tetrahydropyranyl group, methoxymethyl group, benzyl group, trimethylsilyl group, p-methoxybenzyl group, t-butyldimethylsilyl group and acyl group, with a t-butyldiphenylsilyl group and t-butyldimethylsilyl group being able to be used particularly preferably. In addition, although P' can be any arbitrary group provided it is a group that protects a carboxyl group, examples of groups that can be used preferably include a methyl group, ethyl group, t-butyl group, allyl group and benzyl group, with a t-butyl group being able to be used particularly preferably.

Specific examples of such compounds of formula (7-1) are indicated below.

A compound of formula (3-6) of the present invention is a compound represented by the following formula:

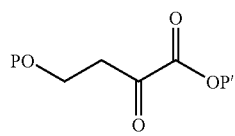

wherein P and P' are the same as previously defined for the compound of the aforementioned formula (7-1).

Specific examples of such compounds of formula (3-6) are indicated below.

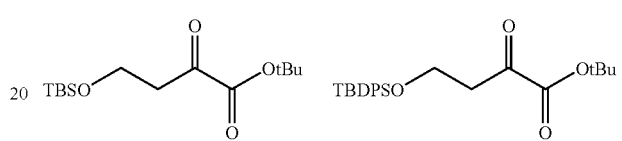

A compound of formula (7-3) of the present invention is a compound represented by the following formula:

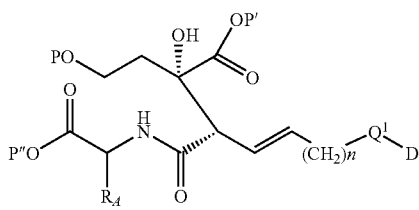

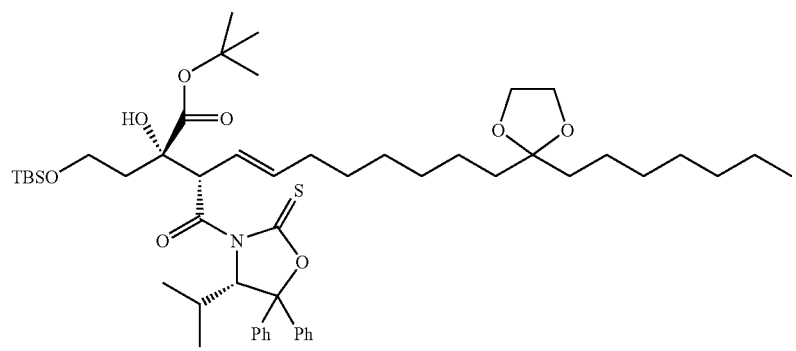

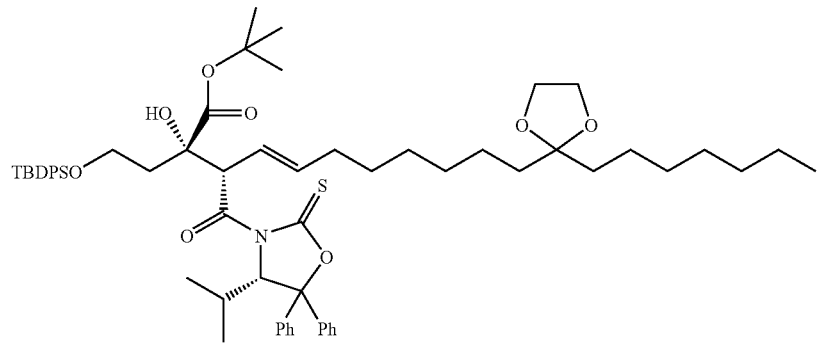

wherein D, n, P and P' are the same as previously defined for the compound of the aforementioned formula (7-1). P'' represents a protecting group of a carboxyl group. $R_4$ represents $-(CH_2)_p$-J, wherein p represents an integer of 0 to 4, and J represents a hydrogen atom, OH group, SH group, methylthio group, carboxyl group, carbamoyl group, amino group, guanidino group, linear or branched alkyl group, cycloalkyl group, linear or branched alkynyl group, linear or branched alkenyl group, optionally substituted aryl group, optionally substituted heterocyclic group or optionally substituted heteroaryl group. In addition, $Q^1$ represents a carbonyl group or a protected carbonyl group.

Specific examples of such compounds of formula (7-3) are indicated below.

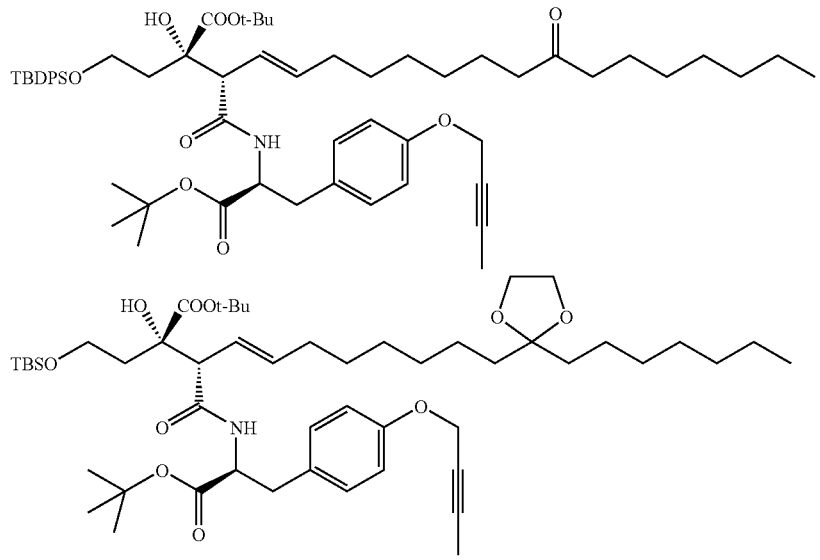

The following provides a detailed description of a production process for the aforementioned compounds.

Process for Preparation of a Compound of Formula (1-8)

A compound of the above formula (1-8) can be synthesized by means of a process comprising a step in which a compound represented by the following formula (1-7):

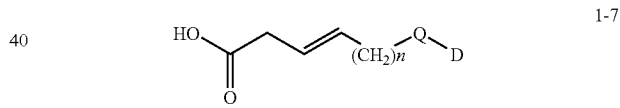

1-7

[wherein Q, D and n are the same as previously defined] is reacted with a compound represented by the following formula:

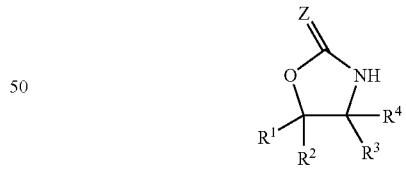

[wherein $R^1$ to $R^4$ and Z are the same as previously defined] in the presence of a base and a condensing agent.

Further, this compound of the formula (1-7) can be, starting from Compound (1-1), synthesized according to the following steps, so that the compound of the formula (1-8) can be finally obtained (General Step-1).

General Step-1

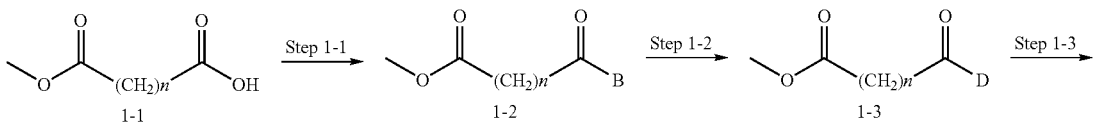

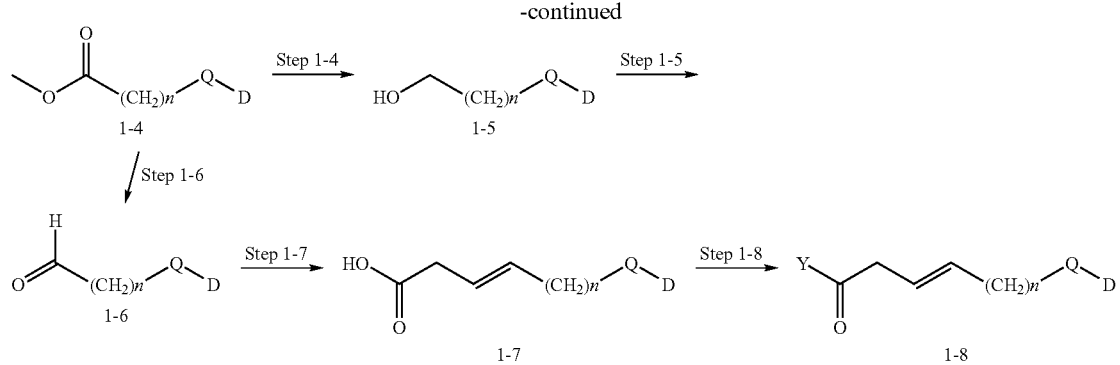

In the above formulae, B is a leaving group of a carboxyl group such as a halogen atom, methylmethoxyamino group or 1-imidazolyl group; Q is a protected carbonyl group; and Y, n and D are as defined above.

Step 1-1

Compound 1-1 is a commercially available compound (e.g., Product Name: Azelaic acid monomethyl ester, manufactured by Tokyo Kasei KK). This compound is reacted, in a solvent inactive to the reaction, or without solvent depending on reactions and in the presence of 0.01 to 1 equivalent, preferably 0.01 to 0.1 equivalent of dimethylformamide, with 1 equivalent to a large excess, preferably 1 to 3 equivalents of halogenating agent including chlorinating agents such as oxalyl dichloride, thionyl chloride or phosphorous oxychloride, and fluorinating agents such as cyanuric fluoride, imidazolylating agents such as carbodiimidazole, amines such as methoxymethylamine and amidating agents; or reacted with acid halogenating agents such as pivaloyl chloride and acetyl chloride, phosphorylating agents such as dichlorotriphenylphosphorane, and thiolating agents such as phenylthiol, so as to obtain Compound 1-2. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, and chloroform can be used alone or in the form of a mixture thereof, among which toluene, N,N-dimethylformamide, and methylene chloride are preferable. The reaction is carried out at a temperature between −78 and 50° C., preferably a temperature between −15 and 25° C., and is completed usually in 30 minutes to 10 hours. In the case of the reactions by means of an imidazolylating agent such as carbodiimidazole, an amine such as methoxymethylamine and amidating agents, the reaction is preferably carried out in the presence of a base. As the base, for example, 1 equivalent to a large excess, preferably 1 to 3 equivalents of tertiary amine such as pyridine, triethylamine or diisopropylethylamine are used, among which triethylamine and diisopropylethylamine are preferable.

Step 1-2

Compound 1-2 obtained in the step 1-1 is reacted, in a solvent inactive to the reaction, and in the presence of a catalytic amount to 1 equivalent, preferably 0.01 to 0.1 equivalent of catalyst, with one equivalent to a large excess, preferably 1 to 2 equivalents of Grignard reagent or an organic lithium reagent having desired group D, so as to obtain Compound 1-3 with a group D being introduced. For the solvent inactive to the reaction, any solvent can be employed as long as it is inactive to the reaction, and is not particularly limited. However, for example, various ethers such as diethyl ether, tetrahydrofuran and dioxane; benzene, n-hexane, toluene, cyclohexane, N,N-dimethylformamide, dimethyl sulfoxide, or the like can be used alone or in the form of a mixture thereof, among which diethyl ether, tetrahydrofuran, dioxane, and toluene are preferable. The reaction is carried out at a temperature between −78 and 100° C., preferably a temperature between −78 and 30° C., and is completed usually in 20 minutes to 5 hours. As the catalyst, for example, copper compounds, cadmium compounds, iron compounds, cobalt compounds, or zinc compounds are used, among which copper chloride and tris(2,4-pentanedionato) iron are preferable.

Step 1-3

Compound 1-3 obtained in the step 1-2 is reacted, in a solvent inactive to the reaction, and in the presence of a catalytic amount to 1 equivalent, preferably 0.05 to 0.5 equivalent of acid catalyst, with 1 equivalent to a large excess, preferably 1 to 3 equivalents of a reagent for adding a protective group of a carbonyl group, for example, ethylene glycol, bis(trimethylsiloxy)ethane, 2-alkoxy-1,3-dioxolane, 2-ethyl-2-methyl-1,3-dioxolane, 2-dimethylamino-1,3-dioxolane, triethyl formate dehydrating agent, or the like, preferably with ethylene glycol, so as to obtain Compound 1-4 of which carbonyl group is protected. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which benzene and toluene are preferable. The reaction is carried out at a temperature between 40 and 150° C., preferably a temperature between 80 and 100° C., and is completed usually in 2 hours to 30 hours. As the acid catalyst, for example, toluene sulfonic acid, pyridinium paratoluenesulfonate, diluted hydrochloric acid, diluted sulfuric acid, acetic acid, trifluoroborane diethyl ether complex, trimethylsilane chloride, aluminium oxide, copper chloride, adipic acid, selenium oxide, ruthenium chloride, or ion-exchange resin is used, among which toluenesulfonic acid and pyridinium paratoluenesulfonate are preferable.

Step 1-4

Compound 1-4 obtained in the step 1-3 is reacted, in a solvent inactive to the reaction, with 1 equivalent to a large excess, preferably 1 to 2 equivalents of reducing agent, so as to obtain Compound 1-5. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, or the like can be used alone or in the form of a mixture thereof, among which diethyl ether, tetrahydrofuran, and dioxane are preferable. The reaction is carried out at a temperature between −20 and 30° C., preferably a temperature between 0 and 10° C., and is completed usually in 30 minutes to 2 hours. As the reducing agent, for example, lithium aluminium hydride, diisobutylaluminium hydride, Red-Al, lithium borane tetrahydride, selectride, or superhydride is used, among which lithium aluminium hydride is preferable.

Step 1-5

Compound 1-5 obtained in the step 1-4 is reacted, in a solvent inactive to the reaction, with 1 equivalent to a large excess, preferably 1 to 1.2 equivalents of oxidizing agent, so as to obtain Compound 1-6. For the solvent inactive to the reaction, any solvent can be employed as long as it is inactive to the reaction, and is not particularly limited. However, for example, various ethers such as diethyl ether, tetrahydrofuran and dioxane; benzene, n-hexane, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which benzene, toluene, cyclohexane, 1,2-dichloroethane, N,N-dimethylformamide, dimethyl sulfoxide, methylene chloride, and chloroform are preferable. The reaction is carried out at a temperature between −78 and 30° C., and is completed usually in 30 minutes to 10 hours. For oxidation, for example, potassium permanganate, and Swern-oxidation, DMSO oxidation, Collins oxidation, TEMPO oxidation, or sulfur trioxide-sulfur trioxide pyridine complex oxidation are used, among which TEMPO oxidation and sulfur trioxide-pyridine complex oxidation are preferable.

Step 1-6

Compound 1-4 obtained in the step 1-3 is reacted, in a solvent inactive to the reaction, with 1 equivalent to a large excess, preferably 1 to 1.2 equivalents of reducing agent, so as to obtain Compound 1-6 directly without going through the steps of 1-4 and 1-5. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, or the like can be used alone or in the form of a mixture thereof, among which tetrahydrofuran and toluene are preferable. The reaction is carried out at a temperature between −78 and 30° C., preferably a temperature between −78 and 0° C., and is completed usually in 30 minutes to 2 hours. As the reducing agent, for example, a composite body of reducing agents such as diisobutylaluminium hydride, lithium aluminium hydride, Red-Al, lithium borane tetrahydride, selectride and superhydride, and a secondary amine such as diethylamine, pyrrolidine or pyrimidine; and, as the catalyst, a base such as potassium t-butoxide is used, among which diisobutylaluminium hydride is preferable.

Step 1-7

Compound 1-6 obtained in the step 1-5 or 1-6 is reacted, in a solvent inactive to the reaction, and in the presence of 1 equivalent to a large excess, preferably 1 to 1.5 equivalents of base, with 1 equivalent to a large excess, preferably 1 to 1.2 equivalents of malonic acid, so as to obtain Compound 1-7. For the solvent inactive to the reaction, any solvent can be employed as long as it is inactive to the reaction, and is not particularly limited. However, for example, various ethers such as diethyl ether, tetrahydrofuran and dioxane; benzene, n-hexane, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which benzene, n-hexane, toluene, and cyclohexane are preferable. The reaction is carried out at a temperature between 50 and 150° C., preferably a temperature between 80 and 110° C., and is completed usually in 1 hour to 30 hours. As the base, for example, triethylamine, diisopropylethylamine, pyridine, diazabicycloundecene, potassium t-butoxide, or sodium methoxide is used, among which triethylamine and diisopropylethylamine are preferable.

Step 1-8

Compound 1-7 obtained in the step 1-7 is reacted, in a solvent inactive to the reaction, and in the presence of a catalytic amount to a large excess, preferably a catalytic amount to 1.2 equivalents of base, and of 1 equivalent to a large excess, preferably 1 to 1.2 equivalents of condensing agent, with 1 equivalent to a large excess, preferably 1 to 1.2 equivalents of chiral auxiliary, so as to obtain Compound 1-8. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which toluene and methylene chloride are preferable. The reaction is carried out at a temperature between 0 and 50° C., preferably a temperature between 0 and 25° C., and is completed usually in 30 minutes to 10 hours. As the base, for example, triethylamine, N,N-dimethylaminopyridine, N,N-diisopropylethylamine, pyridine, or the like is used, among which triethylamine and N,N-dimethylaminopyridine are preferable. As the condensing agent, for example, dicyclohexylcarbodiimide (DCC), diisopropylcarbodiimide (DIPC), N-ethyl-N-3-dimethylaminopropyl carbodiimide (EDC=WSCI) and hydrochloride thereof (WSC.HCl), benzotriazol-1-yl-tris(dimethylamino)phosphonium hexafluorophosphate (BOP), diphenylphosphoryl azide (DPPA), or the like can be used alone, or N-hydroxysuccinimide (HONSu), 1-hydroxybenzotriazole (HOBt), 3-hydroxy-4-oxo-3,4-dihydro-1,2,3-benzotriazine (HOObt), and the like can be used in combination, among which N-ethyl-N-3-dimethylaminopropyl carbodiimide hydrochloride (WSC.HCl) is preferable. As the chiral auxiliary, for example, (R or S) optically-active alcohol or optically-active amine and N-alkylated form thereof, α and β-amino acid and N-alkylated form thereof, or alkyl esters and a compound consisting of a combination thereof, or a 5-membered or 6-membered ring product derived from the above optically-active substance is used. In particular, a compound of the formula:

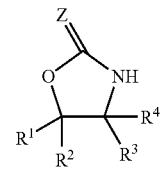

[wherein $R^1$ to $R^4$ and Z are as defined above] can be used. As such compound, (R or S)-4-alkyl or 4,4-dialkyl, 5-alkyl or 5,5-dialkyl oxazolidine-2-thione or the combination thereof, (R or S)-4-alkyl or 4,4-dialkyl, 5-alkyl or 5,5-dialkyl oxazolidin-2-one or the combination thereof, etc. can be used, among which (S)-4-isopropyl-5,5-diphenyloxazolidin-2-one and (S)-4-isopropyl-5,5-diphenyloxazolidine-2-thione are preferable.

Further, the compound of the formula (I-6) which is an intermediate compound in the above General Step-1 can also be prepared according to the following step (General Step-2):

General Step-2

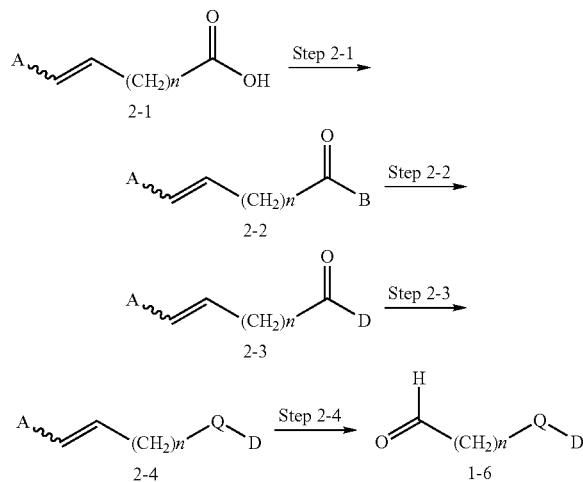

In the formulae, A is a hydrogen atom, or a linear or branched alkyl group, B is a leaving group such as a halogen atom, methylmethoxyamino group or 1-imidazolyl group, and n, D and Q are as defined above.

Step 2-1

Compound 2-1 is a commercially available compound (e.g., Product Name: Oleic acid, manufactured by Tokyo Kasei KK). This compound is reacted, in a solvent inactive to the reaction, or without solvent depending on reactions, with 1 equivalent to a large excess, preferably 1 to 3 equivalents of halogenating agent including chlorinating agents such as oxalyl dichloride, thionyl chloride or phosphorous oxychloride, and fluorinating agents such as cyanuric fluoride, imidazolylating agents such as carbodiimidazole, amines such as methoxymethylamine and amidating agents; or reacted with acid halogenating agents such as pivaloyl chloride and acetyl chloride, phosphorylating agents such as dichlorotriphenylphosphorane or thiolating agents such as phenylthiol, so as to obtain Compound 2-2 with a group B being introduced. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which toluene, N,N-dimethylformamide, and methylene chloride are preferable. The reaction is carried out at a temperature between 0 and 50° C., preferably a temperature between 0 and 25° C., and is completed usually in 30 minutes to 10 hours. In the case of the reactions by means of imidazolylating agents such as carbodiimidazole, amines such as methoxymethylamine and amidating agents, the reaction is preferably carried out in the presence of a base. As the base, for example, 1 equivalent to a large excess, preferably 1 to 3 equivalents of tertiary amine such as pyridine, triethylamine and diisopropylethylamine are used, among which triethylamine or diisopropylethylamine is preferable.

Step 2-2

Compound 2-2 obtained in the step 2-1 is reacted, in a solvent inactive to the reaction, and in the presence of a catalytic amount to 1 equivalent, preferably 0.01 to 0.1 equivalent of catalyst, with one equivalent to a large excess, preferably 1 to 2 equivalents of Grignard reagent or an organic lithium reagent having desired group D, so as to obtain Compound 2-3. For the solvent inactive to the reaction, any solvent can be employed as long as it is inactive to the reaction, and is not particularly limited. However, for example, various ethers such as diethyl ether, tetrahydrofuran and dioxane; benzene, n-hexane, toluene, cyclohexane, N,N-dimethylformamide, dimethyl sulfoxide, or the like can be used alone or in the form of a mixture thereof, among which diethyl ether, tetrahydrofuran, dioxane, and toluene are preferable. The reaction is carried out at a temperature between −78 and 100° C., preferably a temperature between −78 and 30° C., and is completed usually in 20 minutes to 5 hours. As the catalyst, for example, copper compounds, cadmium compounds, iron compounds, cobalt compounds, or zinc compounds are used, among which copper chloride and tris(2,4-pentanedionato) iron are preferable.

Step 2-3

Compound 2-3 obtained in the step 2-2 is reacted, in a solvent inactive to the reaction, and in the presence of a catalytic amount to 1 equivalent, preferably 0.05 to 0.5 equivalent of acid catalyst, with 1 equivalent to a large excess, preferably 1 to 3 equivalents of a reagent for adding a protective group of a carbonyl group, for example, ethylene glycol, bis(trimethylsiloxy)ethane, 2-alkoxy-1,3-dioxolane, 2-ethyl-2-methyl-1,3-dioxolane, 2-dimethylamino-1,3-dioxolane, triethyl formate dehydrating agent, or the like, so as to obtain Compound 2-4 of which carbonyl group is protected. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which benzene and toluene are preferable. The reaction is carried out at a temperature between 40 and 150° C., preferably a temperature between 80 and 100° C., and is completed usually in 2 hours to 30 hours. As the acid catalyst, for example, toluenesulfonic acid, pyridinium paratoluenesulfonate, diluted hydrochloric acid, diluted sulfuric acid, acetic acid, trifluoroborane diethyl ether complex, trimethylsilane chloride, aluminium oxide, copper chloride, adipic acid, selenium oxide, ruthenium chloride, or ion-exchange resin is used, among which toluenesulfonic acid and pyridinium paratoluenesulfonate are preferable.

Step 2-4

Compound 2-4 obtained in the step 2-3 is reacted, in a solvent inactive to the reaction, with 1 equivalent to a large excess, preferably 1 to 1.5 equivalents of oxidizing agent, so as to obtain Compound 1-6. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, ethanol, methanol, propanol, or the like can be used alone or in the form of a mixture thereof, among which methylene chloride and ethanol are preferable. The reaction is carried out at a temperature between −78 and 30° C., preferably a temperature between −78 and 0° C., and is completed usually in 30 minutes to 10 hours. For the oxidizing agent, for example, a method by means of ozone oxidation, the combination of a metal catalyst such as osmium tetraoxide, tungsten, vanadium, molybdenum or cobalt, and a co-oxidizing agent such as hydrogen peroxide, meta-periodic acid, oxygen or oxone, or other methods by means of iodic acid decomposition is used after going through epoxide using a peracid, among which ozone oxidation is preferable.

Process for Preparation of a Compound of Formula (3-6)

A compound of the formula (3-6) of the present invention can be synthesized by means of a process comprising 1) a step in which a compound represented by the formula (3-5):

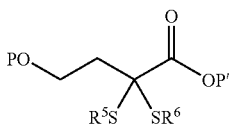

3-5

[wherein P and P' are the same as previously defined; and $R^5$ and $R^6$ may be the same or different and respectively represent an optionally substituted aryl group or optionally substituted linear or branched alkyl group, or $R^5$ and $R^6$ together form a 5- or 6-membered ring with sulfur atoms respectively bound thereto by together representing an ethylene or propylene chain] is reacted in the presence of an oxidizing agent or an alkylating agent; or 2) a step in which a hydroxyl group of a compound represented by the formula (5-5):

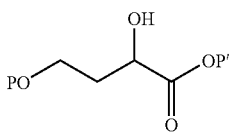

5-5

[wherein P and P' are the same as previously defined] is reacted with an oxidizing agent.

In the process for the synthesis from the compound of the formula (3-5) mentioned above in 1), this compound of the formula (3-5) can be, starting from the compound of the formula (3-1), synthesized according to the following steps, so that the compound of the formula (3-6) can be finally obtained (General Step-3).

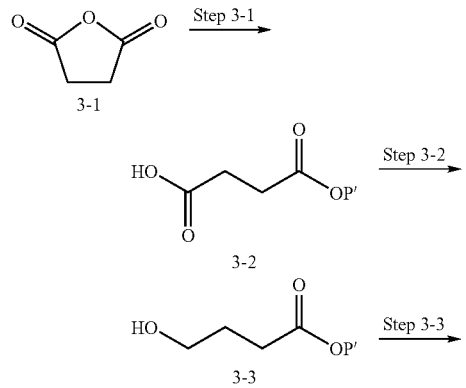

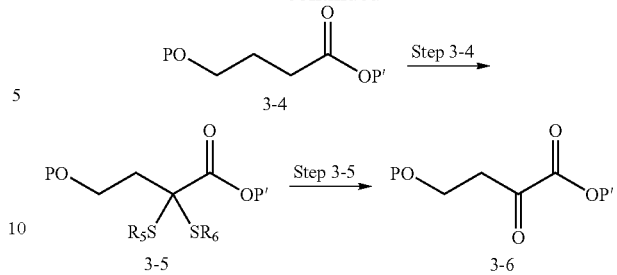

In the formulae, P, P', $R^5$ and $R^6$ are as defined above.

Step 3-1

Compound 3-2 can be synthesized by means of the process disclosed in the reference (J. Org. Chem. 68, 6679-6684 (2003)). Specifically, succinic anhydride and N-hydroxysuccinimide are reacted, in a solvent inactive to the reaction, and in the presence of 1 equivalent to a large excess, preferably 1 to 3 equivalents of base, with 1 equivalent to a large excess, preferably 1 to 10 equivalents of compound which can be a protective group of carboxylic acid, for example, an alcohol, so as to obtain Compound 3-2. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof. The reaction is carried out at a temperature between 50 and 150° C., preferably a temperature between 80 and 110° C., and is completed usually in 30 minutes to 30 hours. As the base, for example, triethylamine, N,N-dimethylaminopyridine, N,N-diisopropylethylamine, or pyridine is used, among which triethylamine and N,N-dimethylaminopyridine are preferable. As the alcohol in the case of using an alcohol as a compound which can be a protective group of carboxylic acid, for example, ethanol, methanol, propanol, isopropanol, t-butanol, or the like is used, among which t-butanol is preferable.

Step 3-2

Compound 3-3 can be synthesized by means of the process disclosed in the reference (J. Org. Chem. 68, 6679-6684 (2003)). Specifically, Compound 3-2 obtained in the step 3-1 is reacted, with 1 equivalent to a large excess, preferably 1 to 1.2 equivalents of reducing agent in a solvent inactive to the reaction, so as to obtain Compound 3-3. For the reaction solvent, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, dimethyl sulfoxide, methylene chloride, chloroform, or the like can be used alone or in the form of a mixture thereof, among which diethyl ether, tetrahydrofuran and dioxane are preferable. The reaction is carried out at a temperature between −20 and 20° C., preferably a temperature between 0 and 5° C., and is completed usually in 30 minutes to 5 hours. As the reducing agent, for example, borane dimethylsulfide complex, borane tetrahydrofuran complex, or the like is used, among which borane dimethylsulfide complex is preferable.

Step 3-3

Compound 3-3 obtained in the step 3-2 is protected by a protective group of a hydroxyl group such as tetrahydropyranyl group, trimethylsilyl group, t-butyldimethylsilyl group, t-butyldiphenylsilyl group, acyl group, methoxymethyl group, or p-methoxybenzyl group, so as to obtain Compound 3-4. The reaction condition at this time is appropriately selected depending on the types of protective group P', and the following condition is preferable. By reacting, in a solvent inactive to the reaction, and in the presence of 1 equivalent to a large excess, preferably 1 to 1.5 equivalents of base, with 1 equivalent to a large excess, preferably 1 to 1.2 equivalents of compound which can be a protective group of hydroxyl group, preferably a silylation agent, Compound 3-4 can be obtained. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which N,N-dimethylformamide is preferable. The reaction is carried out at a temperature between 0 and 50° C., preferably a temperature between 25 and 30° C., and is completed usually in 30 minutes to 20 hours. As the base, for example, imidazole, triethylamine, N,N-dimethylaminopyridine, N,N-diisopropylethylamine, pyridine, or the like is used, among which imidazole is preferable. In the case of introducing a silyl group as the protective group, as a silylation agent, for example, trimethylsilyl chloride, t-butyldimethylsilyl chloride, t-butyldiphenylsilyl chloride, triisopropylsilyl chloride, or the like is used, among which t-butyldimethylsilyl chloride is preferable.

Step 3-4

Compound 3-4 obtained in the step 3-3 is reacted, in a solvent inactive to the reaction, and in the presence of 1 equivalent to a large excess, preferably 1 to 2.2 equivalents of base, with 1 equivalent to a large excess, preferably 1 to 1.2 equivalents of dialkyl disulfide or diaryl disulfide, so as to obtain Compound 3-5. For the solvent inactive to the reaction, any solvent can be employed as long as it is inactive to the reaction, and is not particularly limited. For example, various ethers such as diethyl ether, tetrahydrofuran and dioxane; benzene, toluene, cyclohexane, 1,2-dichloroethane, ethyl acetate, N,N-dimethylformamide, or the like can be used alone or in the form of a mixture thereof, among which diethyl ether, tetrahydrofuran and dioxane are preferable. The reaction is carried out at a temperature between −78 and 50° C., preferably a temperature between −78 and 30° C., and is completed usually in 30 minutes to 5 hours. As the base, for example, lithium diisopropylamide, sodium hydride, sodium hexamethyldisilazide, or the like is used, among which, lithium diisopropylamide and sodium hexamethyldisilazide are preferable. As the dialkyl disulfide or diaryl disulfide, dimethyl disulfide or diphenyl disulfide is preferable.

Step 3-5

Compound 3-5 obtained in the step 3-4 is reacted, in a solvent inactive to the reaction, with 1 equivalent to a large excess, preferably 1 to 5 equivalents of oxidizing agent such as iodine, N-bromosuccinimide, N-chlorosuccinimide, [bis(trifluoroacetoxy)iode]benzene, sodium chlorite or orthoiodoxybenzoic acid, or an alkylating agent such as methyl iodide, ethyl iodide or methyl bromide, so as to obtain Compound 3-6. For the solvent inactive to the reaction, any solvents can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, ethanol, methanol, propanol, acetone, acetonitrile, water, or the like can be used alone or in the form of a mixture thereof, among which acetone, acetonitrile and water are preferable. The reaction is carried out at a temperature between −20 and 30° C., preferably a temperature between 0 and 5° C., and is completed usually in 30 minutes to 5 hours. As the oxidizing agent, for example, iodine or N-bromosuccinimide is preferable, and as the alkylating agent, methyl iodide is preferable. Further, in the case of using N-bromosuccinimide for the reaction, it is desirable to add to the reaction 1 equivalent to a large excess, preferably 1 to 5 equivalents of lutidine and silver nitrate.

Compound of the formula (3-5) which is an intermediate compound in the above General Step-3 can also be synthesized according to the following General Step-4.

General Step-4

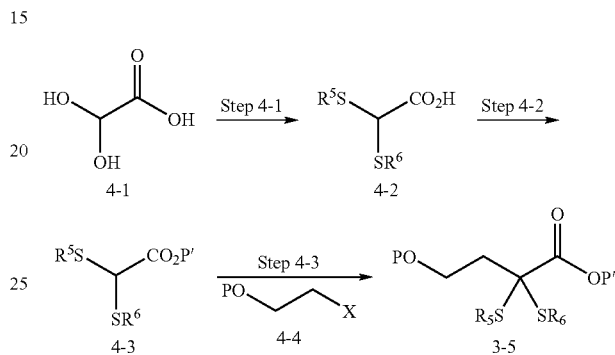

In the formulae, $R^5$, $R^6$, P and P' are as defined above, and X represents a leaving group such as a bromine atom, a chlorine atom, an iodine atom, a tosyloxy group and a mesyloxy group.

Step 4-1

Commercially available glyoxylic acid monohydrate is reacted, in a solvent inactive to the reaction, and in the presence of a catalytic amount to 1 equivalent, preferably 0.1 to 0.5 equivalent of acid, with 1 equivalent to a large excess, preferably 1 to 1.2 equivalents of dithiol (HS—$R^5$—SH) or 2 to 2.2 equivalents of thiol ($R^5$—SH or $R^6$—SH), so as to obtain Compound 4-2. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which toluene is preferable. The reaction is carried out at a temperature between 0 and 200° C., preferably a temperature between 80 and 120° C., and is completed usually in 60 minutes to 3 hours. As the acid, for example, p-toluenesulfonic acid, pyridinium para-toluenesulfonate, diluted hydrochloric acid, diluted sulfuric acid, or the like is used, among which p-toluenesulfonic acid is preferable. As the thiol, for example, ethanethiol, thiophenol, 1,3-propanedithiol, or the like is used, among which 1,3-propanedithiol is preferable.

Step 4-2

Compound 4-2 obtained in the step 4-1 is protected by a protective group of a carboxyl group such as methyl ester, ethyl ester, t-butyl ester or benzyl ester, so as to obtain Compound 4-3. The reaction condition at this time is appropriately selected depending on the types of protective group P', and the following condition is more preferable. Compound 4-2 is reacted, in a solvent inactive to the reaction, and in the presence of 1 equivalent to a large excess, preferably 1 to 1.5 equivalents of base, with 1 equivalent to a large excess, preferably 1 to 5 equivalents of compound which can be a protective group of a carboxyl group, for example, di-t-butyl dicarbonate, so as to obtain Compound 4-3. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, ethanol, methanol, propanol, t-butanol, or the like can be used alone or in the form of a mixture thereof, among which toluene and t-butanol are preferable. The reaction is carried out at a temperature between 0 and 100° C., preferably a temperature between 5 and 50° C., and is completed usually in 30 minutes to 30 hours. As the base, for example, imidazole, triethylamine, N,N-dimethylaminopyridine, N,N-diisopropylethylamine, pyridine, or the like is used, among which N,N-dimethylaminopyridine is preferable.

Step 4-3

Compound 4-3 obtained in the step 4-2 is reacted, in a solvent inactive to the reaction, and in the presence of 1 equivalent to a large excess, preferably 1 to 1.2 equivalents of base, with 1 equivalent to a large excess, preferably 1 to 1.2 equivalents of Compound 4-4, so as to obtain Compound 3-5. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, N,N-dimethylformamide, dimethyl sulfoxide, methylene chloride, chloroform, or the like can be used alone or in the form of a mixture thereof, among which toluene is preferable. The reaction is carried out at a temperature between −20 and 50° C., preferably a temperature between 0 and 30° C., and is completed usually in 30 minutes to 10 hours. As the base, for example, sodium hydride, potassium hydride, lithium diisopropylamide, or the like is used, among which sodium hydride is preferable. Compound 4-4 may be a commercially available product, or can be obtained by appropriately protecting a corresponding commercially available alcohol form with a protective group P. In Compound 4-4, as the P, t-butyldiphenylsilyl group, t-butyldimethylsilyl group and tetrahydropyranyl group are preferable, and t-butyldimethylsilyl group is further preferable. Further, as X, a bromine atom and a chlorine atom are preferable, and a bromine atom is particularly preferable.

In the process for the synthesis of the compound of the formula (3-6) from the compound of the formula (5-5) mentioned above in 2), this compound of the formula (5-5) can be, starting from the compound of the formula (5-1), synthesized according to the following steps, so that the compound of the formula (3-6) can be finally obtained (General Preparation Process-5).

General Preparation Process-5

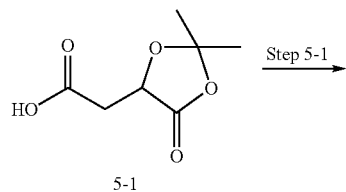

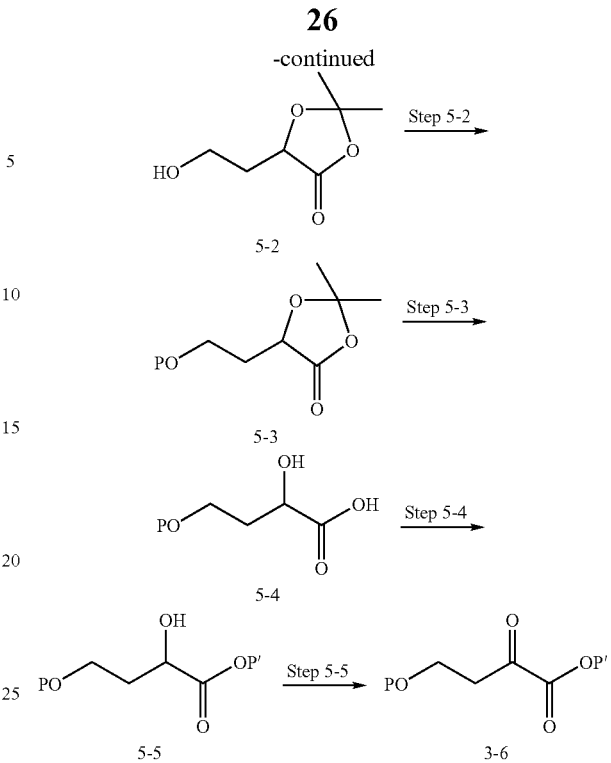

In the formulae, P and P' are as defined above.

Step 5-1

Compound 5-1 (synthesized according to the process described in Account of Chemical Research, 2002, 35, 774) is reacted, in a solvent inactive to the reaction, and in the presence of 1 equivalent to a large excess, preferably 1 to 1.5 equivalents of Lewis acid, with 1 equivalent to a large excess, preferably 1 to 1.5 equivalents of reducing agent, so as to obtain Compound 5-2. As the reducing agent, borane dimethyl sulfide complex, borane tetrahydrofuran complex, or the like is used, among which borane dimethyl sulfide complex is preferable. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, or the like can be used alone or in the form of a mixture thereof, among which diethyl ether, tetrahydrofuran and dioxane are preferable. The reaction is carried out at a temperature between −20 and 30° C., preferably a temperature between 0 and 5° C., and is completed usually in 60 minutes to 20 hours. As the Lewis acid, for example, trimethoxyboronic acid is used.

Step 5-2

Compound 5-2 obtained in the step 5-1 is protected by a protective group of a hydroxyl group such as tetrahydropyranyl group, trimethylsilyl group, t-butyldimethylsilyl group, t-butyldiphenylsilyl group, acyl group, methoxymethyl group, p-methoxybenzyl group, or benzyl group, so as to obtain Compound 5-3. The reaction condition at this time is appropriately selected depending on the types of protective group P, and the following condition is preferable. By reacting, in a solvent inactive to the reaction, and in the presence of 1 equivalent to a large excess, preferably 1 to 1.5 equivalents of base, with 1 equivalent to a large excess, preferably 1 to 1.2 equivalents of compound which can be a protective group of hydroxyl group, for example, a silylation agent, Compound 5-3 can be obtained. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which N,N-dimethylformamide is preferable. The reaction is carried out at a temperature between 0 and 50° C., preferably a temperature between 25 and 30° C., and is completed usually in 30 minutes to 20 hours. As the base, for example, imidazole, triethylamine, N,N-dimethylaminopyridine, N,N-diisopropylethylamine, pyridine, sodium hydride, potassium hydride, potassium carbonate, 2,6-lutidine, 1,4-diazabicyclo[2,2,2]octane, potassium-t-butoxide, potassium-hexamethyldisilazide, or the like is used, among which imidazole is preferable. In the case of protecting a hydroxyl group with a silyl group, as a silylation agent, for example, chlorotrimethylsilane, N,N-bis(trimethylsilyl)urea, trimethylsilylnitrile, t-butyldimethylchlorosilane, t-butyldiphenylchlorosilane, t-butyldimethylsilylnitrile, t-butyldimethyltrifluoromethanesulfonate, or the like is used, among which t-butyldiphenylchlorosilane is preferable.

Step 5-3

Compound 5-3 obtained in the step 5-2 is reacted, in a solvent inactive to the reaction, with a catalytic amount to a large excess, preferably 1 to 3 equivalents of acid or base, so as to obtain Compound 5-4. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, ethanol, methanol, propanol, t-butanol, acetonitrile, water, or the like can be used alone or in the form of a mixture thereof, among which t-butanol and toluene are preferable. The reaction is carried out at a temperature between −20 and 30° C., preferably a temperature between 0 and 5° C., and is completed usually in 15 minutes to 1 hour. As the acid or base, for example, acetic acid, formic acid, citric acid, p-toluenesulfonic acid, pyridinium-p-toluenesulfonate, sodium-t-butoxide, potassium-t-butoxide, sodium hydroxide, lithium hydroxide, or the like is used, among which sodium-t-butoxide and lithium hydroxide are preferable.

Step 5-4

Compound 5-4 obtained in the step 5-3 is protected by a protective group of a carboxyl group such as methyl ester, ethyl ester, t-butyl ester, or benzyl ester, so as to obtain Compound 5-5. The reaction condition at this time is appropriately selected depending on the types of protective group P', and the following condition is more preferable. Compound 5-4 obtained in the step 5-3 is reacted, in a solvent inactive to the reaction, and in the presence of 1 equivalent to a large excess, preferably a large excess of base, with 1 equivalent to a large excess, preferably a large excess of a compound which can be a protective group of carboxyl group, for example, t-butyl bromide, so as to obtain Compound 5-5. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, N,N-dimethylformamide, dimethyl sulfoxide, methylene chloride, chloroform, t-butanol, acetonitrile, or the like can be used alone or in the form of a mixture thereof, among which t-butanol and toluene are preferable. The reaction is carried out at a temperature between 0 and 100° C., preferably a temperature between 40 and 70° C., and is completed usually in 30 minutes to 30 hours. As the base, for example, lithium hydroxide, tetrabutylammonium chloride, sodium hydroxide, potassium hydroxide, potassium carbonate, N,N-diisopropylethylamine, potassium-hexamethyldisilazide, or the like is used, among which potassium carbonate and potassium hydroxide are preferable.

Step 5-5

The hydroxyl group of Compound 5-5 obtained in the step 5-4 is reacted, in a solvent inactive to the reaction, with 1 equivalent to a large excess, preferably 1 to 1.2 equivalents of oxidizing agent, so as to obtain Compound 3-6. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, acetone, pyridine, t-butanol, water, or the like can be used alone or in the form of a mixture thereof, among which acetone is preferable. The reaction is carried out at a temperature between −20 and 50° C., preferably a temperature between 0 and 30° C., and is completed usually in 30 minutes to 30 hours. As the oxidizing agent, for example, a combination of iodobenzene diacetate and 4-acetamide-2,2,6,6-tetramethylpiperidine 1-oxyl or 2,2,6,6-tetramethylpiperidine 1-oxyl, chromic acid-sulfuric acid (Jones reagent), 1,1,1-tris(acetyloxy)-1,1-dihydro-1,2-benziodoxol-3-(1H)-one (Dess-Martin reagent), sodium chlorite-sodium dihydrogenphosphate-2-methyl-2-butene, oxalyl chloride-dimethyl sulfoxide-triethylamine, pyridinium-chlorochromate, pyridinium-dichromate, N-bromosuccinimide-pyridine, sodium bromite, sulfur trioxide pyridine complex, sodium tungstate, tetrabutylammonium pertenate, or the like is used, among which a combination of iodobenzene diacetate and 4-acetamide-2,2,6,6-tetramethylpiperidine 1-oxyl or 2,2,6,6-tetramethylpiperidine 1-oxyl, and 1,1,1-tris(acetyloxy)-1,1-dihydro-1,2-benziodoxol-3-(1H)-one (Dess-Martin reagent) are preferable.

Further, in the process for the synthesis of the compound of the formula (3-6) from the compound of the formula (3-1) mentioned above in 1), the compound of the formula (3-4) which is an intermediate compound can also be synthesized, starting from the compound of the formula (6-1), according to the following step (General Step-6).

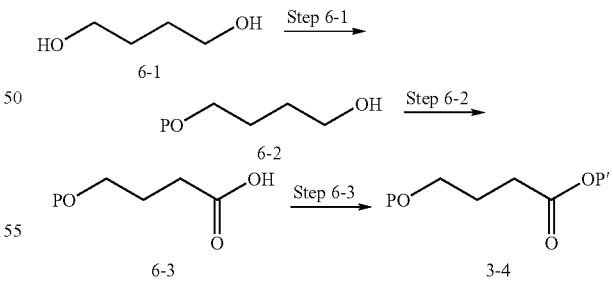

In the formulae, P and P' are as defined above.

Step 6-1

Commercially available 1,4-butanediol is protected by a protective group of a hydroxyl group such as tetrahydropyranyl group, trimethylsilyl group, t-butyldimethylsilyl group, t-butyldiphenylsilyl group, acyl group, methoxymethyl group, p-methoxybenzyl group or benzyl group, so as to obtain Compound 6-2. The reaction condition at this time is appropriately selected depending on the types of protective group P, and the following condition is preferable. By reacting, in a solvent inactive to the reaction, and in the presence of 1 equivalent to a large excess, preferably 1 to 1.5 equivalents of base, with 1 equivalent to a large excess, preferably 1 to 1.2 equivalents of compound which can be a protective group of hydroxyl group, for example, a silylation agent, Compound 6-2 can be obtained. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which N,N-dimethylformamide is preferable. The reaction is carried out at a temperature between 0 and 50° C., preferably a temperature between 25 and 30° C., and is completed usually in 30 minutes to 20 hours. As the base, for example, imidazole, triethylamine, N,N-dimethylaminopyridine, N,N-diisopropylethylamine, pyridine, sodium hydride, or the like is used, among which diisopropylethylamine is preferable. In the case of protecting a hydroxyl group with a silyl group, as a silylation agent, for example, trimethylsilyl chloride, t-butyldimethylsilyl chloride, t-butyldiphenylsilyl chloride, or the like is used, among which t-butyldimethylsilyl chloride and t-butyldiphenylsilyl chloride are preferable.

Step 6-2

Compound 6-2 obtained in the step 6-1 is reacted, in a solvent inactive to the reaction, with 1 equivalent to a large excess, preferably 1 to 2.4 equivalents of oxidizing agent, so as to obtain Compound 6-3. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, acetone, or the like can be used alone or in the form of a mixture thereof, among which acetone is preferable. The reaction is carried out at a temperature between −20 and 30° C., preferably a temperature between 0 and 30° C., and is completed usually in 30 minutes to 10 hours. As the oxidizing agent, for example, iodobenzene diacetate, N-chlorosuccinimide, trichloroisocyanuric acid, or the like is used, among which trichloroisocyanuric acid is preferable.

Step 6-3

Compound 6-3 obtained in the step 6-2 is protected by a protective group of a carboxyl group such as methyl ester, ethyl ester, t-butyl ester or benzyl ester, so as to obtain Compound 3-4. The reaction condition at this time is appropriately selected depending on the types of protective group P', and the following condition is more preferable. Compound 6-3 is reacted with 1 equivalent to a large excess, preferably 1 to 5 equivalents of compound which can be a protective group of a carboxyl group, for example, dimethylformamide-di-t-butylacetal so as to obtain Compound 3-4. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, or the like can be used alone or in the form of a mixture thereof, among which toluene and benzene are preferable. The reaction is carried out at a temperature between 0 and 100° C., preferably a temperature between 5 and 50° C., and is completed usually in 30 minutes to 30 hours.

Compound of the formula (7-1) of the present invention can be synthesized by means of a process comprising a step of reacting the compound represented by the formula (I-8) which was synthesized according to the process mentioned above with the compound represented by the formula (3-6) in the presence of a base. Further, from the compound of the formula (7-1) which was synthesized according to the present process, the compound of the formula (7-6) which is a desired compound can be synthesized according to the following steps (General Preparation Process-7).

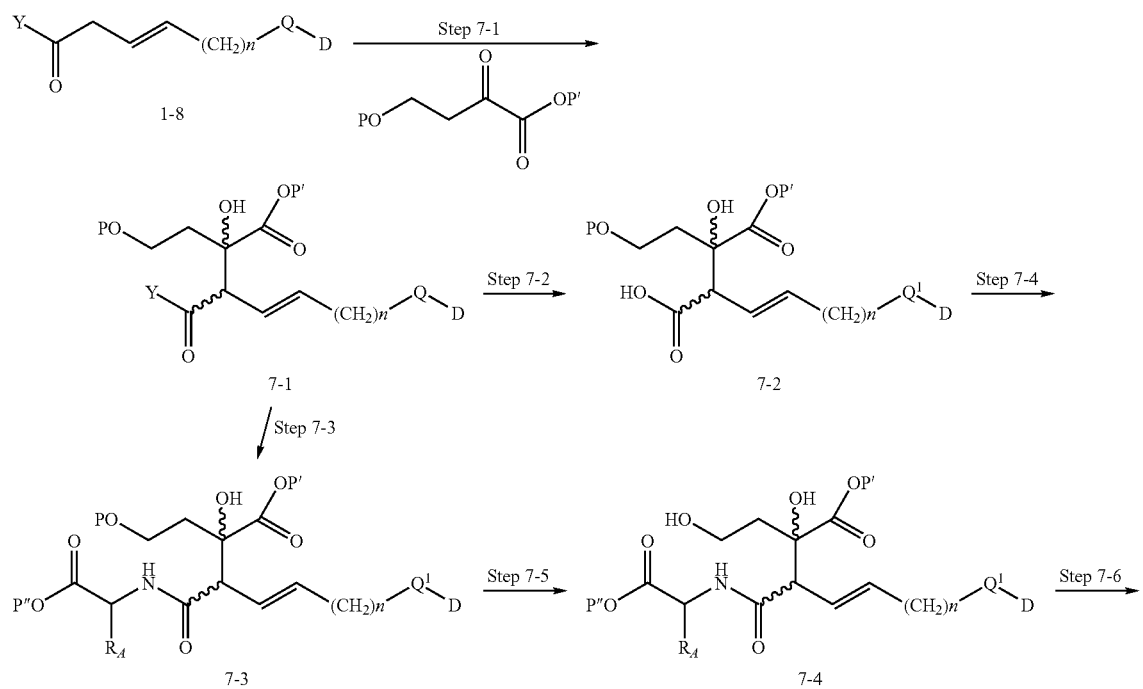

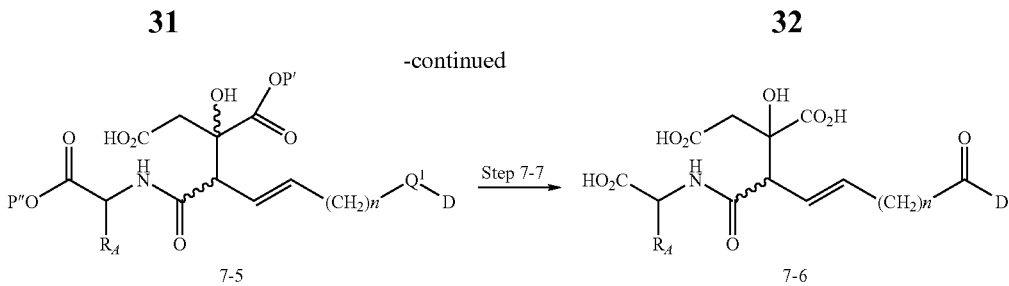

In the formulae, Y, n, D, P, P' and $R_A$ are as defined above, P'' is a protective group of a carboxyl group, and Q is a protected carbonyl group. Further, Q' is a carbonyl group, or a protected carbonyl group, preferably represents the following groups.

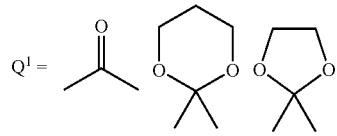

General Preparation Process-7
Step 7-1

Compound 1-8 obtained in the step 1-8 of General Step-1 mentioned above is reacted, in a solvent inactive to the reaction, and in the presence of 1 equivalent to a large excess, preferably 1 to 1.2 equivalents of base, with 1 equivalent to a large excess, preferably 1 to 1.2 equivalents of Compound 3-6, so as to obtain Compound 7-1. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, N,N-dimethylformamide, or the like can be used alone or in the form of a mixture thereof, among which tetrahydrofuran and toluene are preferable. The reaction is carried out at a temperature between −78 and 0° C., preferably a temperature between −78 and −25° C., and is completed usually in 30 minutes to 10 hours. As the base, for example, lithium hexamethyldisilazide, lithium diisopropylamide, or the like is used, among which lithium hexamethyldisilazide is preferable. While the present step proceeds in the absence or presence of lithium chloride, the stereoselectivity of the obtained compound 7-1 is higher in the presence of lithium chloride. Therefore, it is preferable to allow the present step to proceed in the presence of 1 to 4 equivalents of lithium chloride with respect to Compound 1-8.

Step 7-2

Compound 7-1 obtained in the step 7-1 is reacted, in a solvent inactive to the reaction, with 1 equivalent to a large excess, preferably 1 to 5 equivalents of base, so as to obtain Compound 7-2. For the solvent inactive to the reaction, any solvent can be employed as long as it is inactive to the reaction, and is not particularly limited. However, for example, tetrahydrofuran, dioxane, N,N-dimethylformamide, acetonitrile, ethanol, methanol, propanol, water, or the like can be used alone or in the form of a mixture thereof, among which hydrous tetrahydrofuran, hydrous acetonitrile and hydrous dioxane are preferable. The reaction is carried out at a temperature between −10 and 50° C., preferably a temperature between 0 and 5° C., and is completed usually in 30 minutes to 5 hours. As the base, for example, lithium hydroxide, tetrabutylammonium chloride, sodium hydroxide, potassium hydroxide, potassium carbonate, or the like is used in the presence or absence of hydrogen peroxide solution, among which lithium hydroxide is preferable.

Step 7-3

Compound 7-1 obtained in the step 7-1 is reacted, in a solvent inactive to the reaction, and in the presence of 1 equivalent to a large excess, preferably 1 to 3 equivalents of base, with 1 equivalent to a large excess, preferably 1 to 1.2 equivalents of an amino acid compound having a desired group $R_A$, so as to obtain Compound 7-3 without going through the steps 7-2 and 7-4. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, acetonitrile, or the like can be used alone or in the form of a mixture thereof, among which acetonitrile is preferable. The reaction is carried out at a temperature between 0 and 100° C., preferably a temperature between 30 and 60° C., and is completed usually in 24 hours to 144 hours. As the base, for example, triethylamine, N,N-dimethylaminopyridine, N,N-diisopropylethylamine, pyridine, or the like is used, among which diisopropylethylamine and triethylamine are preferable. Further, the amino acid compound used herein can be synthesized, for example, according to the processes mentioned hereinafter in General Step-8 and General Step-9.

Step 7-4

Compound 7-2 obtained in the step 7-2 is reacted, in a solvent inactive to the reaction, in the presence of 1 equivalent to a large excess, preferably 1 to 1.5 equivalents of base, and in the presence of 1 equivalent to a large excess, preferably 1 to 1.5 equivalents of amidating agent, with 1 equivalent to a large excess, preferably 1 to 1.5 equivalents of amino acid compound having a desired group $R_A$, so as to obtain Compound 7-3. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, acetonitrile, or the like can be used alone or in the form of a mixture thereof, among which N,N-dimethylformamide is preferable. The reaction is carried out at a temperature between 0 and 50° C., preferably a temperature between 0 and 30° C., and is completed usually in 30 minutes to 5 hours. As the base, for example, triethylamine, N,N-dimethylaminopyridine, N,N-diisopropylethylamine, pyridine, or the like is used, among which N,N-diisopropylethylamine is preferable. As the amidating agent, for example, O-(7-azabenzotriazol-1-yl)-N,N,N',N'-tetramethyluronium hexafluorophosphate, 4-(4,6-dimethoxy-1,3,5-triazin-2-yl)-4-methylmorpholinium chloride, water-soluble carbodiimide hydrochloride (WSC.HCl) or dicyclocarbodiimide, and 1-hydroxybenzotriazole (HOBt), etc. can be used.

Step 7-5

Compound 7-3 obtained in the step 7-3 or 7-4 is deprotected by a deprotecting agent of a hydroxyl group, so as to obtain Compound 7-4. The reaction condition at this time is appropriately selected depending on the types of protective groups P and $Q^1$. In the case where the protecting group P is a silyl group, Compound 7-3 obtained in the step 7-3 or 7-4 is reacted, in a solvent inactive to the reaction, with 1 equivalent to a large excess, preferably 1 to 1.5 equivalents of desilylation agent, so as to obtain Compound 7-4. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, ethanol, methanol, propanol, acetonitrile, or the like can be used alone or in the form of a mixture thereof, among which tetrahydrofuran, acetonitrile, acetone and t-butanol are preferable. The reaction is carried out at a temperature between 0 and 50° C., preferably a temperature between 0 and 30° C., and is completed usually in 15 minutes to 5 hours. In the case where the protecting group is a silyl group, as the desilylation agent, for example, a combination of tetrabutylammonium fluoride and acetic acid, aqueous p-toluenesulfonic acid solution, aqueous citric acid solution, hydrochloric acid, aqueous acetic acid solution, or the like is used, among which a combination of tetrabutylammonium fluoride and acetic acid and aqueous citric acid solution are preferable. When the present reaction is carried out under acidic conditions such as aqueous p-toluenesulfonic acid solution, aqueous citric acid solution, hydrochloric acid and aqueous acetic acid solution, in the case where $Q^1$ is a protected carbonyl group, $Q^1$ is deprotected and sometimes converted to a carbonyl group. The compound in which $Q^1$ is converted to a carbonyl group may be subsequently subjected to the step 7-6 as it is, or after converted again to a protected carbonyl group as it is or by means of a well known method.

Step 7-6

Compound 7-4 obtained in the step 7-5 is reacted, in a solvent inactive to the reaction, with 1 equivalent to a large excess, preferably 1 to 1.5 equivalents of oxidizing agent, so as to obtain Compound 7-5. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, water, or the like can be used alone or in the form of a mixture thereof, among which hydrous acetonitrile, hydrous or anhydrous methylene chloride, hydrous acetone and hydrous t-butanol are preferable. The reaction is carried out at a temperature between −78 and 30° C., preferably a temperature between 0 and 30° C., and is completed usually in 30 minutes to 20 hours. For the oxidizing agent, for example, a combination of iodobenzene diacetate and 4-acetamide-2,2,6,6-tetramethylpiperidine 1-oxyl or 2,2,6,6-tetramethylpiperidine 1-oxyl, chromic acid-sulfuric acid (Jones reagent), 1,1,1-tris(acetyloxy)-1,1-dihydro-1,2-benziodoxol-3-(1H)-one (Dess-Martin reagent) followed by sodium chlorite-sodium dihydrogenphosphate-2-methyl-2-butene, oxalyl chloride-dimethyl sulfoxide-triethylamine followed by sodium chlorite-sodium dihydrogenphosphate-2-methyl-2-butene, or the like is used, among which a combination of iodobenzene diacetate and 4-acetamide-2,2,6,6-tetramethylpiperidine 1-oxyl or 2,2,6,6-tetramethylpiperidine 1-oxyl is preferable.

Step 7-7

Compound 7-5 obtained in the step 7-6 is deprotected by a deprotecting agent of a carboxyl group, so as to obtain Compound 7-6. The reaction condition at this time is appropriately selected depending on the types of protective groups P''', and the following condition is preferable. Compound 7-5 is reacted in a solvent inactive to the reaction, with 1 equivalent to a large excess, preferably 1 to 5 equivalents of acid, so as to obtain Compound 7-6. For the solvent inactive to the reaction, any solvent can be employed as long as it is inactive to the reaction, and is not particularly limited. However, for example, various ethers such as diethyl ether, tetrahydrofuran and dioxane; benzene, toluene, cyclohexane, 1,2-dichloroethane, ethyl acetate, N,N-dimethylformamide, dimethyl sulfoxide, methylene chloride, chloroform, ethanol, methanol, propanol, acetonitrile, water, or the like can be used alone or in the form of a mixture thereof, among which hydrous methylene chloride and hydrous toluene are preferable. The reaction is carried out at a temperature between −20 and 90° C., preferably a temperature between 0 and 30° C., and is completed usually in 15 minutes to 5 hours. As the acid, for example, trifluoroacetic acid-anisole, formic acid, acetic acid-hydrochloric acid or hydrobromic acid, p-toluenesulfonic acid, trifluoromethanesulfonic acid, boron trifluoride etherate, or the like is used, among which trifluoroacetic acid is preferable.

The following General Preparation Process-8 and General Preparation Process-9 describe examples of the process for the synthesis of specific amino acid compounds (8-4) and (9-3) out of the amino acid compounds having a desired group $R_A$ used in the previously mentioned step 7-3 or 7-4.

General Preparation Process-8

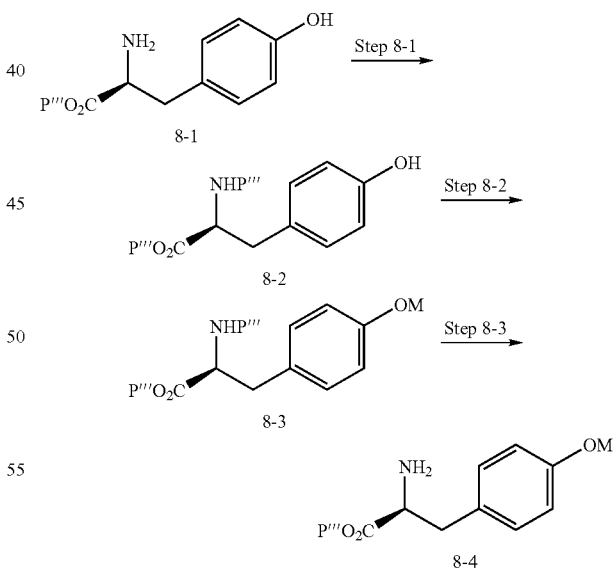

In the above formulae, P''' represents a protective group of a carboxyl group; P'''' represents a protective group of an amino group; M represents a desired linear or branched alkyl group which may be substituted, linear or branched alkynyl group which may be substituted, linear or branched alkenyl group which may be substituted, or cycloalkyl group which may be substituted.

Step 8-1

Compound 8-1 is commercially available (L-tyrosine-t-butyl ester, manufactured by Aldrich, Inc.) or a compound which can be easily synthesized from a commercially available compound. This compound is protected by a protective group of an amino group such as acetyl, trifluoroacetyl, t-butoxycarbonyl, benzyloxycarbonyl or 9-fluorenylmethylcarbonyl, so as to obtain Compound 8-2. For the reaction condition at this time, the condition for deprotection of the protective group P'''' of a carboxyl group as described in "Protective Groups in Organic Synthesis, Theodora Greene (authored), 1999, Wiley-Interscience" is used.

Step 8-2

Compound 8-2 is reacted, in a solvent such as diethyl ether, toluene, cyclohexane, acetone, dimethylformamide, dioxane, ethyl acetate or dimethyl sulfoxide, or in a mixed solvent thereof, and in the presence of a base such as potassium carbonate, sodium hydroxide or sodium hydride, with the above-defined M bonded to a leaving group such as a halogen atom or mesylate or tosylate, at room temperature or under heating, preferably at room temperature, so as to obtain Compound 8-3 with the desired group M being introduced. Otherwise, Compound 8-3 can also be obtained by reacting Compound 8-2 with the above-defined M substituted by a hydroxyl group in the condition of Mitsunobu reaction.

Step 8-3

Compound 8-4 can be obtained by deprotecting the protective group P'''' of an amino group in Compound 8-3. For the reaction condition at this time, the condition for deprotection of the protective group P'''' of an amino group as described in "Protective Groups in Organic Synthesis, Theodora Greene (authored), 1999, Wiley-Interscience" is used.

General Preparation Process-9

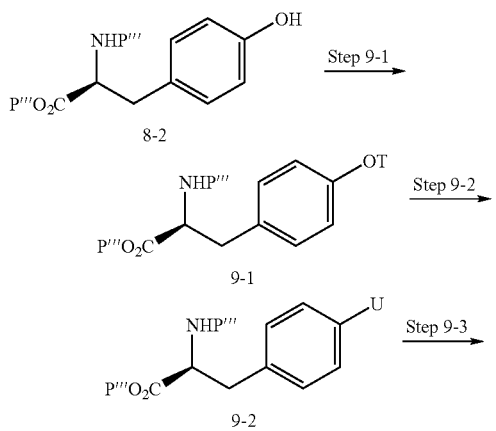

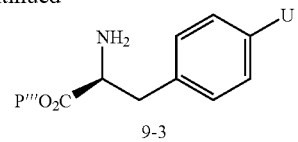

In the above formulae, P''' represents a protective group of a carboxyl group; P'''' represents a protective group of an amino group; T represents a leaving group such as mesylate, toluenesulfonate, or trifluoromethanesulfonate; and U represents an aryl group which may be substituted or a heteroaryl group which may be substituted.

Step 9-1

Compound 8-2 obtained in the step 8-1 is reacted, in various solvents such as diethyl ether, toluene, cyclohexane, acetone, dimethylformamide, dioxane, ethyl acetate, dimethyl sulfoxide, and dichloromethane, or in a mixed solvent thereof, and in the presence of a base such as N,N-diisopropylethylamine, triethylamine, pyridine, or 4-N,N-dimethylaminopyridine, with a compound which can be a leaving group such as methanesulfonic acid chloride, toluenesulfonic acid chloride, or trifluoromethanesulfonic acid anhydride, at room temperature or under cooling, preferably under cooling, so as to obtain Compound 9-1 with a leaving group T being introduced.

Step 9-2

Compound 9-1 is reacted, in various solvents such as diethyl ether, toluene, benzene, dimethylformamide, dioxane, ethyl acetate, acetonitrile or water, or in a mixed solvent thereof, and in the presence of a palladium catalyst such as palladium diacetate or tetrakistriphenylphosphine palladium, with an aryl or heteroaryl boronic acid derivative, or an aryl or heteroaryl boronic acid ester derivative, etc. having a desired aryl group or heteroaryl group, at room temperature or under hating, preferably under heating so as to obtain Compound 9-2.

Step 9-3

Compound 9-3 can be obtained by deprotecting the protective group P'''' of an amino group in Compound 9-2. For the reaction condition at this time, the condition for deprotection of the protective group P'''' of an amino group as described in "Protective Groups in Organic Synthesis, Theodora Greene (authored), 1999, Wiley-Interscience" is used.

EXAMPLES

The following examples illustrate the present invention in detail, but do not limit the present invention.

Example 1

Synthesis of Compound 7

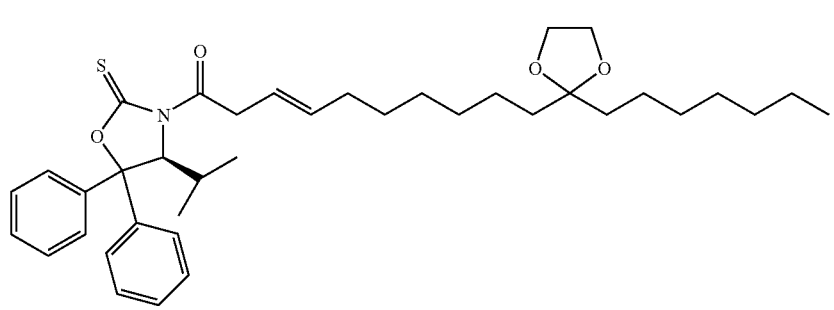

1-1 (Step 1-1):

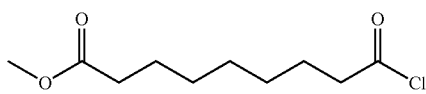

1

Azelaic acid monomethyl ester (14.8 g, 73.2 mmol) was dissolved in toluene (74 mL), DMF (57 μL, 0.732 mmol) was added, cooled with ice under a nitrogen atmosphere, and oxalyl dichloride (19.1 mL, 220 mmol) was added dropwise over 5 minutes. After completion of the dropwise addition, an ice cooler was removed, followed by stirring for 3 hours at room temperature. Toluene and oxalyl dichloride were distilled off with an evaporator, and subsequently toluene (74 mL) was added again to distill off the solvent. The whole amount of the crude product 1 was used directly for the next reaction.

1-2 (Step 1-2):

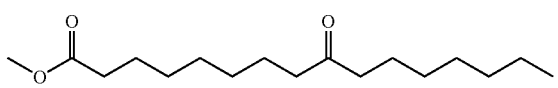

2

The above crude product 1 was dissolved in tetrahydrofuran (74 mL), 0.05 equivalent of tris(2,4-pentanedionato)iron (III) was added, cooled to −15° C., and subsequently 1 mol/L tetrahydrofuran solution of n-heptylmagnesium bromide (87.8 mL) was added dropwise over 1 hour. After the completion of the dropwise addition, a cooler was removed, followed by stirring for 1 hour at room temperature. 0.5 N aqueous hydrochloric acid solution (74 mL) was added to the reaction solution to stop the reaction, and the aqueous layer was extracted with ethyl acetate (74 mL). The organic layers were combined, washed sequentially with water (74 mL), a saturated aqueous sodium bicarbonate (74 mL), brine (74 mL), and dried over anhydrous magnesium sulfate, followed by filtration and distilling off of the solvents to obtain Compound 2 (22.0 g) as an orange solid. Purification by column chromatography afforded Compound 2 with a yield of 90%.

Physicochemical Property of Compound 2

$^1$H-NMR (400 MHz, CDCl$_3$): δ 0.88 (t, J=6.8 Hz, 3H), 1.21-1.37 (m, 14H), 1.50-1.75 (m, 6H), 2.30 (t, J=7.6 Hz, 2H), 2.40 (t, J=7.6 Hz, 4H), 3.63 (s, 3H).

MS (EI): m/z (rel int) 284 (10 [M+]), 253 (25), 209 (58), 142 (100), 127 (65), 57 (92)

1-3 (Step 1-2):

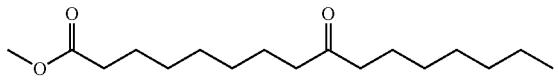

2

To a suspension of copper iodide (Kanto Chemical Co., Inc., purity 99%, 41.26 g, 216.6 mmol) in tetrahydrofuran (570 mL), heptylmagnesium bromide (Aldrich, 1M ethyl ether solution, 211 mL, 211 mmol) was added dropwise at 0° C. over 30 minutes, and subsequently stirred at the same temperature for 20 minutes. This deep purple-colored reaction mixture was cooled to −78° C., and tetrahydrofuran solution (40 mL) of Compound 1 (27.6 g) synthesized in the above step 1-1 was added dropwise over 10 minutes, followed by raising the temperature from −78 to 0° C. over 1 hour and stirring at 0° C. for 45 minutes. 1N aqueous hydrochloric acid solution (87 mL)-water (87 mL) was added to the reaction mixture at 0° C., diluted with ethyl ether, and filtered through celite. The filtrate was adjusted to pH 7 with a saturated aqueous sodium hydrogencarbonate solution, and the ethyl ether layer was dried over magnesium sulfate. Subsequently, the solvent was distilled off, and the residue was purified by flash chromatography to obtain Compound 2 (33.34 g, 94%) as a colorless solid.

1-4 (Step 1-3)

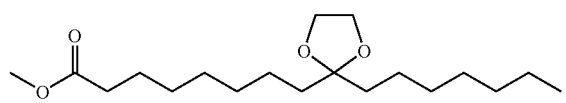

3

The crude product (11.0 g, 36.6 mmol) of Compound 2 was dissolved in toluene (110 mL), 3 equivalents of ethylene glycol (6.1 mL, 110 mmol) and 0.1 equivalent of p-toluenesulfonic acid were added, which was heated under reflux for 16 hours while performing azeotropical removal of water. After cooled to room temperature, saturated aqueous sodium bicarbonate solution (33 mL) was added to stop the reaction, and the aqueous layer was extracted with ethyl acetate (33 mL). The organic layers were combined, washed with brine, and dried over anhydrous magnesium sulfate, followed by filtration and distilling off of the solvents to obtain Compound 3 (14.2 g) as an orange oil. Purification by column chromatography afforded the desired substance with a yield of 87%.

Physicochemical Property of Compound 3

$^1$H-NMR (400 MHz, CDCl$_3$): δ 0.88 (t, J=6.8 Hz, 3H), 1.21-1.39 (m, 18H), 1.50-1.71 (m, 6H), 2.30 (t, J=7.6 Hz, 2H), 3.67 (s, 3H), 3.92 (s, 4H).

MS (EI): m/z (rel int) 297 (8), 229 (95), 171 (100)

1-5 (Step 1-4)

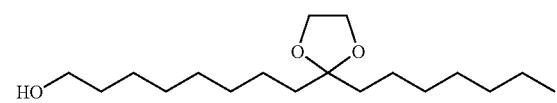

4

Lithium aluminium hydride (1.81 g, 47.6 mmol) was suspended in tetrahydrofuran (71 mL), and a solution of the crude product (14.2 g, 36.6 mmol) of Compound 3 in tetrahydrofuran (28.4 mL) was added to the suspension dropwise under ice cooling over 10 minutes. After stirring for 20 minutes under ice cooling, 1N aqueous sodium hydroxide solution (6 mL) was added dropwise at the same temperature to stop the reaction, and anhydrous magnesium sulfate (12 g) was added. After the reaction solution was stirred at room temperature until it becomes a slurry shape, celite filtration was performed, and the celite was washed with ethyl acetate (200 mL).

Subsequently, the solvents of the filtrate were distilled off, to obtain Compound 4 (12.2 g) as a pale yellow oil.

Purification by column chromatography afforded the desired substance with a yield of 96%.

Physicochemical Property of Compound 4

$^1$H-NMR (400 MHz, CDCl$_3$): δ 0.88 (t, J=6.8 Hz, 3H), 1.14-1.43 (m, 21H), 1.50-1.64 (m, 6H), 3.64 (dt, J=6.4, 5.6 Hz, 2H), 3.92 (s, 4H).

MS (EI): m/z (rel int) 299 ([0.7M-]), 200 (100), 171 (100)

1-6 (Step 1-5)

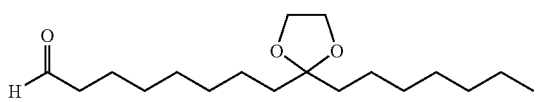

5

The crude product of Compound 4 (12.2 g, 36.6 mmol) was dissolved in toluene (61 mL), followed by the addition of 28.5 mg (0.183 mmol) of 2,2,6,6-tetramethylpiperidinyloxy free radical (TEMPO reagent) and 1 equivalent of 5% aqueous sodium bicarbonate solution (61 mL, 36.9 mmol), and 1 equivalent of sodium hypochlorite (12%, 22.7 mL, 36.6 mmol) was added dropwise over 25 minutes with ice cooling of the reaction solution. After the completion of the dropwise addition, an ice cooler was removed, stirred at room temperature for 1 hour, and left to stand for a while to separate the organic layers. The aqueous layer was extracted with ethyl acetate (80 mL×2), and the organic layers were combined, and washed with water (80 mL) and brine, followed by drying over anhydrous magnesium sulfate, filtration and distilling off of the solvents to obtain 12.6 g of 8-(2-heptyl-[1,3]dioxolan-2-yl)-octanal (5) as an orange oil. Purification by column chromatography afforded the desired substance with a yield of 80%.

Physicochemical Property of Compound 5

$^1$H-NMR (400 MHz, CDCl$_3$): δ 0.88 (t, J=6.8 Hz, 3H), 1.20-1.40 (m, 18H), 1.52-1.70 (m, 6H), 2.41 (dt, J=7.2, 2 Hz, 2H), 3.92 (s, 4H), 9.76 (t, J=2 Hz, 1H).

MS (EI): m/z (rel int) 298 (20 [M+]), 223 (25), 200 (100), 171 (100)

1-7 (Step 1-6)

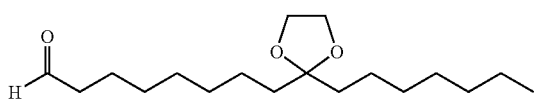

5

To a toluene (489 mL) solution of Compound 3 (37.61 g, 114.5 mmol), diisobutylaluminium hydride (1.01 M toluene solution, 122 mL, 123 mmol) was added dropwise over 1 hour at −78° C., followed by stirring at −78° C. for 30 minutes. Methanol (19.2 mL) was added to the reaction solution at −78° C. and stirred for 5 minutes, and subsequently the resulting reaction mixture was poured into a mixed solution of a saturated aqueous Rochelle salt solution (93 mL) and water (276 mL) under ice cooling, followed by stirring for 1 hour under ice cooling. The reaction mixture was filtered through celite, and the filtered reaction mixture was extracted with ether (3×600 mL). After the filtrate and the extract were washed sequentially with water (280 mL), and were combined. After drying of the organic layer over MgSO$_4$, the solvents were distilled off, and the residue was purified by flash chromatography to obtain Compound 5 (31.5 g, 92%) as a colorless oily substance.

1-8 (Step 1-7)

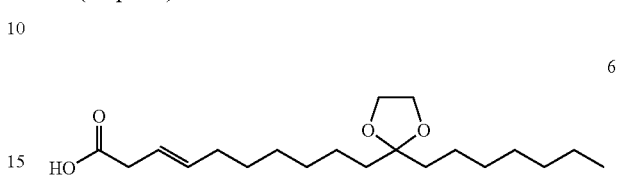

6

The crude product of Compound 5 (12.6 g, 36.6 mmol) was dissolved in toluene (63 mL), followed by the addition of triethylamine (5.6 mL, 40.3 mmol) and malonic acid (4.0 g, 38.4 mmol), and was heated with reflux overnight. The reaction solution was cooled to room temperature, and 5% aqueous citric acid solution (63 mL) was added to stop the reaction. After the separation of the organic layer, the aqueous layer was extracted with ethyl acetate (63 mL), and the organic layers were combined, and washed with water (63 mL) and brine, followed by drying over anhydrous magnesium sulfate, filtration and distilling off of the solvents to obtain 12.1 g of a crude product of Compound 6 as an orange oil. 1.04 g (3.13 mmol) of this crude product was dissolved in acetonitrile (10 mL), followed by the addition of hexane (10 mL) and 5% sodium bicarbonate water (10 mL), stirred vigorously and left to stand, to be separated into three layers. Acetonitrile layer of the intermediate layer and aqueous layer of the lower layer were taken out, and washed again with hexane (10 mL). After adjusting the acetonitrile layer and aqueous layer to pH 4 with a 5% aqueous sodium hydrogensulfate solution (20 mL), the aqueous layer was separated, and this aqueous layer was extracted with ethyl acetate (10 mL). The ethyl acetate layer and the acetonitrile layer were combined, and washed with water:brine (10:1, 10 mL×2) to adjust the pH to 5. Subsequently, the combined layers were washed with brine, and dried over anhydrous magnesium sulfate, followed by filtration and distilling off of the solvents to obtain 710 mg of Compound 6 as a yellow oily substance with a yield of 67%.

Physicochemical Property of Compound 6

$^1$H-NMR (400 MHz, CDCl$_3$): δ 0.88 (t, J=6.8 Hz, 3H), 1.20-1.45 (m, 19H), 1.52-1.62 (m, 4H), 2.03 (dt, J=6.8, 6.4 Hz, 2H), 3.06 (d, J=6.4 Hz, 2H), 3.93 (s, 4H), 5.47-5.63 (m, 2H).

LCMS (ES+): Rt=5.95 min., m/z (rel int) 341 [M+1]

1-9 (Step 1-8)

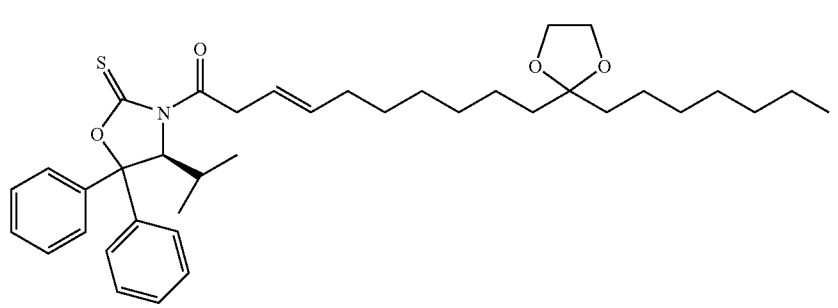

7

(S)-4-isopropyl-5,5-diphenyloxazolidine-2-thione (synthesized according to the process described in organic Letters (2002), 4(13), 2253-2256) (56 mg, 0.188 mmol) and Compound 6 (64 mg, 0.188 mmol) were dissolved in toluene (1.0 mL), and WSC—HCL (40 mg, 0.207 mmol), triethylamine $^1$H-NMR Chemical shift value δ (in deuterated chloroform): 0.88 (3H, t, J=7 Hz), 1.14-1.42 (28H, m), 1.55-1.64 (6H, m), 1.76-1.80 (4H, m), 1.96-2.01 (6H, m), 2.80-2.94 (4H, m), 3.92 (4H, s), 5.41-5.51 (1H, m), 5.57-5.66 (1H, m)
1-11 (Step 1-8)

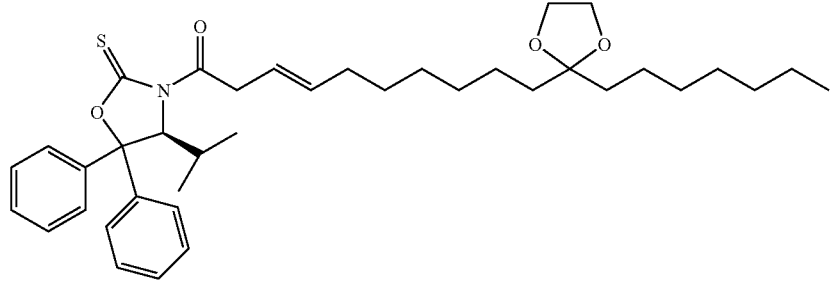

7

(29 µL, 0.207 mmol) and DMAP (2 mg, 0.207 mmol) were added under ice cooling, followed by stirring for 1 hour at the same temperature. Subsequently, a saturated aqueous ammonium chloride solution (10 mL) was added to stop the reaction. After ethyl acetate was added and the mixture was shaken vigorously, the organic layer was separated, the aqueous layer was extracted with ethyl acetate, the organic layers were combined, washed with saturated aqueous ammonium chloride solution, aqueous sodium bicarbonate solution and brine, followed by filtration and distilling off of the solvents to obtain 1.09 mg of a crude product as a colorless oily substance. Purification by column chromatography afforded Compound 7 as a colorless oily substance with a yield of 46%.

Physicochemical Property of Compound 7

$^1$H-NMR (400 MHz, CDCl$_3$): δ 0.79 (d, J=6.8 Hz, 3H), 0.83-0.89 (m, 6H), 1.20-1.38 (m, 18H), 1.54-1.63 (m, 4H), 1.91-2.07 (m, 3H), 3.81-4.08 (m, 6H), 3.92 (s, 4H), 5.40-5.62 (m, 3H), 7.14-7.51 (m, 10H).

LCMS (ES+): Rt=8.18 min., m/z (rel int) 620 [M+1] (80), 642 (100)

1-10 (Step 1-7)

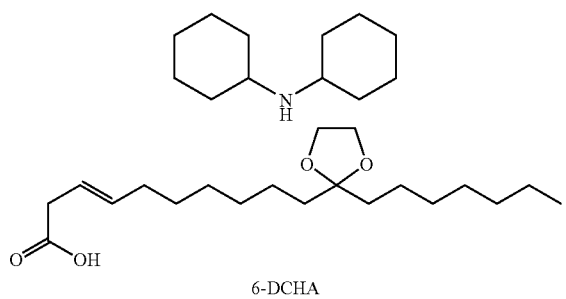

6-DCHA

To an acetonitrile (10 mL) solution of the crude product (1.0 g, 2.94 mmol) of Compound 6 obtained in the previously mentioned Example 1-8, dicyclohexylamine (DCHA) (533 mg, 2.94 mmol) and a seed crystal were added, followed by stirring at room temperature for 1 hour, and at 0° C. for 1 hour. The precipitated solid was filtered off to obtain Compound 6-DCHA (1.5 g) as a white solid. The crystallinity of Compound 6 was improved by forming a salt together with a base such as DCHA used in the present step, which enabled purification by means of recrystallization method.

To a mixture of Compound 6-DCHA (500 mg, 0.958 mmol) and hexane (10 mL), 0.5 N aqueous potassium hydrogen sulfate solution (10 mL) was added, to be separated. The organic layer was washed with water, concentrated under reduced pressure to obtain crudely-purified compound 6 (324 mg) as a yellow oil. To anhydrous dichloromethane solution (3 mL) of the crudely-purified compound 6 (324 mg), 4-dimethylaminopyridine (11.7 mg, 0.0958 mmol) and 4S-isopropyl-5,5-diphenyloxazolidine-2-thione (258 mg, 0.958 mmol) were added sequentially. The reaction solution was cooled to 0° C., and 1-(3-dimethylaminopropyl)-3-ethylcarbodiimide hydrochloride (230 mg, 1.20 mmol) was added and stirred at the same temperature for 6 hours. The mixture was diluted with dichloromethane, the organic layer was washed with water and brine, and then dried over anhydrous sodium sulfate. Concentration under reduced pressure afforded crudely-purified compound 7 (595 mg) as a yellow oil. The crudely-purified compound 7 was used as it is for the next reaction.

Example 2

Synthesis of Compound 5

2-1 (Step 2-1):

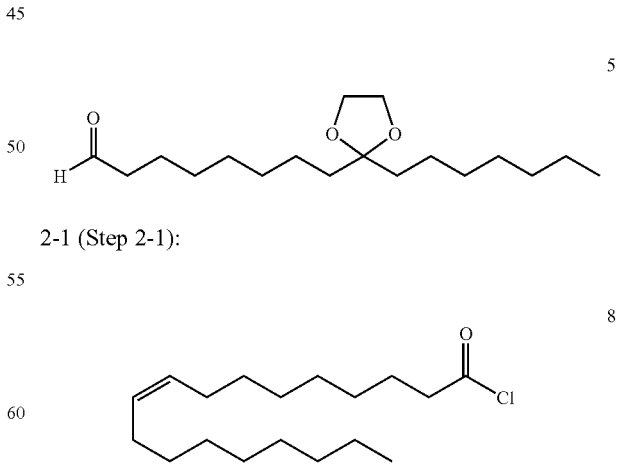

To an ice-cooled benzene solution (5 mL) of oleic acid (0.32 mL, 1.00 mmol), under a nitrogen atmosphere, oxalyl chloride (0.26 mL, 3.00 mmol) was added, followed by stirring for 4 hours while gradually raising to room temperature.

Subsequently, an excess of oxalyl chloride and benzene were distilled off with an evaporator to obtain Compound 8.

The whole amount of the present compound was used directly for the next reaction.

2-2 (Step 2-2):

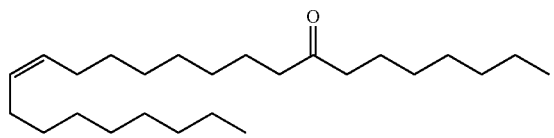

9

After the above compound 8 was dissolved in tetrahydrofuran (5 mL), tris(2,4-pentanedionato)iron(III) (35 mg, 0.1 mmol) was added, cooled with ice, and subsequently tetrahydrofuran solution (1.2 mL, 1.2 mmol) of n-heptylmagnesium bromide was added over 5 minutes. After stirring at the same temperature for 30 minutes, 1N hydrochloric acid was added to stop the reaction, followed by extraction with ethyl acetate. The organic layers were combined, washed with saturated aqueous sodium bicarbonate solution and brine, and dried over magnesium sulfate. After distilling off the solvents, the resulting residue was purified by column chromatography to obtain Compound 9 (300 mg, 0.823 mmol, 82% yield) as a colorless oily substance.

Physicochemical Property of Compound 9

$^1$H-NMR (400 MHz, CDCl$_3$): δ 0.88 (t, J=6.8 Hz, 6H), 1.20-1.40 (m, 28H), 1.50-1.62 (m, 4H), 1.93-2.09 (m, 4H), 2.38 (t, J=7.6 Hz, 4H), 5.29-5.42 (m, 2H).

MS (EI): m/z (rel int) 364 (50 [M+]), 265 (85), 209 (100), 127 (82), 57 (68)

2-3 (Step 2-3)

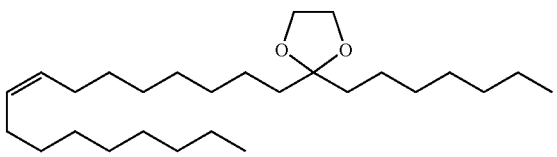

10

To a benzene solution (5 mL) of Compound 9 (290 mg, 0.795 mmol), ethylene glycol (0.089 mL, 1.58 mmol) and a catalytic amount of p-toluenesulfonic acid (5 mg) were added, which was heated to reflux for 6 hours while removing generated water by means of Dean-Stark trap. After cooling the reaction solution to room temperature, the reaction was stopped with saturated aqueous sodium bicarbonate solution, followed by extraction with ethyl acetate. The organic layers were combined, washed with saturated aqueous sodium bicarbonate solution and brine, and dried over magnesium sulfate. After distilling off the solvents, the resulting residue was purified by column chromatography to obtain Compound 10 (301 mg, 0.736 mmol, 93% yield) as a colorless oily substance.

Physicochemical Property of Compound 10

$^1$H-NMR (400 MHz, CDCl$_3$): δ 0.88 (t, J=6.8 Hz, 6H), 1.20-1.40 (m, 26H), 1.50-1.62 (m, 6H), 1.93-2.09 (m, 4H), 3.92 (s, 4H), 5.30-5.42 (m, 2H).

MS (EI): m/z (rel int) 408 (10 [M+]), 309 (100), 281 (35), 255 (38), 171 (100), 57 (25)

2-4 (Step 2-4)

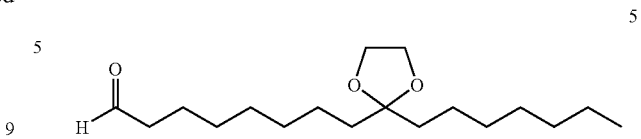

5

Under a nitrogen atmosphere, dichloromethane-methanol mixed solution (1:1, 10 mL) of Compound 10 (269 mg, 0.658 mmol) was cooled to −78° C., and ozone was passed through the solution for 10 minutes. In order to decompose an excess of ozone and the generated ozonide, an excess of triethylamine were added. The temperature of the reaction solution was returned to room temperature, and the solvents were distilled off. The resulted residue was purified by column chromatography to obtain Compound 5 as a colorless oily substance (48 mg, 0.159 mmol, 24% yield).

Example 3

Synthesis of Compound 15

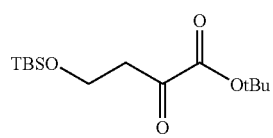

15

3-1 (Step 3-1):

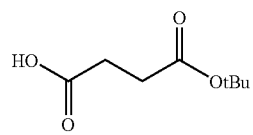

11

Compound 11 was synthesized according to the reference (J. Org. Chem. 68, 6679-6684 (2003)).

3-2 (Step 3-2):

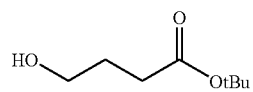

12

Compound 12 was synthesized according to the reference (J. Org. Chem. 68, 6679-6684 (2003)).

3-3 (Step 3-3):

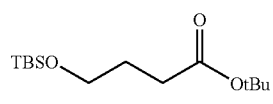

13

4-Hydroxy-butyric acid t-butyl ester (12.996 g) synthesized according to the reference (J. Org. Chem. 68, 6679-6684 (2003)) and imidazole (5.522 g) were dissolved in dry DMF (60 mL). After the solution was cooled with an ice bath, t-butyldimethylsilyl chloride (12.227 g) was added, and the temperature of the mixture was raised gradually to room temperature (25 to 28° C.). After stirring for 10 hours, hexane (150 mL) was added. The organic layer was washed three times with water (100 mL). The organic layer was washed with a half-saturated aqueous ammonium chloride solution (about 10%) (100 mL), dried over anhydrous sodium sulfate, filtered off, and the filtrate was concentrated to obtain a crude product of Compound 13 as a yellow oil (20.383 g). Out of this amount, 18.232 g was distilled under reduced pressure (bp 93° C./1.0 mmHg) to obtain a colorless oil 13 (15.3 g).
Physicochemical Property of Compound 13
ESI (LC/MS positive mode) (M+H$^+$) 275
$^1$H-NMR Chemical shift value δ (in deuterated chloroform): 0.05 (6H, s), 0.89 (9H, s), 1.45 (9H, s), 1.74-1.84 (2H, m), 2.29 (2H, t, J=7 Hz), 3.63 (2H, t, J=7 Hz)
3-4 (Step 3-4)

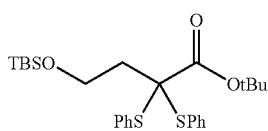

14

Dry tetrahydrofuran (50 mL) was added to Compound 13 (15.3 g), and cooled to −78° C. (outside temperature) with dry ice-methanol bath. To the present solution, lithium diisopropylamide (1.8N solution in a mixed solvent of heptane and tetrahydrofuran, 21.25 mL) was added dropwise over 5 minutes, followed by stirring at the same temperature for 1 hour. To the present solution, diphenyl disulfide (8.351 g) was added. After 5 minutes, the cooling bath was removed to raise the temperature to room temperature. After stirring at room temperature for 1 hour, the reaction solution was cooled to −30° C., and sodium hexamethyldisilazide (1N tetrahydrofuran solution, 38.25 mL) was added dropwise over 10 minutes. After 10 minutes, diphenyl disulfide (8.351 g) was added, followed by stirring at the same temperature for 5 minutes. The cooling bath was removed, followed by stirring at room temperature for 1.5 hours. Hexane (100 mL) was added to the reaction solution, and the organic layer was washed with 100 mL of water.

The organic layer was washed twice with an aqueous sodium carbonate solution (100 mL). The organic layer was washed with a saturated aqueous ammonium chloride solution. The organic layer was dried over anhydrous sodium sulfate, filtered off, and concentrated.

The resulting oil was crudely purified by silica gel column chromatography. A fraction containing a desired substance was concentrated to obtain Compound 14 (15.473 g).
Physicochemical Property of Compound 14
ESI (LC/MS positive mode) (M+H$^+$) 491
$^1$H-NMRb Chemical shift value δ (in deuterated chloroform): −0.03 (6H, s), 0.83 (9H, s), 1.35 (9H, s), 2.02-2.08 (2H, m), 3.80-3.85 (2H, m), 7.30-7.42 (6H, m), 7.63-7.73 (4H, m)
3-5 (Step 3-5)

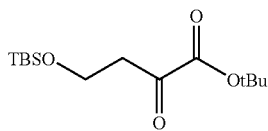

15

To Compound 14 (14.088 g) and sodium hydrogencarbonate (28.93 g), acetone (85 mL) and water (15 mL) were added. After cooling the present solution with a cooling bath at 0° C., iodine (36.42 g) was added. After stirring at the same temperature for 1 hour, the reaction mixture was added to an aqueous solution (150 mL) of sodium thiosulfate dihydrate (78.35 g). After extraction with t-butyl methyl ether (150 mL), the separated aqueous layer was extracted with t-butyl methyl ether (50 mL). The combined organic layers were washed with water (100 mL) and brine (50 mL). After drying over anhydrous sodium sulfate, a crude product 15 was obtained through filtering off and concentration. Purification by silica gel column chromatography afforded Compound 15 (8.4 g).
Physicochemical Property of Compound 15
EI (M$^+$) 288
$^1$H-NMR Chemical shift value δ (in deuterated chloroform): 0.05 (6H, s), 0.87 (9H, s), 1.55 (9H, s), 2.98 (2H, t, J=6 Hz), 3.95 (2H, t, J=6 Hz)

As alternative methods to the above Example 3-4 (Step 3-4) and Example 3-5 (Step 3-5), the following Example 3-6 (Step 3-4) and Example 3-7 (Step 3-5) were carried out.
3-6 (Step 3-4)

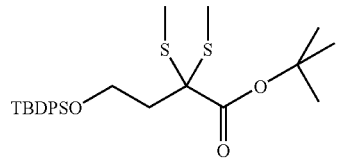

23

Under a nitrogen atmosphere, Compound 22 (35.1 g, 88.1 mmol, synthesized in Step 6-3 of Example 6 described later) was dissolved in tetrahydrofuran (270 mL), and cooled to −78° C. Lithium diisopropylamide (1.5 M cyclohexane solution, 64.6 mL, 96.9 mmol) was gradually added over 15 minutes, followed by stirring at −78° C. for 1.5 hours. Subsequently, dimethyl disulfide (9.1 mL, 88.4 mmol) was added gradually over 5 minutes, and then stirred at room temperature for 1 hour. After the mixture was cooled to −78° C. again, lithium diisopropylamide (1.5 M, 70.1 mL, 105 mmol) was gradually added over 15 minutes, followed by stirring at −78° C. for 0.5 hours. Subsequently, dimethyl disulfide (9.9 mL, 96.4 mmol) was added gradually at −78° C. over 5 minutes, and then stirred at room temperature for 1 hour. Thereafter, a saturated aqueous ammonium chloride solution was added, and extraction was carried out with ethyl acetate. After drying over sodium sulfate and filtration, concentration was carried out under reduced pressure. Isolation and purification by silica gel column chromatography (hexane:ethyl acetate=50: 1) afforded Compound 23 (38.95 g, 90.07%).
Physicochemical Property of Compound 23
FAB-MS (positive mode, matrix m-NBA) 491 (M+H$^+$)
$^1$H-NMR Chemical shift value δ (in deuterated chloroform): 1.04 (9H, s), 1.38 (9H, s), 1.95 (6H, s), 2.21-2.26 (2H, m), 3.78-3.84 (2H, m), 7.34-7.45 (6H, m), 7.64-7.70 (4H, m)
3-7 (Step 3-5)

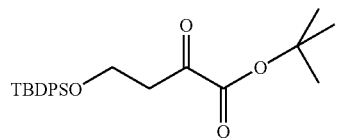

19

Compound 23 (39.0 g, 79.5 mmol) was dissolved in 95% aqueous acetone (1.1 L), and cooled to −30° C. N-bromosuccinimide (141.43 g) was gradually added thereto over 1 hour. Then, stirring was carried out at −30° C. for 10 minutes. A saturated aqueous sodium hydrogencarbonate solution was added slowly at −30° C. until it became pH=6 to 7, whereupon a white precipitate was formed. The precipitate was filtered off using a Kiriyama funnel, and the precipitate was washed with hexane. Extraction was carried out with hexane, and the organic layer was washed with brine and water. After drying over sodium sulfate and filtration, concentration was carried out under reduced pressure. Isolation and purification by silica gel column chromatography (neutral silica, hexane: ethyl acetate=10:1) afforded Compound 19 (26.72 g, 81.52%).

Example 4

Synthesis of Compound 15

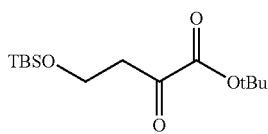

4-1 (Step 4-1):

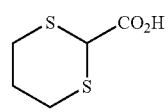

Compound 16 was synthesized according to the reference (Can. J. Chem. 58, 716 (1980)).

4-2 (Step 4-2):

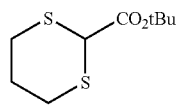

To Compound 16 (8.026 g), anhydrous tetrahydrofuran (15 mL) and t-butanol (15 mL) were added, and the flask was immersed in a water bath (25° C.), and subsequently di-t-butyl-dicarbonate (11.786 mL) was added. To the present solution, dimethylaminopyridine (1.79 g) was added, followed by stirring at room temperature. After stirring at the same temperature over night, the reaction solution was diluted with ethyl acetate (50 mL). The organic layer was washed three times with a saturated aqueous ammonium chloride solution (50 mL), water (25 mL) and brine, and dried over anhydrous sodium sulfate, followed by filtration and concentration. The resulting yellow oil was dried with a vacuum pump to obtain a crude product of Compound 17 (11.111 g). The present compound was used directly for the next reaction without purification.

Physicochemical Property of Compound 17

ESI (LC/MS positive mode) (M+H$^+$) 221

$^1$H-NMR Chemical shift value δ (in deuterated chloroform): 1.51 (9H, s), 1.99-2.14 (2H, m), 2.56-2.64 (2H, m), 3.35-3.45 (2H, m), 4.09 (1H, s)

4-3 (Step 4-3)

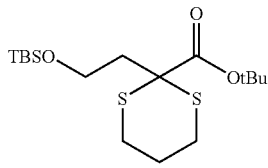

Sodium hydride (1.454 g) was put on a flask, and anhydrous toluene (30 mL) was added to cool to 0° C. (outside temperature).

The above compound 17 (8.011 g) and t-butyldimethylsilyloxyethyl bromide (7.8 mL) were dissolved in anhydrous DMF (10 mL), and added dropwise over 15 minutes. After stirring at the same temperature for 30 minutes, the flask was moved to a water bath at 25 to 27° C., and stirring was continued further for 1 hour and 40 minutes. The reaction solution was cooled to 0° C., and a saturated aqueous ammonium chloride solution (50 mL) was added slowly. Extraction was carried out with hexane (100 mL), and separated organic layer was washed three times with water (50 mL) and with brine, followed by drying over anhydrous sodium sulfate, and filtration. Concentration of the filtrate afforded Compound 18 (12.653 g).

Physicochemical Property of Compound 18

ESI (LC/MS positive mode) (M+H$^+$) 379

$^1$H-NMR Chemical shift value δ (in deuterated chloroform): 0.06 (6H, s), 0.89 (9H, s), 1.51 (9H, s), 1.80-1.92 (1H, m), 2.08-2.15 (1H, m), 2.22-2.26 (2H, m), 2.61-2.67 (2H, m), 3.26-3.33 (2H, m), 3.79-3.83 (2H, m)

4-4 (Step 3-5)

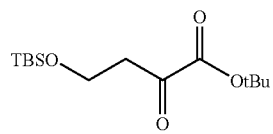

To N-bromosuccinimide (2.877 g) and silver nitrate (2.764 g), acetonitrile-water (35 mL, 9:1 v/v) was added, to cool the mixture to 0° C., and 2,6-lutidine (3.766 mL) was added. The above compound 18 (1000 mg) was dissolved in a mixed solvent of acetonitrile (5 mL)-acetone (2 mL), and was added dropwise over about 20 minutes. Stirring was carried out at the same temperature for 30 minutes. To the reaction solution, t-butyl methyl ether (50 mL) was added, and subsequently 50 mL of 20% aqueous ammonium chloride solution was added slowly over about 5 minutes. The mixture was moved to a separating funnel to remove the aqueous layer, and subsequently the organic layer was washed with 5% aqueous sodium sulfite solution (50 mL). Finally, the mixture was washed with brine (50 mL), followed by drying over anhydrous sodium sulfate.

Filtration, followed by concentration afforded 965 mg of a crude product. The crude product was purified by distillation under reduced pressure to obtain Compound 15 (451 mg, 58%).

Example 5

Synthesis of Compound 19

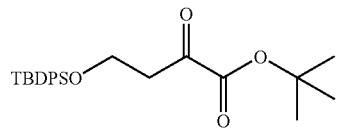

5-1 (Step 5-1):

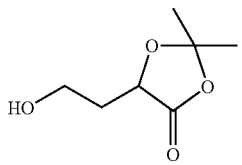
16

To 22 mL of tetrahydrofuran, at 0° C., borane dimethylsulfide complex (M.W.:75.97, 5.31 mL, 56.0 mmol) and trimethoxy borane acid (M.W.:103.9, 6.3 mL, 56.0 mmol) were added, and 53 mL of tetrahydrofuran containing (2,2-dimethyl-4-oxo-1,3-dioxolan-5-yl)acetic acid (synthesized according to the reference ACC. Chem. Res., 2002, 35, 774, 6.5 g, 37.3 mmol) was added dropwise over 20 minutes while the temperature remained 0° C. After stirring at 0° C. for 1 hour, stirring was carried out at room temperature for 14 hours. After the reaction solution was cooled to 0° C., 25 mL of methanol was added to stop the reaction, and the solvents were distilled off with a water bath at 26° C. Again, 50 mL of methanol was added, and the solvent was distilled off with a water bath at the same temperature, and then 50 mL of ethyl acetate was added to repeat the same operation. Compound 16 (5.8 g) obtained through the present synthesis was used directly for the next reaction.

5-2 (Step 5-2)

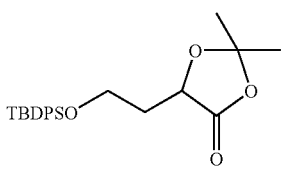
17

Compound 16 (5.8 g) was dissolved in 20 mL of DMF, and 15 mL of DMF solution of imidazole (M.W.:68.08, 5.08 g, 74.6 mmol) and t-butyldiphenylchlorosilane (M.W.:274.86, 10.25, 37.3 mmol) were added sequentially. After stirring at room temperature for 19 hours, 50 mL of water was added to stop the reaction, and 150 mL of hexane was added for extraction. The aqueous phase was washed with 100 mL of hexane, and the combined organic phases were washed with 100 mL of water, followed by drying over magnesium sulfate.

After filtration of the mixed solution, the solvent was distilled off, and dried with a vacuum pump to obtain Compound 17 (94%, 13.95 g).

Physicochemical Property of Compound 17

$^1$H-NMR (400 MHz, CDCl$_3$): δ 1.05 (s, 9H), 1.54 (s, 3H), 1.57 (s, 3H), 1.88-1.94 (m, 1H), 2.13-2.19 (m, 1H), 3.77-3.81 (m, 1H), 3.85-3.89 (m, 1H), 4.62 (dd, J=3.9, 8.0 Hz, 1H), 7.35-7.44 (m, 6H), 7.65-7.68 (m, 4H).

MS (EI): m/z (rel int)399 (50 [M+1]), 321 (100), 235 (10).

5-3 (Steps 5-3 and 5-4)

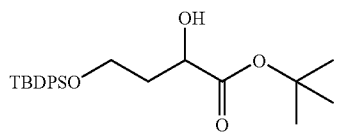
18

After 12 mL of a mixed solution of Compound 17 (4.55 g, 11.42 mmol) in toluene-t-butanol (2:1) was cooled to 0° C., 1.09 g of sodium t-butyrate (11.42 mmol) was added. After stirring at 0° C. for 15 minutes, t-butyl bromide (26.3 mL, 251.2 mmol), 2.60 g of benzyltriethylammonium chloride (11.42 mmol) and 15.8 g of potassium carbonate (114.2 mmol) were added sequentially, and allowed to reach to room temperature, followed by stirring at 55° C. for 20 hours. After completion of the reaction, the reaction solution was cooled to room temperature, and the solid was removed by filtration (200 mL of hexane for washing). 70 mL of water was added to the filtrate followed by extraction, and the organic phase was washed with 100 mL of water, followed by drying over sodium sulfate. After the mixed solution was filtered, the solvents were distilled off and dried with a vacuum pump to obtain Compound 18 (95%, 4.51 g).

Physicochemical Property of Compound 18

$^1$H-NMR (400 MHz, CDCl$_3$): δ 1.03 (s, 9H), 1.86-2.03 (m, 1H), 2.07-2.27 (m, 1H), 3.87-3.94 (m, 2H), 4.47 (dd, J=4.2, 7.3 Hz, 1H), 7.37-7.44 (m, 6H), 7.63-7.71 (m, 4H).

MS (EI): m/z (rel int) 359 (100 [M+1]), 281 (55), 235 (10), 175 (20).

5-4 (Step 5-5)

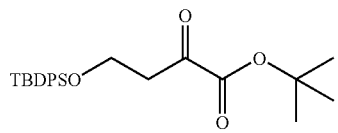
19

A 100 mL acetone solution of Compound 18 (4.51 g, 10.88 mmol) was cooled to 0° C., and 30 mL of 15% aqueous sodium hydrogencarbonate solution, sodium bromide (223.8 mg, 2.18 mmol), TEMPO (170 mg, 1.09 mmol) and trichloroisocyanuric acid (5.06 g, 21.8 mmol) were added sequentially, followed by stirring at room temperature for 27 hours. After the completion of the reaction, 3 mL of 2-propanol was added, and filtration was carried out. The filtrate was extracted with 200 mL of ethyl acetate and 50 mL of water, and the aqueous phase was washed with 150 mL of ethyl acetate. Subsequently, the combined organic phases were washed with 10 mL of 1.0N aqueous hydrochloric acid solution and 100 mL of water, and dried over sodium sulfate. After filtration of the mixed solution, the solvent was distilled off and purified by silica gel column chromatography to obtain 2.11 g of Compound 19 (yield 42%: 5 Step yield).

Physicochemical Property of Compound 19

$^1$H-NMR (400 MHz, CDCl$_3$): δ 1.02 (s, 9H), 1.54 (s, 9H), 3.01 (t, J=6.4 Hz, 2H), 3.99 (t, J=6.4 Hz, 2H), 7.36-7.45 (m, 6H), 7.62-7.67 (m, 4H).

MS (EI): m/z (rel int)435 (15 [M+Na]), 280 (100), 220 (10).

Example 6

Synthesis of Compound 22

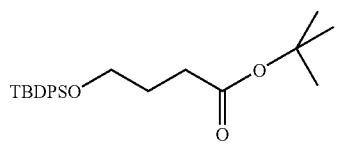
22

6-1 (Step 6-1):

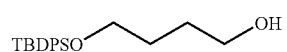
20

Under a nitrogen atmosphere, 1,4-butanediol (100 g, 1.1 mmol) and diisopropylethylamine (200 mL, 1.14 mmol) were dissolved in dichloromethane (200 mL), and at room temperature t-butyldiphenylsilyl chloride (100 mL, 0.38 mmol) was added gradually over 15 minutes. At room temperature, stirring was carried out for 2.5 hours, followed by concentration under reduced pressure, dissolution in ethyl ether, and washing with water. After drying using sodium sulfate and filtration, concentration was carried out under reduced pressure to obtain 127.16 g of Compound 20.

Physicochemical Property of Compound 20

¹H NMR (300 MHz, CDCl₃) δ: 7.68 (4H, m), 7.25-7.46 (6H, m), 3.68 (4H, m), 1.66 (4H, m), 1.06 (9H, s)

6-2 (Step 6-2)

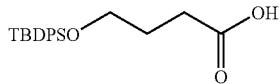

21

Compound 20 (63.6 g, 0.19 mmol) was dissolved in 1.8 liter of acetone, and at 0° C. 540 mL of 15% aqueous sodium hydrogen carbonate solution, sodium bromide (3.7 g) and TEMPO (563 mg) were added in this order, followed by gradual addition of trichloroisocyanuric acid (83.6 g) over 30 minutes. Subsequently, stirring was carried out at room temperature for 1.5 hours, and 2-propanol (108 mL) was added. Concentration under reduced pressure allows acetone to be removed. Ethyl acetate was added, followed by washing with water. After drying over sodium sulfate and filtration, concentration was carried out under reduced pressure. Purification by silica gel column chromatography (silica 60, hexane:ethyl acetate=9:1) afforded Compound 21 (58.78 g, 95.5%).

Physicochemical Property of Compound 21

ESI (LC/MS positive mode) (M+H⁺) 343

¹H-NMR Chemical shift value δ (in deuterated chloroform): 1.05 (9H, s), 1.84-1.94 (2H, m), 2.51 (2H, t, J=6 Hz), 3.70 (2H, t, J=6 Hz), 7.35-7.45 (6H, m), 7.66 (4H, d, J=6 Hz)

6-3 (Step 6-3)

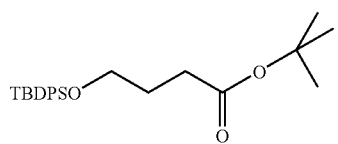

22

Under a nitrogen atmosphere, Compound 21 (75.49 g, 0.22 mmol) was dissolved in dry benzene (221 mL), and was refluxed. Subsequently, dimethylformamide-di-t-butylacetal (211 mL, 0.836 mmol) was added gradually over 40 minutes, and refluxed for 17 hours, which was then cooled to room temperature followed by the addition of ethyl acetate, and the organic layer was washed with water, a saturated aqueous sodium hydrogen carbonate solution and brine. After drying over sodium sulfate and filtration, concentration was carried out under reduced pressure. Purification by silica gel column chromatography (silica 60, hexane:ethyl acetate=50:1) afforded Compound 22 (70.12 g, 79.8%).

Physicochemical Property of Compound 22

FAB-MS (positive mode, matrix m-NBA) 399 (M+H⁺)

¹H-NMR Chemical shift value δ (in deuterated chloroform): 1.05 (9H, s), 1.43 (9H, s), 1.84-1.89 (2H, m), 2.36 (2H, t, J=6 Hz), 3.67 (2H, t, J=6 Hz), 7.34-7.70 (10H, m)

Example 7

Synthesis of the Following Compound

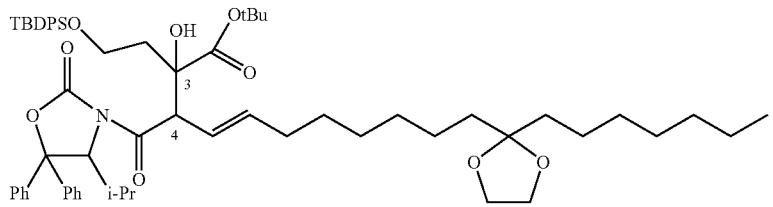

Step 7-1

200 mg of the following compound synthesized according to General Step-1 was treated, in a solvent shown in the following table, and in the presence of an additive shown below, with 1.05 to 1.1 equivalents of lithium diisopropylamide or n-butyllithium at −78° C. for 1 hour, and then reacted with 1.1 equivalents of Compound 19 synthesized in Example 3-7 or 5 at −78° C. for 1 hour, whereupon the title compound was obtained with a high yield. Considering the configuration of the obtained compound, a high stereoselectivity was confirmed as shown in the following table.

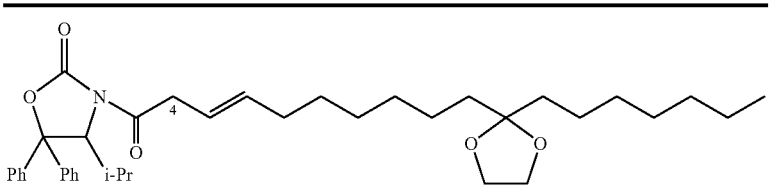

| Solvent | Additive | Base | Product | anti:syn | Yield (%) |
|---|---|---|---|---|---|
| Tetrahydrofuran | None | n-BuLi | Anti 1 | 7:1 | 90 |
| Tetrahydrofuran | HMPA | n-BuLi | Anti 1 | 7:1 | 86 |
| Toluene | None | LDA | Anti 2 | 7:1 | 70 |

Here, Anti 1 product represents (3S,4S) form; Anti 2 product represents (3R,4R) form; Syn 1 product represents (3R,4S) form; and Syn 2 product represents (3S,4R) form. In addition, Syn in the table indicates a total of Syn 1 product and Syn 2 product. Further, in the case where a solvent is tetrahydrofuran, n-butyllithium was used as a base; and in the case where a solvent is toluene, lithium diisopropylamide was used as a base.

Example 8
Synthesis of the Following Compound

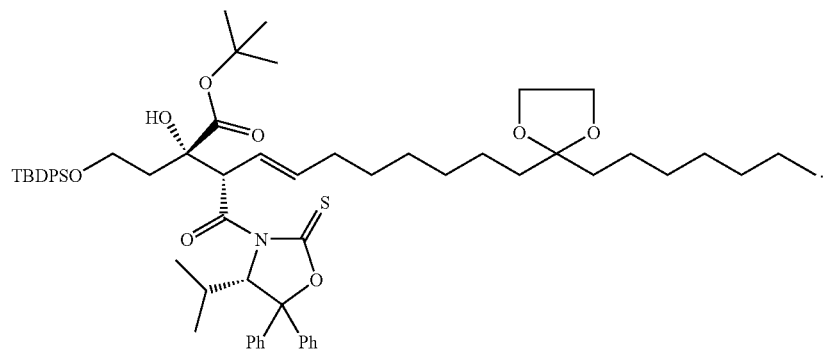

24

Step 7-1

The following Compound 7 synthesized in Example 1 in 0.16 M tetrahydrofuran solution was reacted at −78° C., in the presence of 1.05 equivalents of lithium hexamethyldisilazide and lithium chloride in an amount shown in the following table, and then reacted at −78° C. with 1.1 equivalents of Compound 19 synthesized in Example 6, whereupon the title compound was obtained with a high yield. The configuration of the obtained compound was studied. As a result, as shown in the following table, Anti 1 product was obtained selectively, with a high stereoselectivity being confirmed, and in the presence of lithium chloride it was confirmed that a higher stereoselectivity can be obtained.

7

| Amount of Compound 7 (mg) | Amount of LiCi (equivalent(s)) | Enolate formation time (hour) | Time of addition of Compound 19 (min.) Aldol reaction time (min.) | Anti:Syn | Conversion rate (%) | Yield (%) |
|---|---|---|---|---|---|---|
| 92.8 | None | 1 | 4 / 33 | 10:1.13 | 54 | 45.6 |
| 214.5 | 1 | 2 | 8 / 32 | Only Anti product | 80 | 73 |
| 174.2 | 4 | 3 | 8 / 37 | Only Anti product | 85 | 79 |

In the Table, Anti indicates Anti 1 product, and Syn indicates a total of Syn 1 product and Syn 2 product.

Example 9

Synthesis of Compound 30

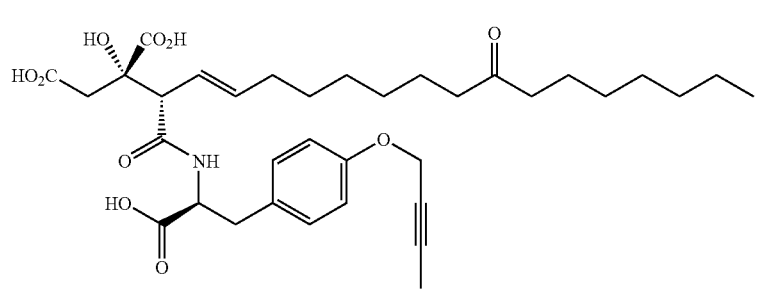

Step 9-1 (Step 7-1)

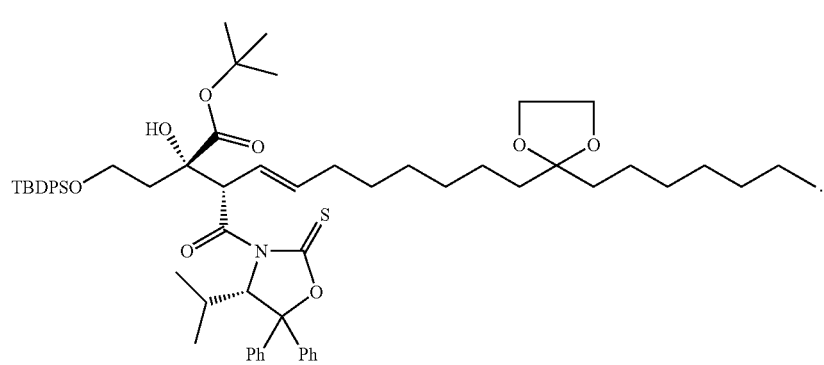

An anhydrous tetrahydrofuran solution (6.4 mL) of Compound 7 (500 mg, 0.807 mmol) synthesized in Example 1 was cooled to −78° C., and lithium hexamethyldisilazide (0.799 mL, 0.847 mmol, 1.06 M hexane solution) was added, followed by stirring for 2 hours and 20 minutes. An anhydrous tetrahydrofuran solution (8.6 mL) of Compound 19 (366 mg, 0.887 mmol) synthesized in Example 5 was added dropwise slowly over 20 minutes, and further stirred at the same temperature for 2 hours, followed by the addition of acetic acid (0.127 mL). An aqueous ammonium chloride solution was added followed by extraction with ethyl acetate, and the organic layer was dried over anhydrous sodium sulfate. A crude product obtained through concentration under reduced pressure was purified by column chromatography to obtain Compound 24 (364 mg) as a colorless oily substance.

Physicochemical Property of Compound 24

ESI (LC/MS positive mode) 1049 (M+NH$_4^+$)

$^1$H-NMR Chemical shift value δ (in deuterated chloroform): 0.73 (3H, d, J=7 Hz), 0.79 (3H, d, J=7 Hz), 0.83-1.79 (27H, m), 1.01 (9H, s), 1.34 (9H, s), 1.90-2.07 (3H, m), 3.31-3.41 (1H, m), 3.52 (1H, s), 3.59-3.69 (1H, m), 3.90 (4H, s), 5.50-5.62 (1H, m), 5.70 (1H, d, J=4 Hz), 5.85-5.98 (1H, m), 6.14 (1H, d, J=9 Hz), 7.02-7.68 (20H, m).

9-2 (Step 7-2)

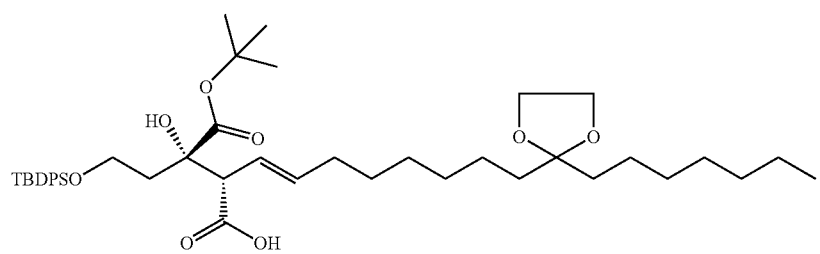

A tetrahydrofuran solution (62 mL) of Compound 24 (850 mg, 0.823 mmol) was cooled to −10° C., and a mixture of lithium hydroxide monohydrate (62 mg, 1.48 mmol), water (7.4 mmol) and 34.5% hydrogen peroxide solution (0.487 mL) was added slowly, followed by stirring at the same temperature for 30 minutes and 0° C. for 1.5 hours. To the reaction solution, a 5% aqueous sodium thiosulfate solution, and a 0.05 M aqueous citric acid solution were added sequentially, followed by extraction with ethyl acetate. The organic layer was washed with water and brine, and dried over anhydrous sodium sulfate. A crude product obtained through concentration under reduced pressure was purified by column chromatography (silica gel, hexane-acetone-methylene chloride 15:1:1) to obtain Compound 25 (673 mg) as a colorless oily substance.

Physicochemical Property of Compound 25

ESI (LC/MS positive mode) 775 (M+Na$^+$)

$^1$H-NMR Chemical shift value δ (in deuterated chloroform): 0.82-0.92 (3H, m), 1.05 (9H, s), 1.37 (9H, s), 1.18-1.42 (18H, m), 1.50-1.63 (4H, m), 1.82-2.20 (4H, m), 3.40 (1H, d, J=9 Hz), 3.64-3.85 (2H, m), 3.92 (4H, s), 5.21 (1H, brs), 5.52 (1H, dd, J=9, 15 Hz), 5.74 (1H, dt, J=7, 15 Hz), 7.24-7.65 (10H, m).

9-3 (Step 7-2)

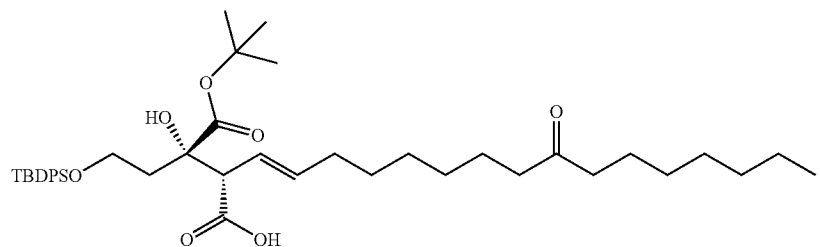

26

To a tetrahydrofuran solution (0.5 mL) of Compound 25 (1.55 g, 2.06 mmol), a 80% aqueous acetic acid solution (50 mL) was added, followed by stirring at room temperature for 5 hours. The reaction solution was concentrated under reduced pressure, and the resulting crude product was purified by column chromatography to obtain Compound 26 (1.38 g) as a colorless oily substance.

Physicochemical Property of Compound 26

ESI (LC/MS positive mode) 731 (M+Na$^+$)

$^1$H-NMR Chemical shift value δ (in deuterated chloroform): 0.88 (3H, t, J=7 Hz), 1.05 (9H, s), 1.27-1.37 (23H, m), 1.51-1.60 (4H, m), 1.97-2.19 (4H, m), 2.35-2.40 (4H, m), 3.40 (1H, d, J=9 Hz), 3.66-3.84 (2H, m), 5.28 (1H, brs), 5.52 (1H, dd, J=9, 15 Hz), 5.74 (1H, dt, J=7, 15 Hz), 7.36-7.47 (6H, m), 7.62-7.68 (4H, m)

9-4 (Step 7-4)

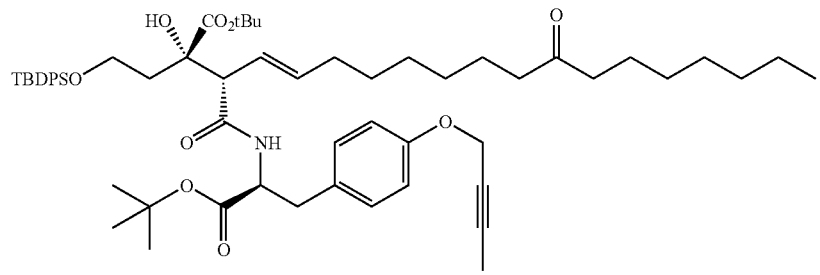

27

To an anhydrous N,N-dimethylformamide solution (34 mL) of Compound 26 (1.216 g, 1.715 mmol) and (S)-4-(2-butynyloxy)phenylalanine t-butyl ester hydrochloride (671 mg, 2.058 mmol), N,N-diisopropylethylamine (1.34 mL, 7.72 mmol) was added. The reaction solution was cooled to 0° C., and O-(7-azabenzotriazol-1-yl)-N,N,N',N'-tetramethyluronium hexafluorophosphate (717 mg, 1.886 mmol) was added, followed by stirring at the same temperature for 2 hours. An aqueous ammonium chloride solution was added to stop the reaction, followed by extraction with 20% ethyl acetate-hexane. The organic layer was washed with water and brine, and subsequently dried over anhydrous sodium sulfate. A crude product obtained through concentration under reduced pressure was purified by column chromatography (silica gel, hexane-ethyl acetate 4:1) to obtain Compound 27 (1.58 g) as a colorless oily substance.

Physicochemical Property of Compound 27
ESI (LC/MS positive mode) 980 (M+H⁺)
$^1$H-NMR Chemical shift value δ (in deuterated chloroform): 0.87 (3H, t, J=7 Hz), 1.04 (9H, s), 1.17-2.24 (22H, m), 1.30 (9H, s), 1.37 (9H, s), 1.84 (3H, t, J=2 Hz), 2.32-2.40 (4H, m), 2.97 (1H, dd, J=6, 14 Hz), 3.08 (1H, dd, J=6, 14 Hz), 3.16 (1H, d, J=10 Hz), 3.54-3.64 (1H, m), 3.74-3.84 (1H, m), 4.32 (1H, s), 4.54 (2H, q, J=2 Hz), 4.66-4.74 (1H, m), 5.50 (1H, dd, J=9, 15 Hz), 5.63 (1H, dt, J=6, 15 Hz), 6.78-6.84 (2H, m), 7.03 (1H, d, J=8 Hz), 7.08-7.14 (2H, m), 7.30-7.68 (10H, m).

9-5 (Step 7-5)

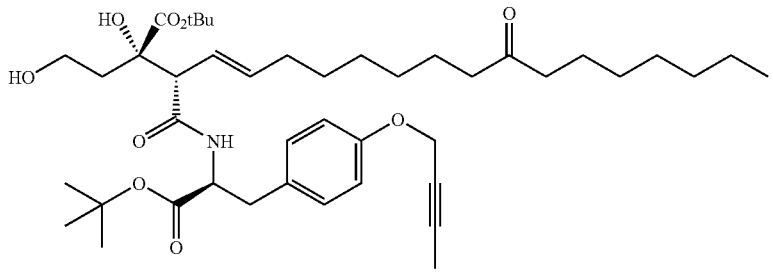

28

A tetrahydrofuran solution (15.7 mL) of Compound 27 (1.54 g, 1.57 mmol) was cooled to 0° C., and acetic acid (0.225 mL, 4.71 mmol) and tetrabutylammonium fluoride (4.71 mL, 4.71 mmol, a 1.0 M tetrahydrofuran solution) were added sequentially, followed by stirring at room temperature for 1 hour. Water was added to the reaction solution, followed by extraction with ethyl acetate. The organic layer was washed with a saturated aqueous sodium hydrogencarbonate solution and brine, and subsequently dried over anhydrous sodium sulfate. A crude product obtained through concentration under reduced pressure was purified by column chromatography to obtain Compound 28 (1.63 g) as a colorless oily substance.

Physicochemical Property of Compound 28
ESI (LC/MS positive mode) 742 (M+H⁺)
$^1$H-NMR Chemical shift value δ (in deuterated chloroform): 0.88 (3H, t, J=7 Hz), 1.41 (9H, s), 1.44 (9H, s), 1.17-2.20 (23H, m), 1.86 (3H, t, J=3 Hz), 2.32-2.41 (4H, m), 2.94-3.11 (2H, m), 3.14 (1H, d, J=9 Hz), 3.56-3.72 (2H, m), 4.46 (1H, brs), 4.59-4.64 (2H, m), 4.70 (1H, q, J=6 Hz), 5.50 (1H, dd, J=9, 15 Hz), 5.66 (1H, dt, J=6, 15 Hz), 6.78-6.90 (3H, m), 7.07-7.14 (2H, m).

9-6 (Step 7-6)

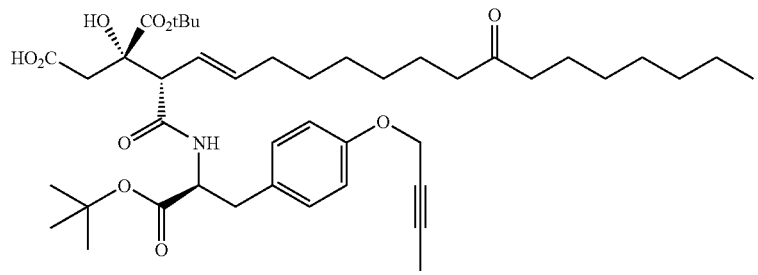

29

A mixed solution of Compound 28 (180 mg, 0.243 mmol) in acetonitrile (2.4 mL) and water (0.48 mL) was cooled to 0° C., and 2,2,6,6-tetramethyl-1-piperidinyloxy free radical (7.6 mg, 0.0485 mmol) and iodobenzene diacetate (211 mg, 0.655 mmol) were added sequentially, followed by stirring at room temperature for 2 hours. Subsequently, water (0.48 mL) was added, followed by stirring further at room temperature for 30 minutes. To the reaction solution, 0.5 M aqueous citric acid solution was added, followed by extraction with ethyl acetate. The organic layer was washed sequentially with water, 10% aqueous sodium thiosulfate solution and brine, and dried over anhydrous sodium sulfate. A crude product obtained through concentration under reduced pressure was purified by column chromatography to obtain Compound 29 (142 mg) as a colorless oily substance.

Physicochemical Property of Compound 29

ESI (LC/MS positive mode) 756 (M+H$^+$)

$^1$H-NMR Chemical shift value δ (in deuterated chloroform): 0.88 (3H, t, J=8 Hz), 1.41 (9H, s), 1.44 (9H, s), 1.16-1.82 (20H, m), 1.86 (3H, t, J=2 Hz), 1.94-2.06 (2H, m), 2.37 (4H, t, J=8 Hz), 2.56 (1H, d, J=16 Hz), 2.82 (1H, d, J=16 Hz), 2.94-3.12 (2H, m), 3.21 (1H, d, J=10 Hz), 4.58-4.74 (3H, m), 5.48 (1H, dd, J=9, 15 Hz), 5.66 (1H, dt, J=6, 15 Hz), 6.78 (1H, d, J=8 Hz), 6.82-6.90 (2H, m), 7.09-7.15 (2H, m).

9-7 (Step 7-7)

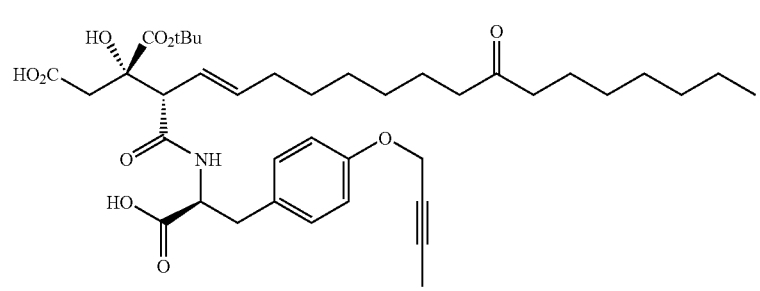

30

To a dichloromethane solution (0.55 mL) of Compound 29 (110 mg, 0.146 mmol), a mixed solution of trifluoroacetic acid (0.88 mL) and water (0.22 mL) was added. After stirring at room temperature for 4 hours, concentration was carried out under reduced pressure. A solution of ethyl acetate (0.5 mL) of a crude product obtained through concentration under reduced pressure, heptane (1 mL) and a seed crystal (Compound 30) were added, followed by stirring at room temperature for 2 hours. The precipitated solid was filtered off to obtain Compound 30 (81.4 mg).

Physicochemical Property of Compound 30

ESI (LC/MS positive mode) 644 (M+H$^+$)

$^1$H-NMR Chemical shift value δ (in deuterated chloroform): 0.87 (3H, t, J=7 Hz), 1.14-1.64 (16H, m), 1.84 (3H, t, J=2 Hz), 1.88-2.04 (2H, m), 2.40 (4H, t, J=7 Hz), 2.71 (1H, d, J=16 Hz), 2.88-3.24 (3H, m), 3.30 (1H, d, J=9 Hz), 4.54-4.72 (3H, m), 5.38-5.66 (2H, m), 5.45 (3H, brs), 6.84 (2H, d, J=9 Hz), 7.09 (2H, d, J=9 Hz), 7.35-7.50 (1H, m).

9-8 (Step 7-1)

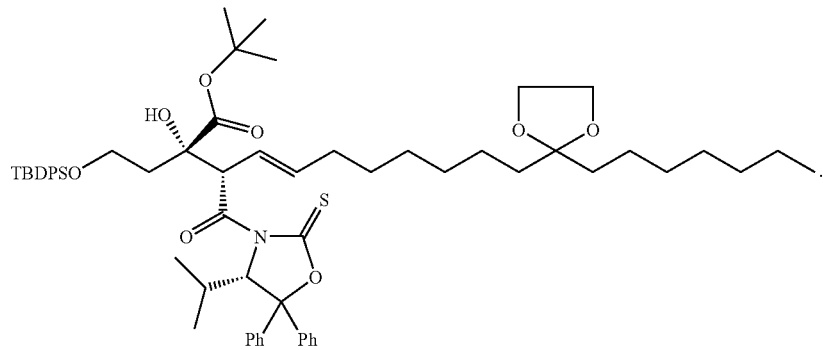

24

An anhydrous tetrahydrofuran solution (2.1 mL) of Compound 7 (204 mg, 0.329 mmol) synthesized in Example 1 and lithium chloride (42 mg, 0.99 mmol) was cooled to −78° C., and lithium hexamethyldisilazide (0.35 mL, 0.35 mmol, 1M hexane solution) was added, followed by stirring for 1.5 hours. An anhydrous tetrahydrofuran solution (1.4 mL) of Compound 19 (149 mg, 0.36 mmol) synthesized in Step 5-5 of Example 5 was added dropwise, followed by stirring for 30 minutes, and the addition of acetic acid (0.05 mL, 0.88 mmol). An aqueous ammonium chloride solution was added, followed by extraction with ethyl acetate. The organic layer was dried over anhydrous sodium sulfate, and concentrated under reduced pressure to obtain crudely purified Compound 24 (382 mg) as an oily substance. The crudely purified Compound 24 was used as it is for the next reaction.

9-9 (Step 7-2)

with water, followed by drying over anhydrous sodium sulfate. Concentration under reduced pressure afforded crudely purified Compound 26 (232 mg) as an oily substance. To an acetonitrile (1 mL) solution of the obtained crudely purified Compound 26 (125 mg), dicyclohexylamine (27.1 mg) and a seed crystal (Compound 31) were added, followed by stirring at −20° C. for 2 hours, at 0° C. for 1 hour, and at 5° C. for 12 hours. The precipitated solid was filtered off below 5° C. to obtain a white solid (71.9 mg). Recrystallization with acetonitrile afforded Compound 31 (61.6 mg) of a white solid. The crystallinity of Compound 26 was improved by forming a salt together with a base such as DCHA used in the present step, which enabled purification by means of recrystallization

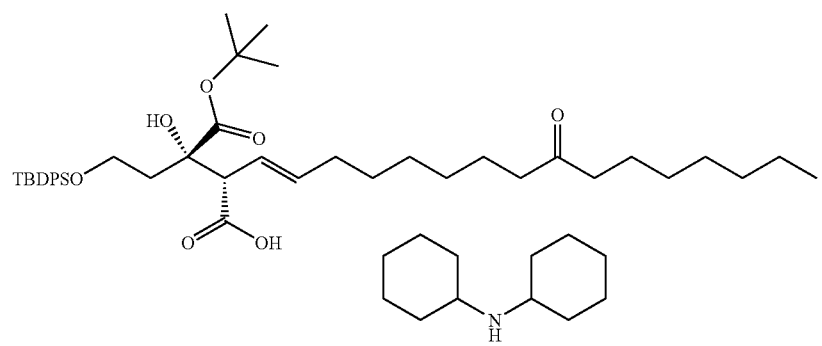

31

A tetrahydrofuran solution (12 mL) of the crudely purified Compound 24 (382 mg) was cooled to −10° C., and a mixture of lithium hydroxide monohydrate (25 mg, 0.592 mmol), water (1.5 mL) and 34.5% hydrogen peroxide solution (0.195 mL) was added slowly, followed by stirring at the same temperature for 30 minutes, and 0° C. for 1.5 hours. To the reaction solution, a 5% aqueous sodium thiosulfate solution and a 0.05 M aqueous citric acid solution were added sequentially, followed by extraction with ethyl acetate. The organic layer was washed with water and brine, and dried over anhydrous sodium sulfate. Concentration under reduced pressure afforded 382 mg of an oily substance. To an acetonitrile (8.3 mL) solution of 376 mg of the obtained oil, a 0.5 M aqueous citric acid solution (3.32 mL) was added, followed by stirring at 50° C. for 2.5 hours. After returning the temperature of the reaction solution to room temperature, the reaction solution was extracted with hexane, and the organic layer was washed method, so that the purification by column chromatography as mentioned in Example 9-3 became unnecessary.

Physicochemical Property of Compound 31

ESI (LC/MS positive mode) 731 (M+Na$^+$)

$^1$H-NMR Chemical shift value δ (in deuterated chloroform): 0.87 (3H, t, J=7 Hz), 1.00 (9H, s), 1.23 (9H, s), 1.10-2.28 (42H, m), 2.32-2.40 (4H, m), 2.86-3.00 (2H, m), 3.10 (1H, d, J=9 Hz), 3.55-3.67 (1H, m), 3.92-4.04 (1H, m), 5.50-5.68 (2H, m), 7.26-7.68 (10H, m).

9-10 (Step 7-4)

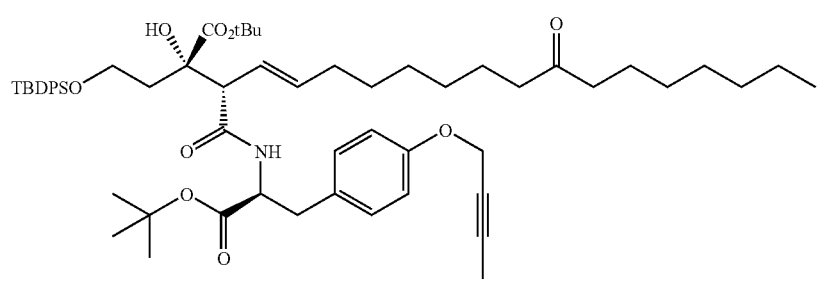

27

To a mixture of Compound 31 (862 mg, 0.968 mmol) and hexane (9 mL), a 0.5N aqueous potassium hydrogen sulfate solution (9 mL) was added followed by separation, followed by extraction with hexane (9 mL) from the aqueous layer. The combined organic layers were washed with water, and subsequently concentrated under reduced pressure to obtain crudely purified Compound 26 (701 mg) as an oily substance.

To an anhydrous N,N-dimethylformamide solution (17 mL) of the crudely purified Compound 26 (701 mg) and (S)-4-(2-butynyloxy)phenylalanine t-butyl ester hydrochloride (379 mg, 1.16 mmol), N,N-diisopropylethylamine (0.759 mL, 4.36 mmol) was added. The reaction solution was cooled to 0° C., and O-(7-azabenzotriazol-1-yl)-N,N,N',N'-tetramethyluronium hexafluorophosphate (405 mg, 1.07 mmol) was added, followed by stirring at the same temperature for 2 hours. A 0.5N aqueous potassium hydrogen sulfate solution and water were added to stop the reaction, followed by extraction with 20% ethyl acetate-hexane. The organic layer was washed with water and brine, and subsequently dried over anhydrous sodium sulfate. Concentration under reduced pressure afforded crudely purified Compound 27 (984 mg) as an oily substance. The crudely purified Compound 27 was used as it is for the next reaction.

9-11 (Step 7-5)

eridinyloxy free radical (41 mg, 0.194 mmol) and iodobenzene diacetate (842 mg, 2.61 mmol) were added sequentially, followed by stirring at room temperature for 2 hours, and water (2.7 mL) was added, followed by stirring further at room temperature for 30 minutes. To the reaction solution, 0.5 M aqueous citric acid solution and water were added, followed by extraction with 30% ethyl acetate-hexane. The organic layer was washed sequentially with a 5% aqueous sodium thiosulfate solution and water, and dried over anhydrous sodium sulfate. Concentration under reduced pressure afforded crudely purified Compound 29 (1.12 g) as an oily substance. The crudely purified Compound 29 (1.12 g) was dissolved in a mixed solution of t-butyl methyl ether (1.46 mL) and heptane (1.46 mL), and dicyclohexylamine (175 mg, 0.968 mmol), heptane (1.46 mL) and a seed crystal (Compound 32) were added, followed by stirring at 5° C. for 12 hours. The precipitated solid was filtered off to obtain a pale

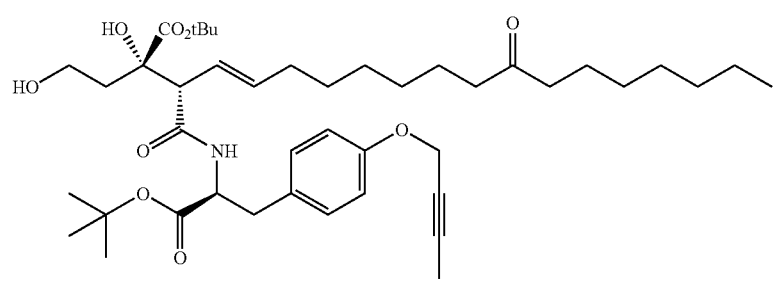

28

A tetrahydrofuran (9.5 mL) solution of the crudely purified Compound 27 (984 mg) was cooled to 0° C., and acetic acid (55 μL, 1.16 mmol) and tetrabutylammonium fluoride (1.16 mL, 1.16 mmol, 1.0 M tetrahydrofuran solution) were added sequentially, followed by stirring at room temperature for 1 hour. Water was added to the reaction solution, followed by extraction with 20% ethyl acetate-hexane. The organic layer was dried over anhydrous sodium sulfate, and subsequently concentrated under reduced pressure to obtain crudely purified Compound 28 (1.00 g) as an oily substance. The crudely purified Compound 28 was used as it is for the next reaction.

9-12 (Step 7-6)

yellow solid (762 mg), which was recrystallized with t-butyl methyl ether-heptane to obtain Compound 32 (717 mg). The crystallinity of Compound 29 was improved by forming a salt together with a base such as DCHA used in the present step, which enabled purification by means of recrystallization method, so that the purification by column chromatography as mentioned in Example 9-6 became unnecessary.

Physicochemical Property of Compound 32

ESI (LC/MS positive mode) 756 (M+H$^+$)

$^1$H-NMR Chemical shift value δ (in deuterated chloroform): 0.87 (3H, t, J=7 Hz), 1.12-2.05 (40H, m), 1.35 (9H, s), 1.39 (9H, s), 1.85 (3H, t, J=3 Hz), 2.32-2.40 (4H, m), 2.49

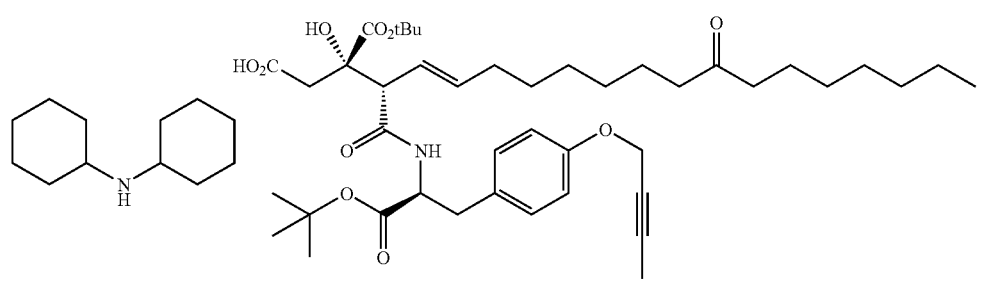

32

A mixed solution of the crudely purified Compound 28 (1.00 g) in acetonitrile (13.5 mL) and water (2.7 mL) was cooled to 0° C., and 4-acetamido-2,2,6,6-tetramethlyl-1-piperidinyloxy (1H, d, J=16 Hz), 2.66 (1H, d, J=16 Hz), 2.84-3.10 (4H, m), 3.15 (1H, d, J=9 Hz), 4.56-4.70 (3H, m), 5.50-5.70 (2H, m), 680-6.86 (2H, m), 7.08-7.16 (2H, m), 7.41 (1H, d, J=8 Hz)

9-13 (Step 7-7)

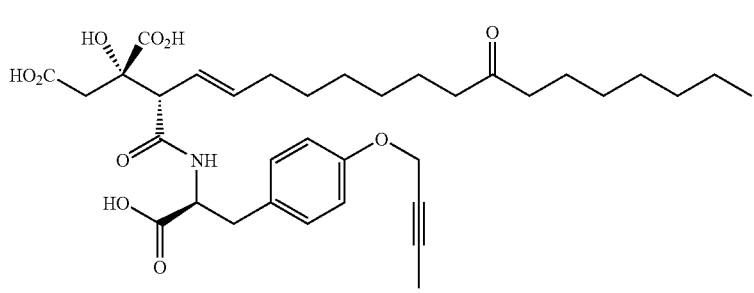

To a mixture of Compound 32 (108 mg, 0.115 mmol) and 20% ethyl acetate-hexane (1 mL), 0.5N aqueous potassium hydrogen sulfate (1 mL) was added followed by separation. The organic layer was washed with water, and concentrated under reduced pressure to obtain an oily substance. The dichloromethane solution (0.435 mL) of the present compound (88 mg) was cooled to 0° C., and a mixed solution of trifluoroacetic acid (0.696 mL) and water (0.174 mL) was added. After stirring at room temperature for 4 hours, concentration was carried out under reduced pressure, to obtain crudely purified 30 as an oily substance. To ethyl acetate solution (0.432 mL) of the crudely purified Compound 30, heptane (0.864 mL) and a seed crystal (Compound 30) were added, followed by stirring at room temperature for 2 hours. The precipitated solid was filtered off to obtain Compound 30 (65.4 mg).

9-14 (Step 7-1)

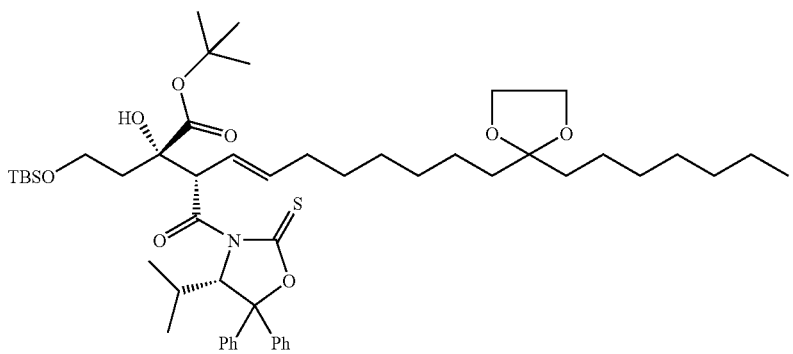

An anhydrous tetrahydrofuran solution (24.6 mL) of Compound 7 (2.37 g, 3.82 mmol) obtained in Example 1 and lithium chloride (1.21 g, 4.19 mmol) was cooled to −78° C., and lithium hexamethyldisilazide (3.75 mL, 4.01 mmol, 1.07 M hexane solution) was added, followed by stirring for 1 hour. The reaction solution was raised to −30° C., and stirred for 10 minutes. The reaction solution was cooled to −78° C., and an anhydrous tetrahydrofuran solution (16.4 mL) of Compound 15 (1.21 g, 4.19 mmol) synthesized in Example 3 was added dropwise over 30 minutes, followed by stirring for 20 minutes. Acetic acid (0.6 mL, 10.5 mmol) was added to stop the reaction, followed by stirring for 5 minutes. An aqueous ammonium chloride solution was added, followed by extraction with ethyl acetate. The organic layer was washed with brine, and dried over anhydrous sodium sulfate. Concentration under reduced pressure afforded crudely purified Compound 33 (3.70 g) as a yellow oily substance. The crudely purified Compound 33 was used as it is for the next reaction.

9-15 (Step 7-2)

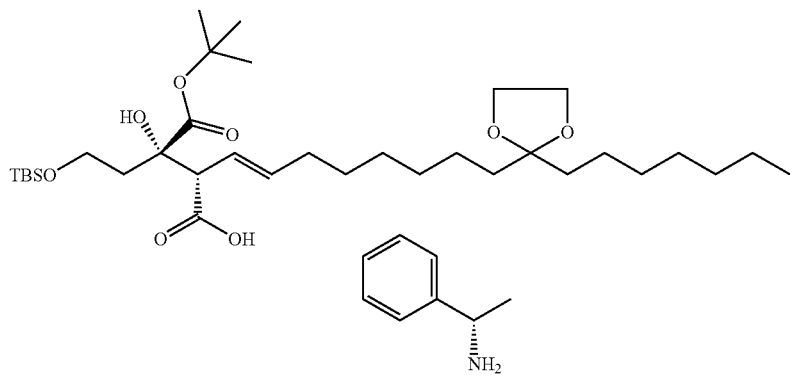

34

A tetrahydrofuran solution (86 mL) of the crudely purified Compound 33 (2.86 g) was cooled to −10° C., and a mixture of lithium hydroxide monohydrate (238 mg, 5.67 mmol), water (14 mL) and a 35% hydrogen peroxide solution (1.9 mL) was added slowly. Stirring was carried out at the same temperature for 30 minutes, at 0° C. for 1.5 hours. To the reaction solution, a 5% aqueous sodium thiosulfate solution, ethyl acetate, and a 0.025 M aqueous citric acid solution were added sequentially, followed by extraction. The organic layer was washed with water and brine, and dried over anhydrous sodium sulfate. Concentration under reduced pressure afforded a yellow oily substance. To an acetonitrile (15.9 mL) solution of the present compound (1.06 g), 2.65 mL of an acetonitrile (5.3 mL) solution of (S)-(−)-phenylethylamine (143 mg, 1.18 mmol) and a seed crystal (Compound 34) were added, followed by stirring at room temperature for 30 minutes. The remaining 2.65 mL of the acetonitrile (5.3 mL) solution of (S)-(−)-phenylethylamine (143 mg, 1.18 mmol) was added, followed by stirring at the same temperature for 1 hour. The precipitated solid was filtered off to obtain Compound 34 (472 mg) as a white solid. The Compound 34 is (S)-(−)-phenylethylamine salt of the carboxylic acid, and the crystallinity thereof was enhanced by forming such salt, which enabled purification by means of recrystallization method.

Physicochemical Property of Compound 34
ESI (LC/MS positive mode) 651 (M+Na$^+$)
$^1$H-NMR Chemical shift value δ (in deuterated chloroform): 0.05 (6H, s), 0.88 (3H, t, J=7 Hz), 0.89 (9H, s), 1.27-1.57 (34H, m), 1.93-2.04 (4H, m), 3.24 (1H, d, J=9 Hz), 3.68-3.83 (2H, m), 3.91 (4H, s), 4.19 (1H, q, J=7 Hz), 5.51-5.67 (2H, m), 7.25-7.38 (5H, m)

9-16 (Steps 7-2 and 7-4)

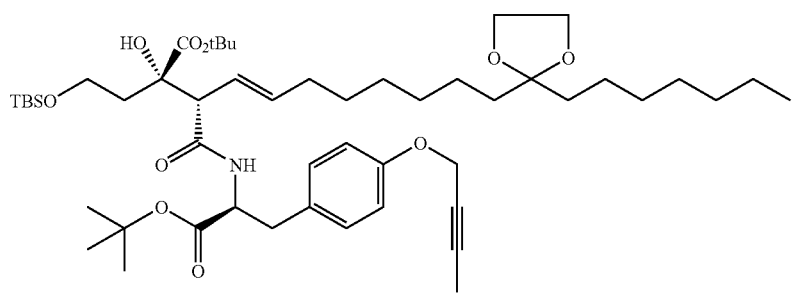

35

Using the above Compound 34 (180 mg, 0.24 mmol) as a starting material, analogously to Example 9-10, crudely purified Compound 35 (208 mg) was obtained as an oily substance. The crudely purified Compound 35 was used as it is for the next reaction.

9-17 (Step 7-5)

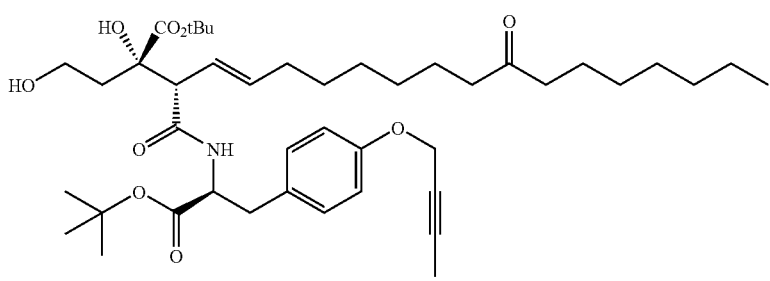

28

To an acetonitrile solution (2 mL) of the above crudely purified Compound 35 (200 mg), a 0.5 M aqueous citric acid solution (0.8 mL) was added, followed by stirring at 50° C. for 1 hour, and at 60° C. for 2 hours. After returning the temperature of the mixture to room temperature, water was added, followed by extraction with 20% ethyl acetate-hexane. The organic layer was dried over anhydrous sodium sulfate, and subsequently concentrated under reduced pressure, to obtain crudely purified Compound 7 (158 mg) as an oily substance. The crudely purified Compound 28 was used as it is for the next reaction.

9-18 (Step 7-6)

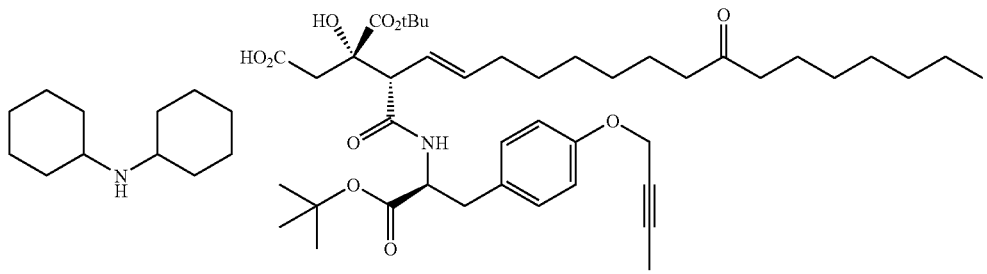

32

Using the above crudely purified Compound 28 (153 mg) as a starting material, analogously to Example 9-12, an oxidation reaction was carried out to obtain crudely purified carboxylic acid (153 mg). Analogously to Example 9-12, salt crystallization was carried out to obtain Compound 32 (149 mg) as a pale yellow solid. The present compound was identical with the compound obtained in Example 9-12.

9-19 (Step 7-3)

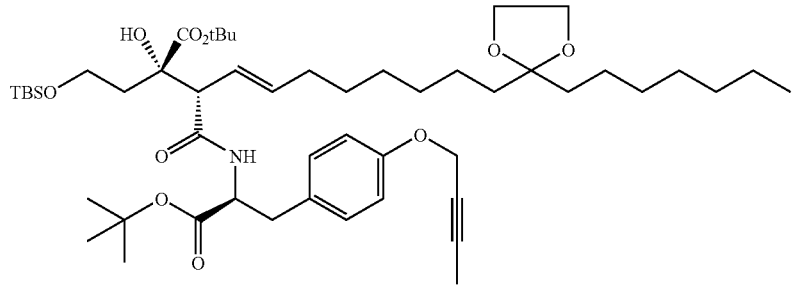

35

To an acetonitrile (0.7 mL) suspension of Compound 33 (1.25 g, 1.34 mmol) synthesized in Example 9-14, (S)-4-(2-butynyl)oxyphenylalanine t-butyl ester hydrochloride (481 mg, 1.48 mmol) and N,N-diisopropylethylamine (0.55 mL, 3.1 mmol) were added, which was heated to an outside temperature of 50 to 60° C., followed by stirring for 6 days. To the reaction mixture, acetonitrile (16 mL) and water (1 mL) were added, followed by extraction with hexane (3×40 mL). To the combined organic layers, ethyl acetate (12 mL) was added, followed by washing sequentially with a 0.5N aqueous potassium hydrogen sulfate solution (12.5 mL)-water (40 mL), water (80 mL) and brine (80 mL). The organic layer was dried over anhydrous magnesium sulfate, and the solvents were distilled off. The resulting residue was dissolved in hexane (80 mL), and washed with acetonitrile (20 mL)-water (2.4 mL), and further the washings were extracted with hexane (80 mL). The solvent was distilled off from the combined organic layer to obtain crudely purified Compound 35 (1.138 g) as a yellow oily substance. The obtained Compound 35 was used as it is for the next reaction.

9-20 (Step 7-5)

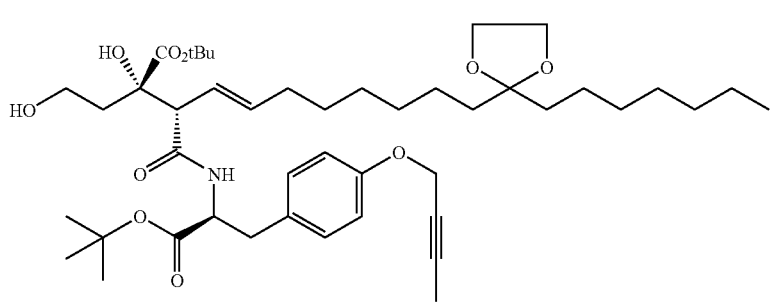

36

To a solution of tetrahydrofuran (6.8 mL) of Compound 35 (1.138 g), a tetrahydrofuran (3.4 mL) solution of acetic acid (102 mg, 1.70 mmol) and a tetrahydrofuran solution (1M, 1.7 mL, 1.7 mmol) of tetrabutylammonium fluoride were added at 0° C., followed by stirring at the same temperature for 30 minutes and at room temperature for 30 minutes. Water (20 mL) was added to the reaction mixture, and extracted with hexane (32 mL)-ethyl acetate (18 mL). The organic layer was washed with an aqueous diluted sodium hydrogen carbonate solution (25 ml, adjusted to pH 7). After the organic layer was dried over anhydrous magnesium sulfate, the solvent was distilled off, to obtain Compound 36 (1.046 g) as a yellow oily substance. The obtained Compound 36 was used as it is for the next reaction.

9-21 (Step 7-6)

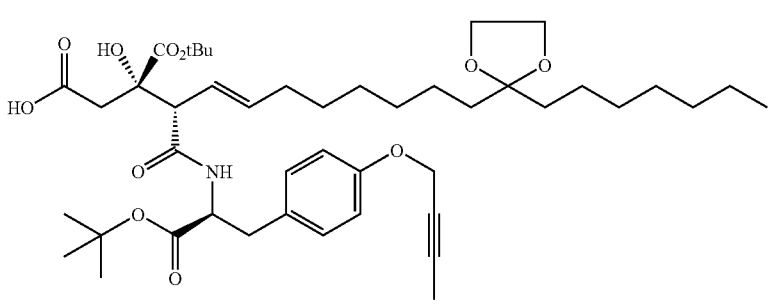

37

To an cetonitrile (16 mL)-water (3.5 mL) solution of Compound 36 (1.046 g), 4-acetamido-2,2,6,6,-tetramethylpiperidine 1-oxyl (57 mg, 0.27 mmol) and iodobenzene diacetate (1.18 g, 3.66 mmol) were added at 0° C., followed by stirring at room temperature. 2 hours later, water (3.2 mL) was added to the reaction mixture, which was further stirred at room temperature for 12 hours. The reaction mixture was extracted with hexane (27 mL)-ethyl acetate (27 mL), and washed sequentially with a 0.5 M aqueous citric acid solution (12 mL), water (12 mL), a 5% aqueous sodium thiosulfate solution (12 mL) and brine (12 mL). The organic layer was dried over anhydrous magnesium sulfate, and subsequently the solvent was distilled off, to obtain Compound 37 (1.27 g) as a light brown oily substance.

9-22 (Step 7-6)

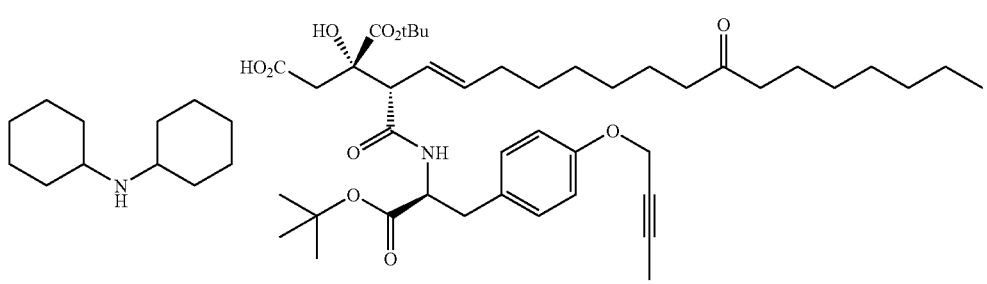

32

To an acetonitrile (11 mL) solution of Compound 37 (1.27 g), a 0.5 M aqueous citric acid solution (4.4 mL) was added, which was heated to an outside temperature of 55 to 65° C., followed by stirring for 2 hours. The reaction mixture was extracted with hexane (24 mL)-ethyl acetate (15 mL), and washed sequentially with water (11 mL), and then with brine (11 mL). The organic layer was dried over anhydrous magnesium sulfate, and subsequently the solvents were distilled off, to obtain crudely purified Compound 32-free form (1.05 g) as a light brown oily substance.

To a solution of Compound 32-free form (1.05 g) in heptane (1.9 mL)-methyl-t-butyl ether (1.9 mL), dicyclohexylamine (254 µL, 1.27 mmol) was added at room temperature, followed by stirring, and further heptane (5.7 mL) was added, followed by stirring at 5° C. over night. The precipitated crystal was collected by filteration with suction, washed with heptane, to obtain Compound 32 (903 mg) as a pale yellow solid.

The present compound was identical with the compound obtained in Example 9-12.

Example 10

Synthesis of Compound 41

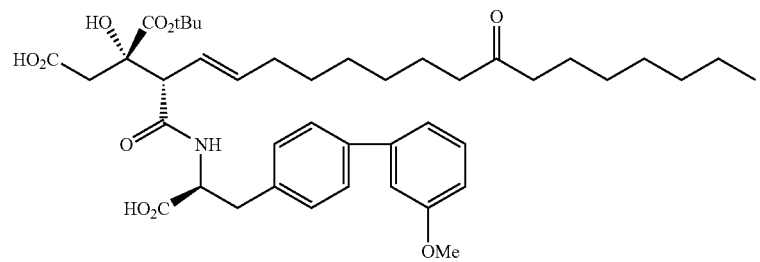

10-1 (Step 7-4):

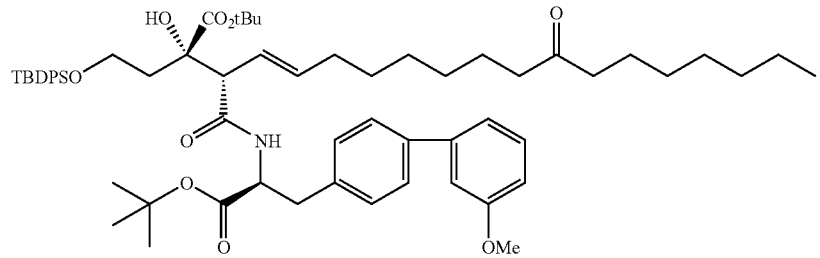

To an anhydrous N,N-dimethylformamide solution (54 mL) of Compound 26 (1.92 g, 2.71 mmol) synthesized in Example 9-3 and (S)-4-(3-methoxyphenyl)phenylalanine t-butyl ester hydrochloride (1.18 g, 3.24 mmol), N,N-diisopropylethylamine (2.12 mL, 12.2 mmol) was added. The reaction solution was cooled to 0° C., and O-(7-azabenzotriazol-1-yl)-N,N,N',N'-tetramethyluronium hexafluorophosphate (1.13 g, 2.97 mmol) was added, followed by stirring at the same temperature for 1 hour. Water was added to stop the reaction, followed by extraction with ethyl acetate. The organic layer was washed with brine, and subsequently dried over anhydrous sodium sulfate. A resulting crude product obtained through concentration under reduced pressure was purified by column chromatography (silica gel, hexane-ethyl acetate 4:1) to obtain Compound 38 (2.38 g) as a colorless oily substance.

Physicochemical Property of Compound 38

ESI (LC/MS positive mode) 1040 (M+Na$^+$)

$^1$H-NMR Chemical shift value δ (in deuterated chloroform): 0.87 (3H, t, J=7 Hz), 1.03 (9H, s), 1.17-1.59 (36H, m), 1.93-2.16 (4H, m), 2.31-2.38 (4H, m), 3.05-3.22 (3H, m), 3.55-3.63 (1H, m), 3.74-3.82 (1H, m), 3.84 (3H, s), 4.35 (1H, s), 4.74-4.80 (1H, m), 5.51 (1H, dd, J=9, 15 Hz), 5.64 (1H, dt, J=6, 15 Hz), 6.85-6.89 (1H, m), 7.05-7.12 (3H, m), 7.28-7.46 (10H, m), 7.61-7.65 (4H, m)

10-2 (Step 7-5)

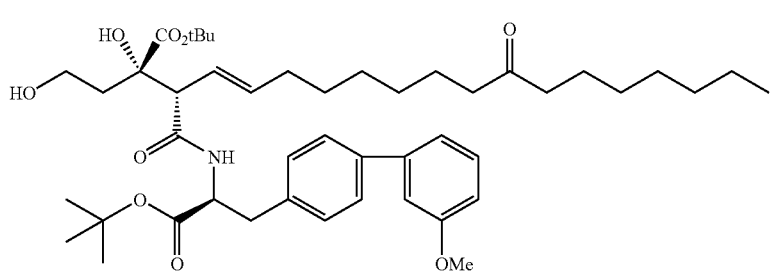

39

A tetrahydrofuran solution (26 mL) of Compound 38 (2.24 g, 2.20 mmol) was cooled to 0° C., and acetic acid (0.38 mL, 6.61 mmol) and tetrabutylammonium fluoride (6.61 mL, 6.61 mmol, 1.0 M tetrahydrofuran solution) were added sequentially, followed by stirring at room temperature for 1 hour. Water was added to the reaction solution, followed by extraction with ethyl acetate. The organic layer was washed with a saturated aqueous sodium hydrogencarbonate solution and brine, and subsequently dried over anhydrous sodium sulfate. A resulting crude product obtained through concentration under reduced pressure was purified by column chromatography (silica gel, hexane-ethyl acetate 1:1) to obtain Compound 39 (1.61 g) as a colorless oily substance.

Physicochemical Property of Compound 39

ESI (LC/MS positive mode) 780 (M+H$^+$)

$^1$H-NMR Chemical shift value δ (in deuterated chloroform): 0.87 (3H, t, J=7 Hz), 1.17-1.59 (35H, m), 1.63-1.75 (1H, m), 1.89-2.11 (4H, m), 2.32-2.39 (4H, m), 3.05-3.20 (3H, m), 3.55-3.67 (2H, m), 3.86 (3H, s), 4.47 (1H, s), 4.74-4.81 (1H, m), 5.51 (1H, dd, J=9, 15 Hz), 5.66 (1H, dt, J=6, 15 Hz), 6.86-6.91 (2H, m), 7.09-7.37 (4H, m), 7.48-7.52 (2H, m)

10-3 (Step 7-6)

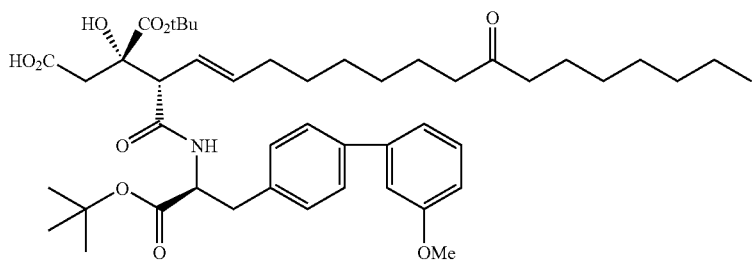

40

A mixed solution of Compound 39 (516 mg, 0.622 mmol) in acetonitrile (8.4 mL) and water (1.68 mL) was cooled to 0° C., and 2,2,6,6-tetramethyl-1-piperidinyloxy free radical (20.7 mg, 0.132 mmol) and iodobenzene diacetate (575 mg, 1.79 mmol) were added sequentially, followed by stirring at room temperature for 3.5 hours. To the reaction solution, ethyl acetate and a 10% aqueous citric acid solution were added, followed by extraction. The organic layer was washed sequentially with water, a 10% aqueous sodium thiosulfate solution and brine, and dried over anhydrous sodium sulfate. A crude product obtained through concentration under reduced pressure was purified by column chromatography (Bond Elute Diol, Varian, Inc., hexane-ethyl acetate 4:1 to 7:3) to obtain Compound 40 (456 mg) as a colorless oily substance.

Physicochemical Property of Compound 40

ESI (LC/MS positive mode) 816 (M+Na$^+$)

$^1$H-NMR Chemical shift value δ (in deuterated chloroform): 0.87 (3H, t, J=7 Hz), 1.17-1.62 (36H, m), 1.95-2.02 (2H, m), 2.32-2.39 (4H, m), 2.61 (1H, d, J=16 Hz), 2.84 (1H, d, J=16 Hz), 3.06-3.21 (3H, m), 3.55-3.67 (2H, m), 3.85 (3H, s), 4.72-4.78 (1H, m), 5.49 (1H, dd, J=9, 15 Hz), 5.68 (1H, dt, J=7, 15 Hz), 6.86-6.93 (2H, m), 7.08-7.36 (4H, m), 7.48-7.51 (2H, m)

10-4 (Step 7-7)

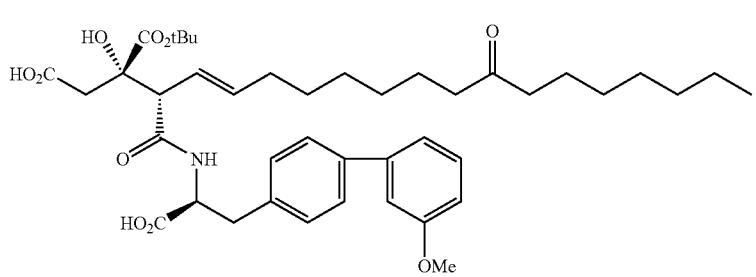

41

After a dichloromethane solution (0.43 mL) of Compound 40 (43 mg, 0.0541 mmol) was cooled to 0° C., a mixed solution of trifluoroacetic acid (0.34 mL) and water (0.086 mL) was added. After stirring at room temperature for 2.5 hours, concentration was carried out under reduced pressure. To a crude product obtained through concentration under reduced pressure, diisopropyl ether was added, followed by crystallization. The precipitated solid was filtered off to obtain Compound 41 (20 mg) as a white solid.
Physicochemical Property of Compound 41
ESI (LC/MS positive mode) 682 (M+H$^+$)
$^1$H-NMR Chemical shift value δ (in deuterated chloroform): 0.86 (3H, t, J=7 Hz), 1.04-1.56 (17H, m), 1.88 (2H, m), 2.27-2.36 (4H, m), 2.74-2.80 (1H, m), 2.98-3.10 (2H, m), 3.24-3.34 (2H, m), 3.56-3.73 (1H, m), 3.81 (3H, s), 4.74 (1H, m), 5.39-5.62 (2H, m), 6.83-6.86 (2H, m), 7.06-7.31 (4H, m), 7.44-7.56 (3H, m)
10-5 (Step 7-4)

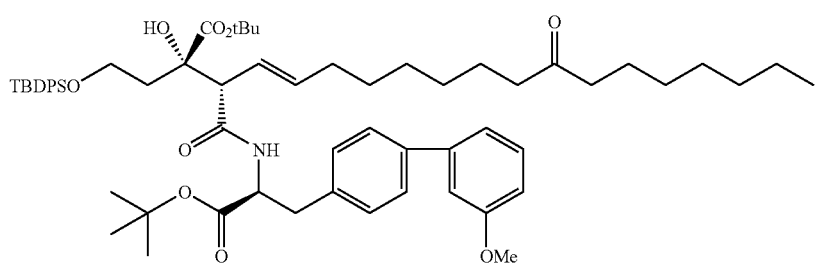

38

To a mixture of Compound 31 (872 mg, 0.979 mmol) synthesized in Example 9-9 and hexane (8.7 mL), a 0.5N aqueous potassium hydrogensulfate solution (8.7 mL) was added followed by separation. The organic layer was washed with water, and subsequently concentrated under reduced pressure, to obtain crudely purified Compound 26 (640 mg) as a yellow oily substance. To an anhydrous N,N-dimethylformamide solution (17.4 mL) of the crudely purified compound 26 (640 mg) and (S)-4-(3-methoxyphenyl)phenylalanine t-butyl ester hydrochloride (428 mg, 1.18 mmol), N,N-diisopropylethylamine (0.768 mL, 4.41 mmol) was added. The reaction solution was cooled to 0° C., and O-(7-azabenzotriazol-1-yl)-N,N,N',N'-tetramethyluronium hexafluorophosphate (410 mg, 1.08 mmol) was added, followed by stirring at the same temperature for 1 hour. A 0.5N aqueous potassium hydrogensulfate solution and water were added to stop the reaction, followed by extraction with 20% ethyl acetate-hexane. The organic layer was washed with water and brine, and subsequently dried over anhydrous sodium sulfate. Concentration under reduced pressure afforded crudely purified Compound 38 (1.00 g) as a yellow oily substance. The crudely purified Compound 38 was used as it is for the next reaction.
10-6 (Step 7-5)

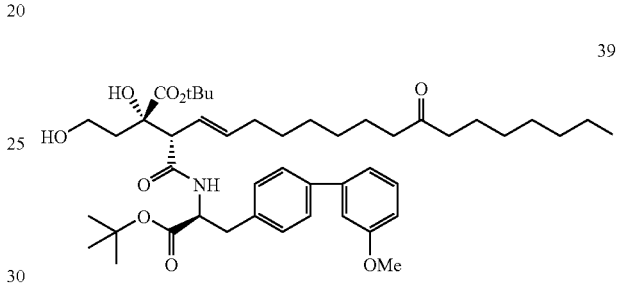

39

A tetrahydrofuran solution (9.13 mL) of the crudely purified Compound 38 (913 mg) was cooled to 0° C., and acetic acid (51 µL, 1.08 mmol) and tetrabutylammonium fluoride (1.08 mL, 1.08 mmol, 1.0 M tetrahydrofuran solution) were added sequentially, followed by stirring at room temperature for 1 hour. Water was added to the reaction solution, followed by extraction with 20% ethyl acetate-hexane. The organic layer was dried over anhydrous sodium sulfate, and subsequently concentrated under reduced pressure to obtain crudely purified Compound 39 (913 mg) as a yellow oily substance. The crudely purified Compound 39 was used as it is for the next reaction.
10-7 (Step 7-6)

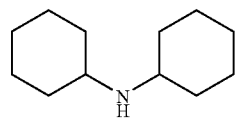

42

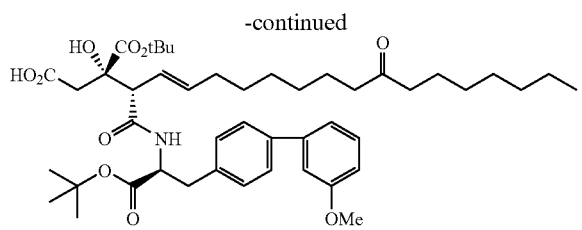

A mixed solution of the crudely purified Compound 39 (913 mg) in acetonitrile (13.7 mL) and water (2.74 mL) was cooled to 0° C., and 4-acetamido-2,2,6,6-tetramethyl-1-piperidinyloxy free radical (49.9 mg, 0.234 mmol) and iodobenzene diacetate (1.02 g, 3.17 mmol) were added sequentially, followed by stirring at room temperature for 2 hours. To the reaction solution, 20% ethyl acetate-hexane, a 0.5 M aqueous citric acid solution and water were added, followed by extraction. The organic layer was washed sequentially with a 5% aqueous sodium thiosulfate solution and water, and dried over anhydrous sodium sulfate. Concentration under reduced pressure afforded a crudely purified product (983 mg) as a yellow oily substance. To an acetonitrile (9.83 mL) solution of the present crude purified product (983 mg), dicyclohexylamine (247 μL, 1.24 mmol) and a seed crystal were added, followed by stirring at room temperature for 30 minutes and at 0° C. for 2 hours. The precipitated solid was filtered off to obtain Compound 42 (602 mg) as a pale yellow solid. The crystallinity of Compound 40 was improved by forming a salt together with a base such as DCHA used in the present step, which enabled purification by means of recrystallization method, so that the purification by column chromatography as mentioned in Example 10-3 became unnecessary.

Physicochemical Property of Compound 42

ESI (LC/MS positive mode) 794 (M+H$^+$-dicyclohexylamine)

$^1$H-NMR Chemical shift value δ (in deuterated chloroform): 0.87 (3H, t, J=7 Hz), 1.10-1.98 (58H, m), 2.32-2.38 (4H, m), 2.53 (1H, d, J=16 Hz), 2.68 (1H, d, J=16 Hz), 2.85-2.93 (2H, m), 3.02-3.20 (3H, m), 3.85 (3H, s), 4.67-4.74 (1H, m), 5.56-5.64 (2H, m), 6.85-6.88 (1H, m), 7.09-7.19 (2H, m), 7.29-7.32 (2H, m), 7.44-7.50 (3H, m)

10-8 (Step 7-7)

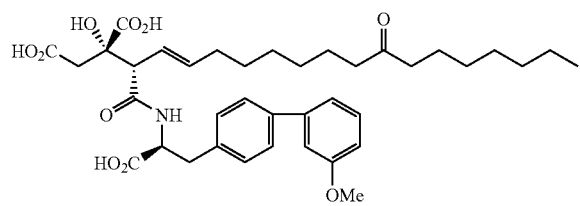

To a mixture of Compound 42 (480 mg, 0.492 mmol) and 20% ethyl acetate-hexane (19.2 mL), a 0.5N aqueous potassium hydrogensulfate solution (19.2 mL) was added followed by separation. The organic layer was washed with water, and concentrated under reduced pressure, to obtain crudely purified Compound 40 (395 mg) as a yellow oily substance. After an anisole solution (2.1 mL) of the crudely purified Compound 40 (395 mg) was cooled to 0° C., a mixed solution of trifluoroacetic acid (7.2 mL) and water (0.72 mL) was added. After stirring at room temperature for 2.5 hours, concentration was carried out under reduced pressure, to obtain crudely purified Compound 41 (376 mg) as a brown oily substance. To an acetonitrile solution (0.376 mL) of the crudely purified Compound 41 (376 mg), diisopropyl ether (3.76 mL) and a seed crystal were added, followed by stirring at room temperature for 1 hour and at 0° C. for 1 hour. The precipitated solid was filtered off to obtain Compound 41 (301 mg) as a pale yellow solid.

10-9 (Step 7-4)

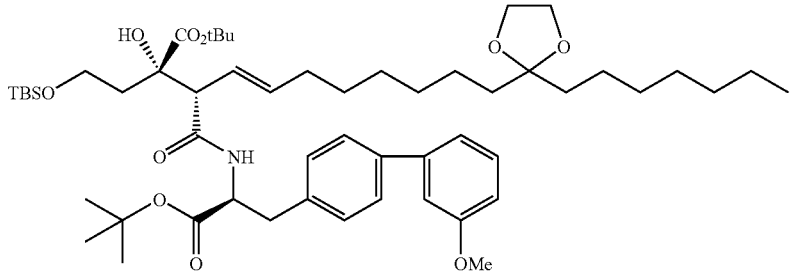

Using Compound 34 (178 mg, 0.237 mmol) synthesized in Example 9-15 as a starting material, analogously to Example 9-10, crudely purified Compound 43 (226 mg) was obtained as a yellow oily substance. The crudely purified compound 43 was used as it is for the next reaction.

10-10 (Step 7-5)

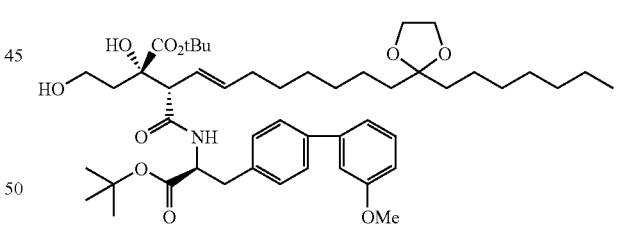

Using the crudely purified Compound 43 (190 mg) as a starting material, analogously to Example 10-2, crudely purified Compound 44 (169 mg) was obtained as a yellow oily substance. The crudely purified compound 44 was used as it is for the next reaction.

10-11 (Step 7-6)

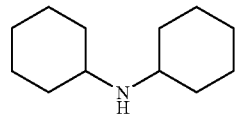

83

-continued

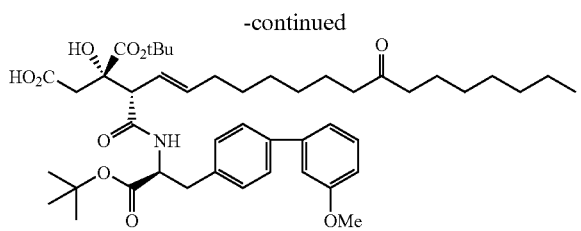

Using the above crudely purified Compound 44 (169 mg) as a starting material, analogously to Example 10-7, an oxidation reaction was carried out to obtain crudely purified compound (175 mg). To an acetonitrile solution (1.56 mL) of the crudely purified compound (173 mg), a 0.5 M aqueous citric acid solution (0.52 mL) was added, followed by stirring at 60° C. for 3 hours. The reaction solution was extracted with 20% ethyl acetate-hexane. The organic layer was washed with water, and dried over anhydrous sodium sulfate. Concentration under reduced pressure afforded a crudely purified product (162 mg) as a yellow oily substance. Salt crystallization was carried out using the crudely purified product (160 mg), analogously to Example 10-7, to obtain Compound 42 as a pale yellow solid.

The present compound was identical with the compound obtained in Example 10-7.

10-12 (Step 7-3)

45

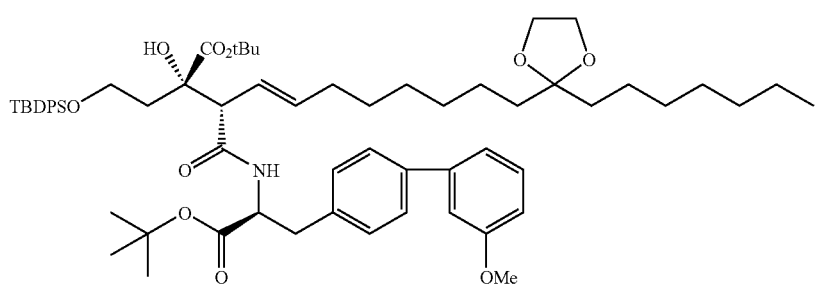

Under a nitrogen atmosphere, Compound 24 (2.07 g, 2.75 mmol) synthesized in Example 9-1 was dissolved in dehydrated dimethylformamide (150 mL), and (S)-4-(3-methoxyphenyl)phenylalanine t-butyl ester hydrochloride (1.20 g, 3.30 mmol) and diisopropylethylamine (1.60 g, 12.38 mmol) were added. Subsequently, HATU (O-7-azabenzotriazol-1-yl)-N,N,N',N'-tetramethyluronium hexafluorophosphate) (1.15 g, 3.03 mmol) was added, followed by stirring for 1 hour while maintaining ice cooling. Water and ethyl acetate were added, followed by separation, and the aqueous layer was extracted with ethyl acetate. The organic layers were combined, and washed with brine. Subsequently, drying over anhydrous sodium sulfate was carried out, followed by concentration under reduced pressure to obtain crudely purified title Compound 46 as a yellow oily substance. Purification by column chromatography (silica gel, hexane-ethyl acetate 4:1) afforded Compound 45 (2.57 g, 2.42 mmol) as a colorless oily substance.

Physicochemical property of Compound 45

Molecular weight: 1062

LC-MS (FINNIGAN LCQ+HPLC system HEWLETT PACKARD series 1100) 1085 (M+Na⁺)

¹H-NMR Chemical shift value δ (in deuterated chloroform): 0.87 (3H, J=6.3 Hz, t), 1.02 (9H, s), 1.26 (18H, m), 1.30 (9H, s), 1.38 (9H, s), 1.54 (4H, m), 1.93-2.13 (4H, m),

84

3.05-3.21 (2H, m), 3.54-3.62 (1H, m), 3.74-3.88 (2H, m), 3.84 (3H, s), 3.90 (4H, s), 4.34 (1H, s), 4.77 (1H, J=7.8, 6.3, 6.3 Hz, ddd), 5.51 (1H, J=15.3, 9.3 Hz, dd), 5.64 (1H, 15.3, 6.3, 6.3 Hz, ddd), 6.87 (1H, 8.4, 2.7, 0.9 Hz, ddd), 7.05-7.12 (3H, m), 7.25-7.46 (10H, m), 7.60-7.64 (4H, m)

10-13 (Step 7-5)

44

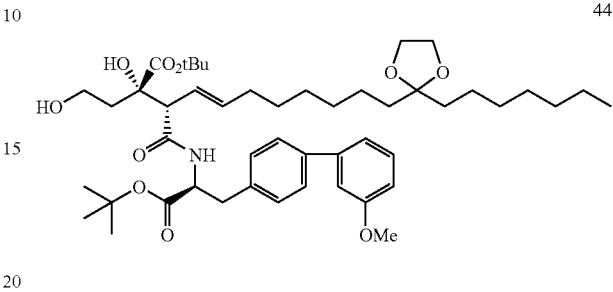

Under a nitrogen atmosphere, Compound 44 (2.43 g, 2.32 mmol) was dissolved in dehydrated tetrahydrofuran (25 mL), and under ice cooling acetic acid (417 mg, 6.95 mmol) and tetrabutylammonium fluoride (1.0 M tetrahydrofuran solution, 6.95 mL, 6.95 mmol) were added, followed by stirring at room temperature for 1 hour. Water and ether were added, followed by separation. The organic layer was washed with a saturated aqueous sodium hydrogencarbonate solution and brine, and subsequently dried over anhydrous sodium sulfate, followed by concentration under reduced pressure to obtain crudely purified title Compound 45 as a slightly yellow oily substance. Purification by column chromatography (silica gel, hexane-ethyl acetate 4:1 to 2:3) afforded Compound 44 (1.93 g, 2.32 mmol) as a colorless oily substance.

Physicochemical Property of Compound 44

Molecular weight: 823

LC-MS (FINNIGAN LCQ+HPLC system HEWLETT PACKARD series 1100) 824 (M+H⁺)

¹H-NMR Chemical shift value δ (in deuterated chloroform): 0.88 (3H, J=7.2 Hz, t), 1.27 (18H, m), 1.30 (9H, s), 1.42 (9H, s), 1.47-1.75 (4H, m), 1.88-2.10 (4H, m), 3.05-3.20 (3H, m), 3.55-3.66 (2H, m), 3.86 (3H, s), 3.91 (4H, s), 4.46 (1H, s), 4.78 (1H, J=8.1, 6.6, 6.6 Hz, ddd), 5.51 (1H, J=15.2, 9.6 Hz, dd), 5.67 (1H, 15.2, 6.6, 6.6 Hz, ddd) 6.84-6.90 (2H, m), 7.09-7.17 (2H, m), 7.24-7.27 (1H, m), 7.32-7.37 (1H, m), 7.48-7.52 (2H, m)

10-14 (Step 7-6)

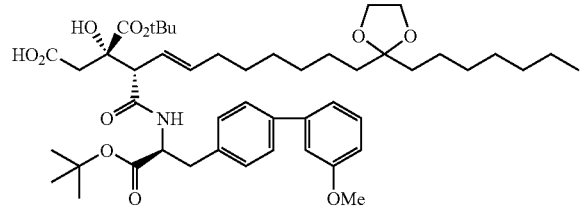

46

Under a nitrogen atmosphere, Compound 44 (530 mg, 0.643 mmol) was dissolved in dehydrated dimethylformamide (10 mL), followed by the addition of water (2 mL), and under ice cooling TEMPO (2,2,6,6-tetramethyl-1-piperidinyloxy, free radical) (20 mg, 0.129 mmol) and iodobenzene diacetate (559 mg, 1.74 mmol) were added, followed by stirring at room temperature for 7 hours. To the reaction solution, ethyl acetate and a 0.5 M aqueous citric acid solution were added, to be separated. The organic layer was washed twice with water and with brine, and subsequently dried over anhydrous sodium sulfate, followed by concentration under reduced pressure, to obtain crudely purified title Compound 46 as a khaki oily substance. Purification by column chromatography (diol column, hexane-ethyl acetate 4:1 to 1:1) afforded Compound 46 (389 mg, 0.464 mmol) as a yellow oily substance.

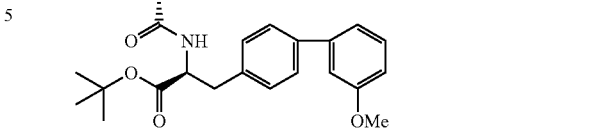

The compound 46 (214 mg, 0.255 mmol) was dissolved in acetonitrile, and at room temperature DCHA (dicyclohexylamine) (46.3 g, 0.255 mmol) was added, followed by stirring for 30 minutes. A crystal resulting from stirring under ice cooling for 1 hour was filtered off, whereby Compound 47 (152 mg, 0.149 mmol) was obtained as a pale yellow-green crystal. The crystallinity of Compound 46 was improved by forming a salt together with a base such as DCHA used in the present step, which enabled purification by means of recrystallization method, so that the purification by column chromatography as mentioned in Example 10-14 became unnecessary.

Physicochemical Property of Compound 47
Molecular weight: 1018
LC-MS (FINNIGAN LCQ+HPLC system HEWLETT PACKARD series 1100) 838 (M+H$^+$-DCHA)
$^1$H-NMR Chemical shift value δ (in deuterated chloroform): 0.87 (3H, J=7.2 Hz, t), 1.14-2.03 (44H, m), 1.37 (9H, s), 1.41 (9H, s), 2.52 (1H, J=15.8 Hz, d), 2.70 (1H, J=15.8 Hz, d), 2.78-2.88 (2H, m), 3.10-3.20 (3H, m), 3.86 (3H, s), 3.91 (4H, s), 4.69-4.77 (1H, m), 5.53-5.66 (2H, m), 6.85-6.88 (2H, m), 7.09-7.16 (2H, m), 7.26-7.32 (2H, m), 7.44-7.49 (2H, m)

10-16 (Step 7-3)

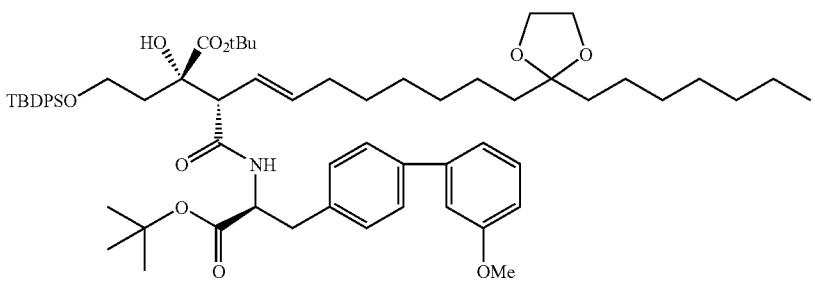

45

Physicochemical Property of Compound 46
Molecular weight: 837
LC-MS (FINNIGAN LCQ+HPLC system HEWLETT PACKARD series 1100) 838 (M+H$^+$)
$^1$H-NMR Chemical shift value δ (in deuterated chloroform): 0.87 (3H, J=6.6 Hz, t), 1.27 (18H, m), 1.42 (9H, s), 1.43 (9H, s), 1.46-1.64 (4H, m), 1.95-2.04 (2H, m), 2.58 (1H, J=15.8 Hz, d), 2.82 (1H, J=15.8 Hz, d), 3.06-3.24 (3H, m), 3.86 (3H, s), 3.91 (4H, s), 4.75 (1H, J=7.8, 6.5, 6.5 Hz, ddd), 5.49 (1H, J=15.3, 9.0 Hz, dd), 5.71 (1H, 15.3, 6.5, 6.5 Hz, ddd), 6.83-6.90 (2H, m), 7.08-7.16 (2H, m), 7.25-7.28 (1H, m), 7.31-7.36 (1H, m), 7.48-7.51 (2H, m)

10-15 (Step 7-6)

47

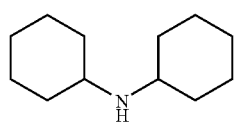

Under a nitrogen atmosphere, Compound 24 (338 mg, 0.327 mmol) synthesized in Example 9-1 was dissolved in dehydrated acetonitrile (0.5 mL), and (S)-4-(3-methoxyphenyl)phenylalanine t-butyl ester hydrochloride (131 mg, 0.360 mmol) and diisopropylethylamine (85 mg, 0.658 mmol) were added, which was stirred at an outside temperature of 50 to 60° C. for 23 hours, followed by concentration. Hexane was added and insolubles were removed, and the hexane layer was concentrated. The residue was dissolved in a mixed solution of hexane-ethyl acetate (10:1), to be separated with an aqueous potassium hydrogensulfate solution, water, a 5% aqueous sodium hydrogencarbonate solution and brine, and the organic layer was dried over anhydrous sodium sulfate, followed by concentration under reduced pressure, to obtain crudely purified yellow oily substance. The oily substance was dissolved in hexane (20 mL), washed with a mixed solution of acetonitrile (5 mL)-water (0.5 mL), and further the acetonitrile layer was extracted with hexane (20 mL). The hexane layers were combined, and dried over anhydrous sodium sulfate, followed by concentration under reduced pressure, to obtain 317 mg (0.298 mmol) of crudely purified title Compound 45 as a yellow oily substance.

The crudely purified Compound 45 was used as it is for the next reaction.

10-17 (Step 7-5)

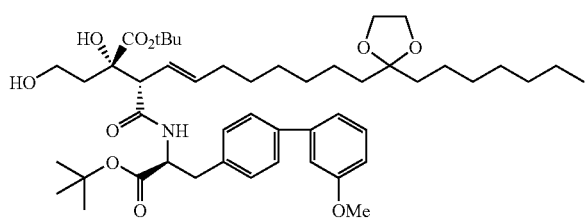
44

Under a nitrogen atmosphere, the crudely purified Compound 45 (317 mg, 0.298 mmol) was dissolved in dehydrated tetrahydrofuran (3 mL), and under ice cooling acetic acid (54 mg, 0.899 mmol) and tetrabutylammonium fluoride (1.0 M tetrahydrofuran solution, 0.90 mL, 0.900 mmol) were added, followed by stirring at room temperature for 2 hours. Water and ether were added, to be separated, and the organic layer was washed with a saturated aqueous sodium hydrogencarbonate solution and brine, and subsequently dried over anhydrous sodium sulfate, followed by concentration under reduced pressure, to obtain 294 mg of crudely purified title Compound 44 as a slightly yellow oily substance. The crudely purified Compound 44 was used as it is for the next reaction.

10-18 (Step 7-6)

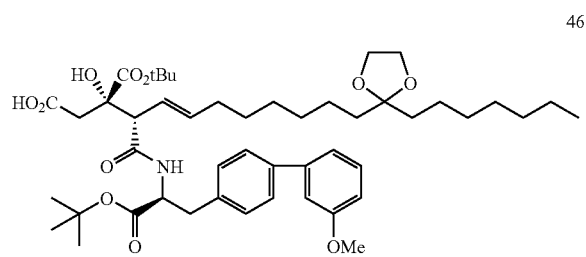
46

Under a nitrogen atmosphere, the crudely purified oily substance (Compound 44, 294 mg) was dissolved in dehydrated dimethylformamide (6 mL), followed by the addition of water (1 mL), and under ice cooling TEMPO (2,2,6,6-tetramethyl-1-piperidinyloxy, free radical) (13 mg, 0.0609 mmol) and iodobenzene diacetate (259 mg, 0.804 mmol) were added, followed by stirring at room temperature for 3 hours. To the reaction solution, ethyl acetate and a 0.5 M aqueous citric acid solution were added, to be separated. The organic layer was washed twice with water and with brine, and subsequently dried over anhydrous sodium sulfate, followed by concentration under reduced pressure, to obtain 324 mg of crudely purified title Compound 46 as a khaki oily substance. The crudely purified Compound 46 was used as it is for the next reaction.

10-19 (Step 7-6)

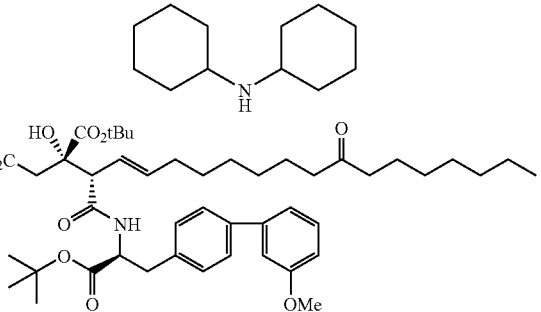
42

The crudely purified compound 46 (324 mg) was dissolved in acetonitrile (5 mL), and a 0.5 M aqueous citric acid solution (3 mL) was added, followed by stirring at an outside temperature of 50° C. for 2 and a half hours. The reaction solution was extracted with diethyl ether, and the organic layer was washed with water, water and brine and dried over anhydrous sodium sulfate, followed by concentration under reduced pressure, to obtain 299 mg of an oily substance.

The oily substance (299 mg) was dissolved in acetonitrile (3.0 mL), and at room temperature DCHA (dicyclohexylamine) (54 mg, 0.298 mmol) was added, followed by stirring for 30 minutes. A crystal resulting from stirring under ice cooling for 16 hours was filtered off, whereby Compound 42 (28 mg, 0.0287 mmol) was obtained as a pale yellow-green crystal.

The present compound was identical with the compound obtained in Example 10-7.

10-20 (Step 7-3)

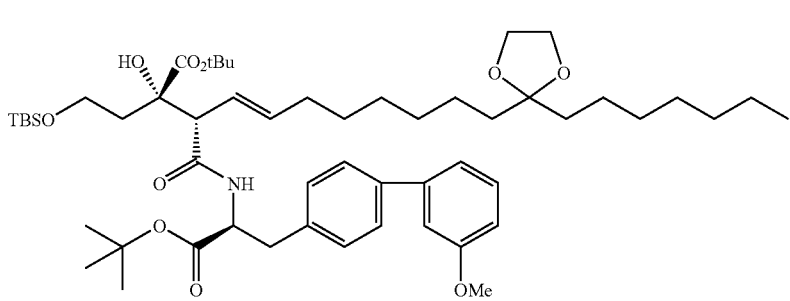
43

To an acetonitrile (0.13 mL) suspension of Compound 33 (296 mg, 0.326 mmol) synthesized in Example 9-14, (S)-4-(3-methoxyphenyl)phenylalanine t-butyl ester hydrochloride (128 mg, 0.352 mmol) and N,N-diisopropylethylamine (0.125 mL, 0.718 mmol) were added, which was heated to an outside temperature of 50 to 60° C., followed by stirring for 42 hours. To the reaction mixture, acetonitrile (4 mL) and water (0.25 mL) were added, followed by extraction with hexane (3×10 mL). To the combined organic layers, ethyl acetate (3 mL) was added, followed by washing sequentially with a 0.5N aqueous potassium hydrogensulfate solution (4 mL)-water (10 mL), water (20 mL) and brine (20 mL). The organic layer was dried over anhydrous magnesium sulfate, and the solvent was distilled off. The resulting residue was dissolved in hexane (20 mL), and washed with acetonitrile (5 mL)-water (0.6 mL), and further the washings were extracted with hexane (20 mL). The solvent of the combined organic layers was distilled off, whereby crudely purified title Compound 43 (294 mg) was obtained as a yellow oily substance. The obtained crudely purified product 43 was used as it is for the next reaction.

10-21 (Step 7-5)

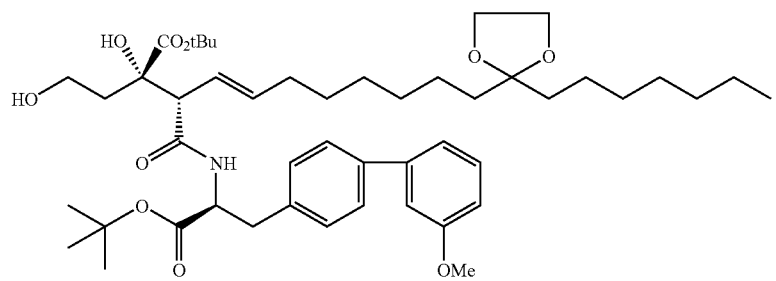

44

To a tetrahydrofuran (1.4 mL) solution of the crudely purified product 43 (293 mg), a tetrahydrofuran (0.7 mL) solution of acetic acid (21 mg, 0.35 mmol) and tetrahydrofuran solution (1M, 0.35 mL, 0.35 mmol) of tetrabutylammonium fluoride were added at 0° C., followed by stirring at the same temperature for 30 minutes, and at room temperature for 30 minutes. Water (4.2 mL) was added to the reaction mixture, followed by extraction with hexane (6.4 mL)-ethyl acetate (1.6 mL), and the organic layer was washed with a diluted aqueous sodium hydrogencarbonate solution (5 mL, adjusted to pH 7). After the organic layer was dried over anhydrous magnesium sulfate, the solvent was distilled off, to obtain Compound 44 (255 mg) as a yellow oily substance. The obtained crudely purified product 44 was used as it is for the next reaction.

10-22 (Step 7-6)

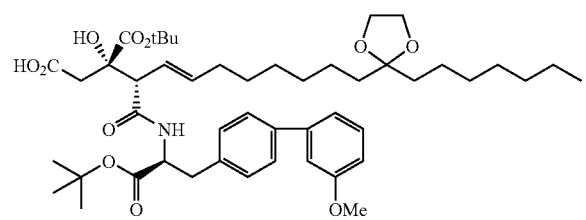

46

To an acetonitrile (3.6 mL)-water (0.74 mL) solution of the crudely purified product 44 (254 mg), 4-acetamido-2,2,6,6-tetramethylpiperidine 1-oxyl (13.7 mg, 0.064 mmol) and iodobenzene diacetate (266 mg, 0.826 mmol) were added at 0° C., followed by stirring at room temperature. 2 hours later, water (0.74 mL) was added to the reaction mixture, which was further stirred at room temperature for 5 hours. The reaction mixture was extracted with hexane (6 mL)-ethyl acetate (6 mL), and washed sequentially with a 0.5 M aqueous citric acid solution (2.8 mL), water (2.8 mL), a 5% aqueous sodium thiosulfate solution (2.8 mL) and brine (2.8 mL). The organic layer was dried over anhydrous magnesium sulfate, and subsequently the solvent was distilled off, to obtain crudely purified title Compound 46 (289 mg) as a yellow oily substance.

10-23 (Step 7-6)

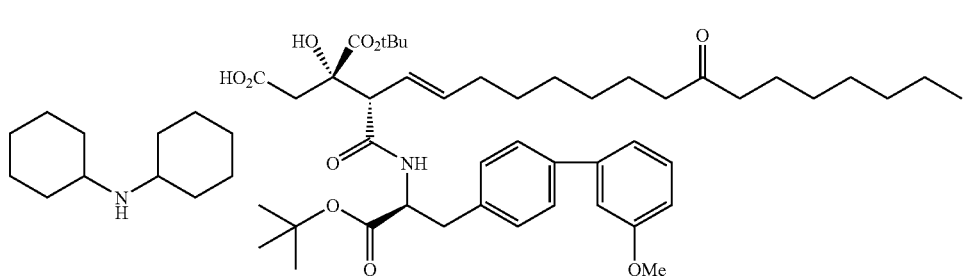

42

To an acetonitrile (2.4 mL) solution of the crudely purified product 46 (289 mg), a 0.5 M aqueous citric acid solution (0.8 mL) was added, which was heated to an outside temperature of 55 to 65° C., followed by stirring for 3 hours. The reaction mixture was extracted with hexane (5.3 mL)-ethyl acetate (2.7 mL), followed by washing sequentially with water (2.5 mL), and then brine (2.5 mL). After the organic layer was dried over anhydrous magnesium sulfate, the solvent was distilled off, whereby crudely purified 40 (247 mg) was obtained as a tan oily substance.

To an acetonitrile (2.4 mL) solution of the crudely purified product 40 (246 mg), dicyclohexylamine (62 μL, 0.30 mmol) was added, followed by stirring at 5° C. overnight. The precipitated crystal was collected by filteration with suction, followed by washing with acetonitrile cooled to 0° C., to obtain Compound 42 (169 mg) as a pale yellow solid.

The present compound was identical with the compound obtained in Example 10-7.

Example 11

Synthesis of Compound 51

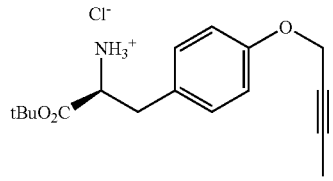

51

11-1 (Step 8-2)

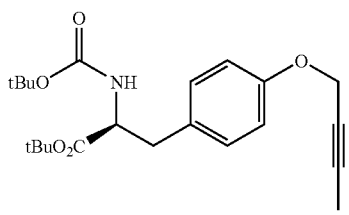

48

To an anhydrous N,N-dimethylformamide solution (2.0 mL) of N-t-butoxycarbonyl-L-tyrosine-t-butyl ester (338 mg, 1.0 mM), potassium carbonate (173 mg, 1.25 mM) and 1-bromo-2-butyne (147 mg, 1.1 mM) were added, followed by stirring at room temperature for 15 hours. Ethyl acetate (30 mL) was added to the reaction solution, followed by washing three times with water (20 mL) and with brine (20 mL) sequentially. The ethyl acetate layer was dehydrated and dried over anhydrous sodium sulfate, and the solvent was distilled off under reduced pressure. Subsequently, the resulting oily substance was purified by silica gel column chromatography. From n-hexane/ethyl acetate (5:1) eluted fraction, Compound 48 (370 mg, 95%) was obtained as a colorless oily substance.

Physicochemical Property of Compound 48

Molecular weight: 389

FAB-MS (positive mode, matrix m-NBA) 390 (M+H$^+$)

$^1$H-NMR Chemical shift value δ (in deuterated chloroform): 1.41 (9H, s), 1.42 (9H, s), 1.86 (3H, t, J=2.5 Hz), 3.00 (2H, d, J=6.0 Hz), 4.41 (1H, dd, J=7.5, 6.0 Hz), 4.62 (2H, q, J=2.5 Hz), 4.97 (1H, d, J=7.5 Hz), 6.88 (2H, d, J=8.5 Hz), 7.08 (2H, d, J=8.5 Hz)

11-2 (Step 8-3)

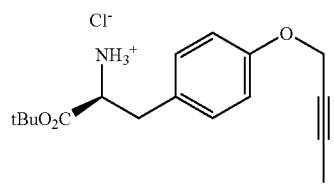

51

Compound 48 (390 mg, 1.0 mM) was dissolved in ethyl acetate (5.0 mL), and 4N hydrochloric acid/ethyl acetate (2.0 mL, 8.0 mM) was added, followed by stirring at room temperature for 15 hours. A precipitated powder was filtered off with a Kiriyama funnel, followed by washing with ethyl acetate (2.0 mL) and drying under reduced pressure with a vacuum pump, to obtain Compound 51 (278 mg, 85%) as a colorless powder.

Physicochemical Property of Compound 51

Molecular Weight: 289

ESI (LC/MS positive mode) 290 (M+H$^+$)

$^1$H-NMR Chemical shift value δ (in methanol d-4): 1.44 (9H, s), 1.80 (3H, t, J=2.5 Hz), 3.11 (2H, d, J=7.0 Hz), 4.12 (1H, t, J=7.0 Hz), 4.66 (2H, q, J=2.5 Hz), 6.96 (2H, d, J=8.5 Hz), 7.20 (2H, d, J=8.5 Hz)

Example 12

Synthesis of Compound 55

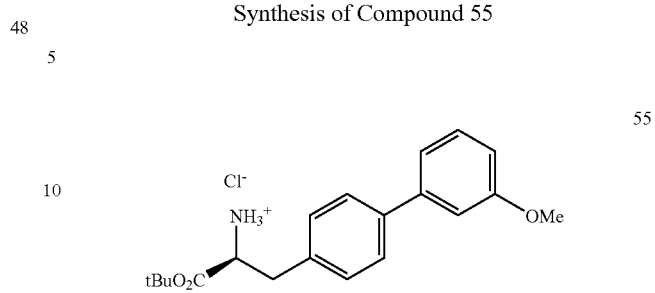

55

12-1 (Step 9-1)

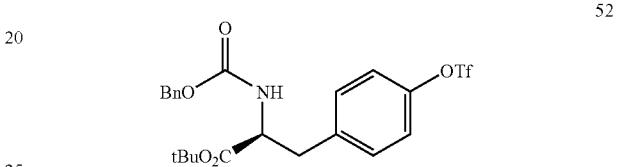

52

In the above formula, Tf is trifluoromethanesulfonyl.

To an anhydrous dichloromethane solution (400 mL) of N-benzyloxycarbonyl-L-tyrosine t-butyl ester (81.3 g), anhydrous pyridine (88.5 mL, 1.09 M) was added, followed by cooling to 0 to 5° C. Then, trifluoromethanesulfonic acid anhydride (43.0 mL, 262 mM) was added dropwise, followed by stirring at the same temperature for 2 hours. To the reaction solution, water (800 mL) and dichloromethane (1 L) were added, to be separated, and the organic layer was washed sequentially with a 0.5 N aqueous sodium hydroxide solution (650 mL), water (800 mL), 1N hydrochloric acid (2×1 L) and water (1 L). The organic layer was dried with anhydrous sodium sulfate, and concentrated, to obtain Compound 52 (105.9 g) as a milky white solid.

Physicochemical Property of Compound 52

Molecular weight: 503

ESI (LC/MS positive mode) 504 (M+H$^+$)

$^1$H-NMR Chemical shift value δ (in deuterated chloroform): 1.37 (9H, s), 3.10 (2H, d, J=6.5 Hz), 4.52 (1H, dt, J=7.5, 6.5 Hz), 5.07 (1H, d, J=12.5 Hz), 5.12 (1H, d, J=12.5 Hz), 5.30 (1H, d, J=7.5 Hz), 7.16 (2H, d, J=9.0 Hz), 7.23 (2H, d, J=9.0 Hz), 7.30-7.43 (5H, m)

12-2 (Step 9-2)

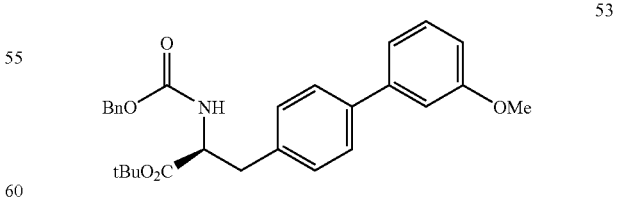

53

Compound 52 (5.0 g), 3-methoxyphenylboronic acid (2.57 g, 16.9 mM) and potassium carbonate (2.33 g, 16.9 mM) were suspended in anhydrous toluene (100 mL), and under a nitrogen atmosphere tetrakis(triphenylphosphine)palladium (276 mg, 0.239 mM) was added. After stirring was carried out at 90° C. for 17 hours under a nitrogen air stream, the reaction mixture was filtered through Celite, and the residue was washed with ethyl acetate (150 mL). The filtrate was washed sequentially with a 0.5 N aqueous sodium hydroxide solution (150 ml), water (150 mL), 1N hydrochloric acid (150 mL), water (150 mL) and brine (150 mL). After the organic layer was dried over anhydrous sodium sulfate, followed by concentration, crude Compound 53 (5.62 g) was obtained as a pale brown oily substance.

Physicochemical Property of Compound 53

Molecular weight: 461

ESI (LC/MS positive mode) 462 (M+H$^+$)

$^1$H-NMR Chemical shift value δ (in deuterated chloroform): 1.41 (9H, s), 3.12 (2H, d, J=6.0 Hz), 3.85 (3H, s), 4.57 (1H, dt, J=8.0, 6.0 Hz), 5.08 (1H, d, J=12.5 Hz), 5.13 (1H, d, J=12.5 Hz), 5.31 (1H, d, J=8.0 Hz), 6.86-6.91 (1H, m), 7.09-7.51 (12H, m)

12-3 (Step 9-3)

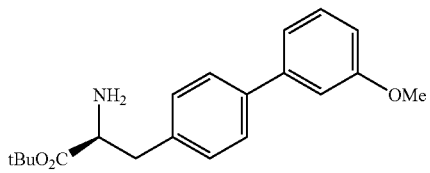

54

To a methanol solution (100 mL) of Compound 53 (5.52 g), 10% palladium carbon catalyst (700 mg) was added, followed by stirring at room temperature for 2 days under a hydrogen atmosphere (balloon). The reaction mixture was filtered through Celite, and the Celite was washed with methanol (30 mL). The oil resulting from the concentration of the filtrate was dissolved in ethyl acetate (100 mL), followed by extraction sequentially with 1N hydrochloric acid (100 mL), water (100 mL) and 0.1 N hydrochloric acid (100 mL). The aqueous layer and 0.1 N hydrochloric acid layer were combined, and the pH was adjusted to 8.0 with a saturated sodium hydrogencarbonate solution. After extraction with ethyl acetate (100 mL), the organic layer was washed with water (50 mL), and dried over anhydrous sodium sulfate, followed by concentration, to obtain Compound 54 (2.43 g) as a colorless oil.

Physicochemical Property of Compound 54

Molecular weight: 327

ESI (LC/MS positive mode) 328 (M+H$^+$)

$^1$H-NMR Chemical shift value δ (in deuterated chloroform): 1.44 (9H, s), 2.88 (1H, dd, J=13.5, 8.0 Hz), 3.08 (1H, dd, J=13.5, 5.5 Hz), 3.64 (1H, dd, J=8.0, 5.5 Hz), 3.86 (3H, s), 6.89 (1H, ddd, J=8.0, 2.5, 1.0 Hz), 7.11 (1H, dd, J=2.5, 1.5 Hz), 7.17 (1H, ddd, J=8.0, 1.5, 1.0 Hz), 7.29 (2H, d, J=8.5 Hz), 7.35 (1H, t, J=8.0 Hz), 7.35 (2H, d, J=8.5 Hz)

12-4

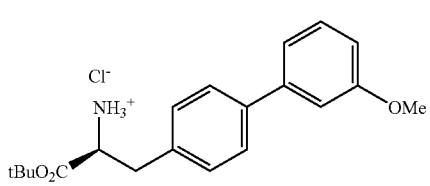

55

An ethyl acetate solution of Compound 54 (2.43 g) was cooled to 0 to 5° C., and 4N hydrochloric acid/ethyl acetate (2.80 mL, 11.2 mM) was added, followed by stirring at the same temperature for 1 hour. The precipitated powder was filtered off through Millipore filter (FR-20), which was washed with ethyl acetate (20 mL), followed by drying under reduced pressure with a vacuum pump, to obtain Compound 55 (2.6 g) as a colorless powder.

Physicochemical Property of Compound 55

Molecular weight: 327

ESI (LC/MS positive mode) 328 (M+H$^+$)

$^1$H-NMR Chemical shift value δ (in methanol d-4): 1.45 (9H, s), 3.22 (2H, d, J=7.0 Hz), 3.84 (3H, s), 4.21 (1H, t, J=7.0 Hz), 6.92 (1H, ddd, J=8.0, 2.5, 1.0 Hz), 7.14 (1H, dd, J=2.5, 1.5 Hz), 7.19 (1H, ddd, J=8.0, 1.5, 1.0 Hz), 7.35 (1H, t, J=8.0 Hz), 7.37 (2H, d, J=8.5 Hz), 7.63 (2H, d, J=8.5 Hz)

INDUSTRIAL APPLICABILITY

By using the method of the present invention, a compound having HCV replication inhibitory activity and desired optical activity can be synthesized selectively and at high yield in a small number of steps.

The invention claimed is:

1. A production process of a compound represented by the following formula (7-1):

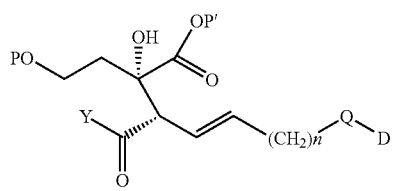

7-1 wherein Y represents a group represented by the following formula:

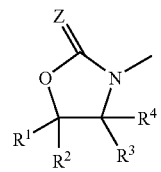

wherein $R^1$ to $R^4$ may be the same or different and respectively represent a hydrogen atom, optionally substituted aryl group, optionally substituted heteroaryl group, optionally substituted linear or branched alkyl group, optionally substituted linear or branched alkenyl group or optionally substituted linear or branched alkynyl group, and Z represents an oxygen atom or a sulfur atom;

Q represents a protected carbonyl group;

D represents —(CH$_2$)$_m$—R', where m represents an integer of 0 to 10, and R' represents a hydrogen atom, linear or branched alkyl group, linear or branched alkynyl group, linear or branched alkenyl group, cycloalkyl group, optionally substituted heterocyclic group, optionally substituted aryl group, optionally substituted heteroaryl group, —OX group, where X represents a hydrogen atom, linear or branched alkyl group, linear or branched alkynyl group, linear or branched alkenyl group, cycloalkyl group or optionally substituted aryl group, or halogen atom;

n represents an integer of 0 to 10;

P represents a protecting group of a hydroxyl group; and

P' represents a protecting group of a carboxyl group, comprising a step in which a compound represented by the following formula (1-8):

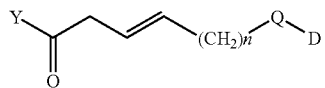

1-8 wherein Y, Q, D and n are the same as defined above, is reacted with a compound represented by the following formula (3-6):

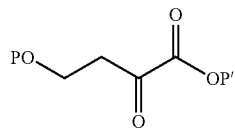

3-6 wherein P and P' are the same as defined above, in the presence of a base.

2. The production process according to claim 1, wherein the step in which the reaction is carried out in the presence of a base is carried out further in the presence of lithium chloride.

* * * * *